US008394938B2

(12) United States Patent
Santner et al.

(10) Patent No.: US 8,394,938 B2
(45) Date of Patent: Mar. 12, 2013

(54) ARTIFICIAL ENTROPIC BRISTLE DOMAIN SEQUENCES AND THEIR USE IN RECOMBINANT PROTEIN PRODUCTION

(75) Inventors: Aaron A. Santner, Avon, IN (US); Carrie Hughes Croy, Fishers, IN (US); Farha Huseini Vasanwala, Carmel, IN (US); Vladimir N. Uversky, Carmel, IN (US); A. Keith Dunker, Indianpolis, IN (US)

(73) Assignee: Molecular Kinetics Incorporated, Indianapolis, IN (US)

( * ) Notice: Subject to any disclaimer, the term of this patent is extended or adjusted under 35 U.S.C. 154(b) by 0 days.

(21) Appl. No.: 13/324,734

(22) Filed: Dec. 13, 2011

(65) Prior Publication Data

US 2012/0190822 A1 Jul. 26, 2012

Related U.S. Application Data

(63) Continuation of application No. 12/886,280, filed on Sep. 20, 2010, now Pat. No. 8,084,597, which is a continuation-in-part of application No. 12/272,558, filed on Nov. 17, 2008.

(60) Provisional application No. 60/988,319, filed on Nov. 15, 2007.

(51) Int. Cl.
*C07H 21/02* (2006.01)
*C12N 15/00* (2006.01)
*C12N 1/20* (2006.01)
*C12P 21/06* (2006.01)

(52) U.S. Cl. ................ 536/23.1; 435/320.1; 435/252.1; 435/69.1

(58) Field of Classification Search ........................ None
See application file for complete search history.

(56) References Cited

U.S. PATENT DOCUMENTS 8,084,597 B2 12/2011 Santner et al. ............... 536/23.4

OTHER PUBLICATIONS

Hoh ("Functional Protein Domains From the Thermally Driven Motion of Polypeptide Chains: A Proposal," Proteins: Structure, Function, and Genetics 32(2): 223-228, Aug. 1, 1998).*

Abrahmsen et al., "Secretion of heterologous gene products to the culture medium of *Escherichia coli*," Nucleic Acids Research 14(18): 7487-7500, 1986.

Braun et al., "Proteome-scale purification of human proteins from bacteria," Procedure of National Academy of Sciences USA 99(5): 2654-2659, Mar. 5, 2002.

Dunker et al., "Intrinsically disordered protein," Journal of Molecular Graphics and Modelling 19(1): 26-59, 2001.

Dyson et al, "Production of soluble mammalian proteins in *Escherichia coli*: identification of protein features that correlate with successful expression," BMC Biotechnology 4(1): 32, Dec. 14, 2004.

Fox et al., "Maltodextrin-binding proteins from diverse bacteria and archaea are potent solubility enhancers," FEBS Letters 537: 53-57, 2003.

Gottesman et al., "Deg Phenotype of *Escherichia coli* Ion Mutants," Journal of Bacteriology 133(2): 844-851, Feb. 1978.

Hammarström, et al., "Rapid screening for improved solubility of small human proteins produced as fusion proteins in *Escherichia coli*," Protein Science 11: 313-321, 2002.

Hoh, J.H., "Functional Protein Domains From the Thermally Driven Motion of Polypeptide Chains: A Proposal," Proteins: Structure, Function, and Genetics 32(2): 223-228, Aug. 1, 1998.

Itakura et al., "Expression in *Escherichia coli* of a Chemically Synthesized Gene for the Hormone Somatostatin," Science 198: 1056-1063, Dec. 9, 1977.

Kapust et al., "*Escherichia coli* maltose-binding protein is uncommonly effective at promoting the solubility of polypeptides to which it is fused," Protein Science 8: 1668-1674, 1999.

Kataeva et al., "Improving Solubility of *Shewanella oneidensis* MR-1 and *Clostridium thermocellum* JW-20 Proteins Expressed into *Escherichia coli*," Journal of Proteome Research 4(6): 1942-1951, 2005.

Milner, S.T., "Polymer Brushes," Science 251: 905-914, Feb. 22, 1991.

Napper, D.H., "Polymeric Stabilization of Colloidal Dispersions: Stabilization by Attached Polymer: Steric Stabilization," Academic Press, London, 1983, pp. 18-30.

Nilsson et al , "Immobilization and purification of enzymes with staphylococcal protein A gene fusion vectors," EMBO Journal 4(4): 1075-1080, 1985.

Richarme et al., "Chaperone Properties of the Bacterial Periplasmic Substrate-binding Proteins," Journal of Biological Chemistry 272(25): 15607-15612, Jun. 20, 1997.

Romero et al., "Sequence Complexity of Disordered Protein," Proteins: Structure, Function, and Genetics 42(1): 38-48, 2001.

Sachdev et al., "Fusions to Maltose-Binding Protein: Control of Folding and Solubility in Protein Purification," Methods in Enzymology 326: 312-321, 2000.

Shen, S., "Multiple joined genes prevent product degradation in *Escherichia coli*," Proceedings of the National Academy of Sciences USA 81:4627-4631, Aug. 1984.

Sickmeier et al., "DisProt: the Database of Disordered Proteins," Nucleic Acids Research 35: D786-D793, 2007.

Smith, D.B., "Generating Fusions to Glutathione S-Transferase for Protein Studies," Methods in Enzymology 326: 254-270, 2000.

Takagi et al., "Characterization of DNA Polymerase from *Pyrococcus* sp. Strain KOD1 and Its Application to PCR," Applied and Environmental Microbiology 63(11): 4504-4510, 1997.

Vaillancourt et al., "Recovery of Polypeptides Cleaved from Purified Calmodulin-Binding Peptide Fusion Proteins," BioTechniques 22(3): 451-453, Mar. 1997.

Vucetic et al., "DisProt: a database of protein disorder," BioInformatics 21(1): 137-140, 2005.

Zhan et al., "Structural analysis of regulatory protein domains using GST-fusion proteins," Gene 281: 1-9, 2001.

*Primary Examiner* — Suzanne M Noakes
*Assistant Examiner* — Jae W Lee
(74) *Attorney, Agent, or Firm* — Seed IP Law Group PLLC

(57) ABSTRACT

Compositions and methods for recombinant protein production and, more particularly, fusion polypeptides, polynucleotides encoding fusion polypeptides, expression vectors, kits, and related methods for recombinant protein production.

7 Claims, 9 Drawing Sheets psxspspxppqpsxppqsxxpqsqspppqsspXsppXppqsXqqp
sspspqqpsXXssssqsqpsqxsspxssxpppsqxppxpxpxpppx
spqsxpqqx

*Fig. 2A*

EB+
KsppKppqsKqqpsspspqqpsK
Kssssqs

EB-
EsppEppqsEqqpsspspqqpsE
Essssqs

EB0
GsppGppqsGqqpsspspqqps
GGssssqs

*Fig. 2B*

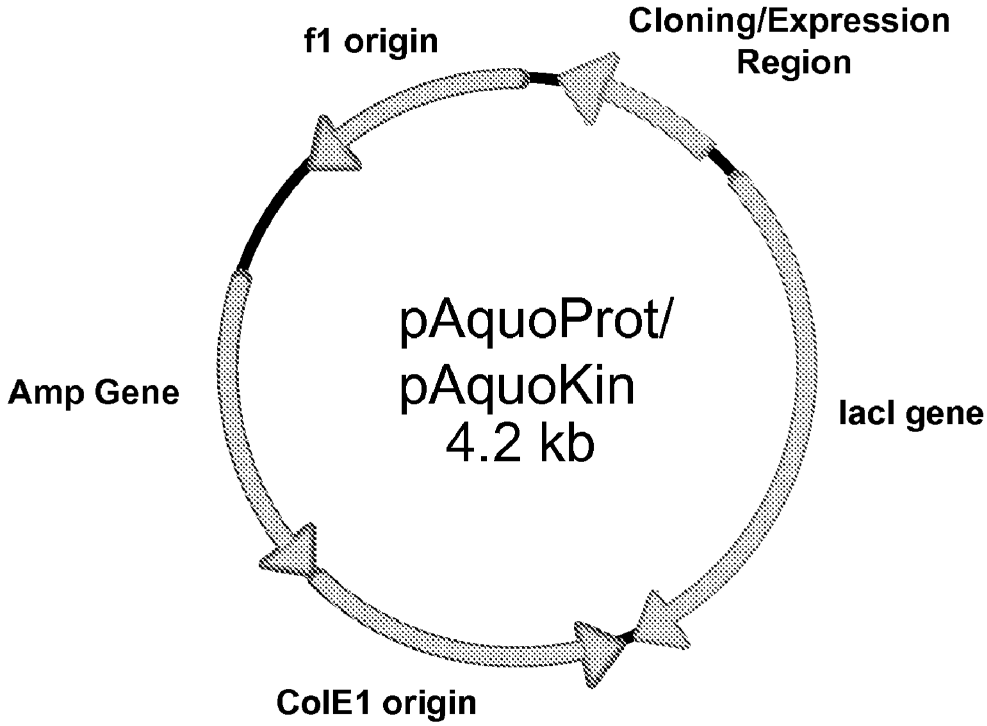
Figure 5: pAquoProt and pAquoKin Vector Map

```
             12 SalI                                                                  71 XbaI
                |                    T7 promoter       lac operater              |
  1  TCGATCAGCTGGTCGACCGCGAATTAATACGACTCACTATAGGGGAATTGTGAGCGGATAACAATTCCCCTCTAGAAATA
     AGCTAGTCGACCAGCTGGCGCTTAATTATGCTGAGTGATATCCCCTTAACACTCGCCTATTGTTAAGGGGAGATCTTTAT

                                    110 NcoI                             144 BstBI    entero-
                           RBS         |         His Tag                       |      kinase
 81  ATTTTGTTTAACTTTAAGAAGGAGATATACCATGGCACACCATCACCATCACCACGGTGCCGGTTCGAATGATGACGACG
     TAAAACAAATTGAAATTCTTCCTCTATATGGTACCGTGTGGTAGTGGTAGTGGTGCCACGGCCAAGCTTACTACTGCTGC
                                      M  A  H  H  H  H  H  H  G  A  G  S  N  D  D  D  D

                                    193 KpnI              206 EagI
               171 BamHI 177 MfeI 187 EcoRV   199 HindIII 205 NotI 214 XhoI
                  |     |        |       |      |      ||      |               HA Tag
161  ACAAGAGTCCGGATCCCAATTGGGAGGATATCGGTACCAAGCTTGCGGCCGCACTCGAGGGTTACCCATACGATGTTCCA
     TGTTCTCAGGCCTAGGGTTAACCCTCCTATAGCCATGGTTCGAACGCCGGCGTGAGCTCCCAATGGGTATGCTACAAGGT
       K  S  P  D  P  N  W  E  D  I  G  T  K  L  A  A  A  L  E  G  Y  P  Y  D  V  P

                         264 PacI   272 AvrII
                            |         |                                  T7 terminator
241  GATTACGCTTAAACTAGCGTAGCTTAATTAACCTAGGCTGCTGCCACCGCTGAGCAATAACTAGCATAACCCCTTGGGGC
     CTAATGCGAATTTGATCGCATCGAATTAATTGGATCCGACGACGGTGGCGACTCGTTATTGATCGTATTGGGGAACCCCG
     D  Y  A  *

                                                       366 NdeI
                                                          |
321  CTCTAAACGGGTCTTGAGGGGTTTTTTGCTGAAAGGAGATCTGAACATATGCCGG
     GAGATTTGCCCAGAACTCCCCAAAAAACGACTTTCCTCTAGACTTGTATACGGCC
```

Figure 6: Cloning and expression region of pAquoProt vector

```
            12 SalI                                                            71 XbaI
               |           _____T7 promoter___   ________lac operater_______       |
  1  TCGATCAGCTGGTCGACCGCGAATTAATACGACTCACTATAGGGGAATTGTGAGCGGATAACAATTCCCCTCTAGAAATA
     AGCTAGTCGACCAGCTGGCGCTTAATTATGCTGAGTGATATCCCCTTAACACTCGCCTATTGTTAAGGGGAGATCTTTAT

                                110 NcoI                                144 BstBI  enterokinase
                       RBS        |      ______His Tag_________              |      kinase(EK)
 81  ATTTTGTTTAACTTTAAGAAGGAGATATACCATGGCACACCATCACCATCACCACGGTGCCGGTTCGAATGATGACGACG
     TAAAACAAATTGAAATTCTTCCTCTATATGGTACCGTGTGGTAGTGGTAGTGGTGCCACGGCCAAGCTTACTACTGCTGC
                                       M  A  H  H  H  H  H  H  G  A  G  S  N  D  D  D  D

                                   193 KpnI           206 EagI
          171 BAMHI 177 MfeI  187 EcoRV      199 HindIII 205 NotI  214 XhoI
     _____      |      |         |      |       |      ||      |         __FLAG-Tag/EK site__
161  ACAAGAGTCCGGATCCCAATTGGGAGGATATCGGTACCAAGCTTGCGGCCGCACTCGAGGGTGATTACAAGGATGACGAC
     TGTTCTCAGGCCTAGGGTTAACCCTCCTATAGCCATGGTTCGAACGCCGGCGTGAGCTCCCAGATTACAAGGATGACGAC
       K  S  P  D  P  N  W  E  D  I  G  T  K  L  A  A  A  L  E  G  D  Y  K  D  D  D

       247 Eco47III             264 PacI   272 AvrII
     ______|                    |          |                              ___T7 terminator__
241  GATAAGAGCGCTTAAACTAGCGTAGCTTAATTAACCTAGGCTGCTGCCACCGCTGAGCAATAACTAGCATAACCCCTTGG
     CTATTCTCGCGAATTTGATCGCATCGAATTAATTGGATCCGACGACGGTGGCGACTCGTTATTGATCGTATTGGGGAACC
     D  K  S  A  *

                                                                366 NdeI
     _________________________________                             |
321  GGCCTCTAAACGGGTCTTGAGGGGTTTTTTGCTGAAAGGAGATCTGAACATATGCCGGAT
     CCGGAGATTTGCCCAGAACTCCCCAAAAAACGACTTTCCTCTAGACTTGTATACGGCCTA
```

Figure 7: Cloning and expression region of pAquoKin vector

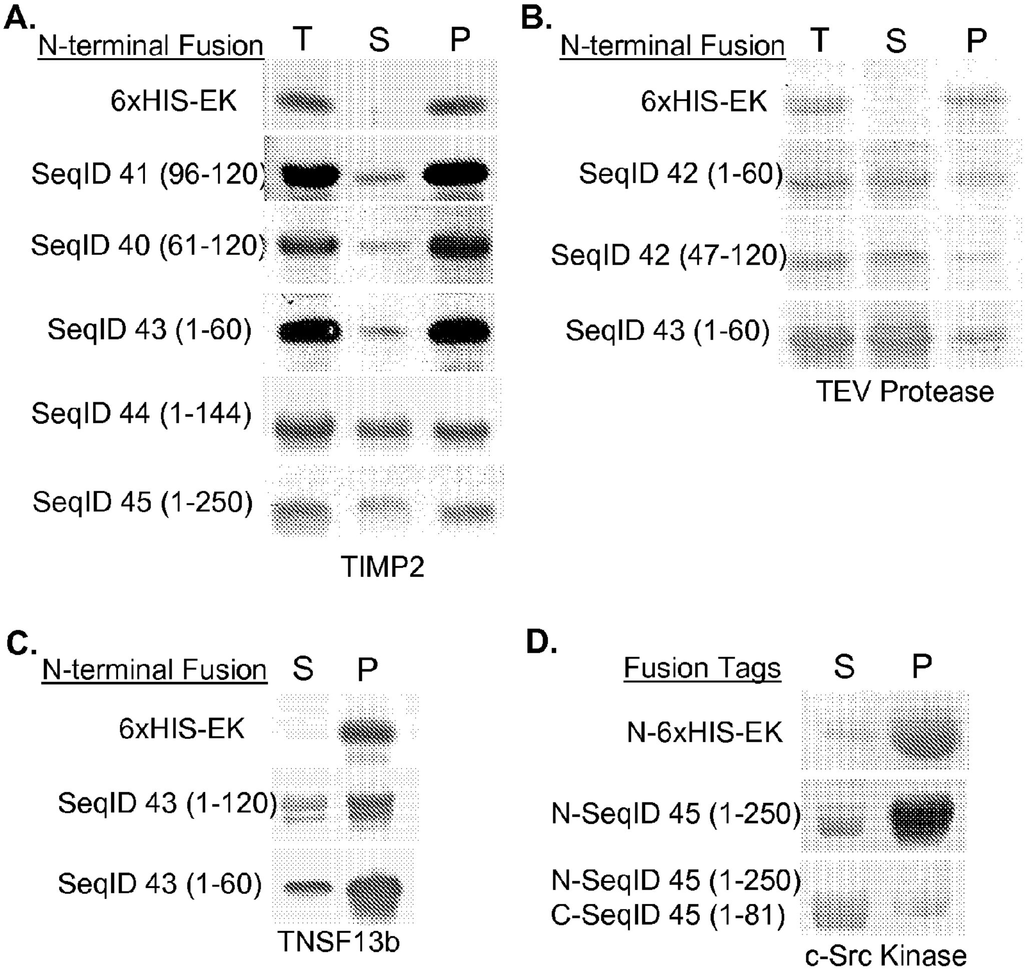
Figure 8: EBD-fusions Promote Target Protein Solubility.

ARTIFICIAL ENTROPIC BRISTLE DOMAIN SEQUENCES AND THEIR USE IN RECOMBINANT PROTEIN PRODUCTION

CROSS-REFERENCE TO RELATED APPLICATIONS

This application is a continuation of U.S. patent application Ser. No. 12/886,280, filed Sep. 20, 2010, which is a continuation-in-part of U.S. patent application Ser. No. 12/272,558, filed Nov. 17, 2008, which application claims the benefit under 35 U.S.C. §119(e) of U.S. Provisional Patent Application No. 60/988,319, filed Nov. 15, 2007; where these applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 670098_406C2_SEQUENCE_LISTING.txt. The text file is 173 KB, was created on Dec. 13, 2011 and is being submitted electronically via EFS-Web, concurrent with the filing of the specification.

FIELD OF THE INVENTION

The present invention relates generally to compositions and methods for improved recombinant protein production and, more particularly, to fusion polypeptides, polynucleotides encoding fusion polypeptides, expression vectors, kits, and related methods for recombinant protein production.

DETAILED DESCRIPTION OF THE RELATED ART

A large percentage of the proteins identified via the different genome sequencing effort have been difficult to express and/or purify as recombinant proteins using standard methods. For example, a trial study using *Methanobacterium thermoautotrophicum* as a model system identified a number of problems associated with high throughput structure determination (Christendat et al. (2000) *Prog. Biophys. Mol. Biol.* 73(5): 339-345; Christendat et al. (2000) *Nat Struct Biol* 7(10): 903-909). The complete list of genome-encoded proteins was filtered to remove proteins with predicted transmembrane regions or homologues to known structures. When these filtered proteins were taken through the cloning, expression, and structural determination steps of a high throughput process, only about 50% of the selected proteins could be purified in a state suitable for structural studies, with roughly 45% of large expressed proteins and 30% of small expressed proteins failing due to insolubility. The study concluded that considerable effort must be invested in improving the attrition rate due to proteins with poor expression levels and unfavorable biophysical properties. (Christendat et al., (2000) *Prog. Biophys. Mol. Biol.* 73(5): 339-345; Christendat et al. (2000) *Nat Struct Biol* 7(10): 903-909).

Similar results have been observed for other prokaryotic proteomes. One study reported the successful cloning and attempted expression of 1376 (73%) of the predicted 1877 genes of the *Thermotoga maritima* proteome. However, crystallization conditions were able to be determined for only 432 proteins (23%). A significant component of the decrease between the cloned and crystallized success levels was due to poor protein solubility and stability (Kuhn et al. (2002) *Proteins* 49(1): 142-5).

Similarly low success rates have been reported for eukaryotic proteomes. A study of a sample set of human proteins, for example, reported that the failure rate using high-throughput methods for three classes of proteins based on cellular location was 50% for soluble proteins, 70% for extracellular proteins, and more than 80% for membrane proteins (Braun et al. (2002) *Proc Natl Acad Sci USA* 99(5): 2654-9).

Interactions between individual recombinant proteins are responsible for a significant number of the previously mentioned failures. In a high-throughput structural determination study, Christendat and colleagues found that 24 of 32 proteins that were classified by nuclear magnetic resonance as aggregated displayed circular dichroism spectra consistent with stable folded proteins, suggesting that these proteins were folded properly but aggregated due to surface interactions (Christendat et al. (2000) *Prog. Biophys. Mol. Biol.* 73(5): 339-345). One possible explanation for this is that these proteins function in vivo as part of multimeric units but when they are recombinantly expressed, dimerization domains are exposed that mediate protein-protein interactions.

Prior methods used to increase recombinant protein stability include production in *E. coli* strains that are deficient in proteases (Gottesman and Zipser (1978) *J Bacteriol* 133(2): 844-51) and production of fusions of bacterial protein fragments to a recombinant polypeptide/protein of interest (Itakura et al., *Science,* 1977. 198:1056-63; Shen, *Proc Natl Acad Sci USA,* 1984. 81:4627-31). It has also been attempted to stabilize foreign proteins in *E. coli*. In addition, fusing a leader sequence to a recombinant protein may cause a gene product to accumulate in the periplasm or be excreted, which may result in increased recovery of properly folded soluble protein (Nilsson et al., *EMBO J,* 1985. 4:1075-80; Abrahmsen et al., *Nucleic Acids Res,* 1986. 14:7487-500). These strategies have advantages for some proteins but they generally do not succeed when used, for example, with membrane proteins or proteins capable of strong protein-protein interactions.

Fusion polypeptides have also been used as an approach for improving the solubility and folding of recombinant polypeptides/proteins produced in *E. coli* (Zhan et al., Gene, 2001. 281:1-9). Some commonly used fusion partners which have been linked to heterologous protein sequences of interest include calmodulin-binding peptide (CBP) (Vaillancourt et al., *Biotechniques,* 1997. 22:451-3), glutathione-S-transferase (GST) (Smith, *Methods Enzymol,* 2000. 326:254-70), thioredoxin (TRX) (Martin Hammarström et al., *Protein Science,* 2002. 11:313-321), and maltose-binding protein (MBP) (Sachdev et al., *Methods Enzymol,* 2000. 326:312-21). Glutathione-S-transferase and maltose-binding protein have been found to increase the recombinant protein purification success rate when fused to a heterologous sequence in a controlled trial of 32 human test proteins (Braun et al., *Proc Natl Acad Sci USA,* 2002. 99:2654-9). Further, maltose-binding protein domain fusions have been shown to increase the solubility of recombinant proteins (Kapust et al., *Protein Sci,* 1999. 8:1668-74; Braun et al., *Proc Natl Acad Sci USA,* 2002. 99:2654-9; Martin Hammarström et al., *Protein Science,* 2002. 11:313-321). Maltose-binding protein may further benefit recombinant protein solubility and folding in that it may have chaperone-like properties that assist in folding of the fusion partner (Richarme et al., *J Biol Chem,* 1997. 272: 15607-12; Bach et al., *J Mol Biol,* 2001. 312:79-93. However, these fusion approaches used to date have not been amendable to all classes of proteins, and have thus met with only limited success.

Entropic bristles have been used in a variety of polymers to reduce aggregation of small particles such as latex particles in paints and to stabilize a wide variety of other colloidal products (Hoh, *Proteins,* 1998. 32:223-228). Entropic bristles generally comprise amino acid residues that do not have a tendency to form secondary structure and in the process of random motion about their attachment points sweep out a significant region in space and entropically exclude other molecules by their random motion (Hoh, *Proteins,* 1998. 32:223-228). Entropic bristles are singular elements, comprising highly flexible, non-aggregating polymer chains, of which entropic brushes are assembled. In polymer chemistry, entropic bristles have been affixed to the surfaces of particles (e.g. latex beads), thereby forming entropic brushes which, in turn, prevent particle aggregation (*Stabilization by attached polymer: steric stabilization*, in *Polymeric stabilization of colloidal dispersions*, D. H. Napper, Editor. 1983, Academic Press: London. p. 18-30). EBDs can exclude large molecules but do not exclude small molecules such as water, salts, metal ions, or cofactors (Hoh, *Proteins,* 1998. 32:223-228).

EBDs can also function as steric stabilizers and operate through steric hindrance stabilization (*Stabilization by attached polymer: steric stabilization*, in *Polymeric stabilization of colloidal dispersions*, D. H. Napper, Editor. 1983, Academic Press: London. p. 18-30). Naper described characteristics that contribute to steric stabilization functions, including (1) they have an amphipathic sequence; (2) they are attached to the colloidal particle by one end rather than being totally adsorbed; (3) they are soluble in the medium used; (4) they are mutually repulsive; (5) they are thermodynamically stable; and (6) they exhibit stabilizing ability in proportion to their length. Steric stabilizers intended to function in aqueous media extend from the surface of colloidal molecules thus transforming their surfaces from hydrophobic to hydrophilic. The fact that sterically stabilized particles are thermodynamically stable leads them to spontaneously re-disperse when dried residue is reintroduced to solvent. Entropic bristles can adopt random-walk configurations in solution (Milner, *Science,* 1991. 251:905-914). These chains extend from an attachment point because of their affinity for the solvent. This affinity is due in part to the highly charged nature of the entropic bristle sequence.

While naturally-occurring EBDs possess features desirable for use in improving the solubility, folding, etc., of recombinant proteins, prior attempts at using EBD sequences in fusion with heterologous protein sequences have met with limited success, due in part to cellular toxicity associated with the naturally occurring EBDs. Accordingly, there remains a need for new compositions and methods for improving the properties and characteristics of recombinant proteins, e.g., improving solubility, stability, yield and/or folding of recombinant proteins. The present invention addresses these needs and offers other related advantages by providing non-naturally occurring EBD sequences as fusion partners for use in recombinant protein production techniques, as described herein.

SUMMARY OF THE INVENTION

According to a general aspect of the present invention, there are provided isolated fusion polypeptides comprising at least one artificial, non-naturally occurring entropic bristle domain (EBD) sequence and at least one heterologous polypeptide sequence of interest. The fusion polypeptides comprising artificial EBD sequences as described herein offer a number of advantages over prior fusion polypeptides and methods relating thereto. For example, the fusion polypeptides of the invention offer increased solubility relative to the heterologous polypeptide sequence, reduced aggregation relative to the heterologous polypeptide sequence and/or improved folding relative to the heterologous polypeptide sequence.

In one illustrative embodiment, the invention provides fusion polypeptides comprising at least one non-naturally occurring entropic bristle domain (EBD) polypeptide sequence and at least one heterologous polypeptide sequence to be expressed, wherein the EBD polypeptide sequence is about 10-1000 amino acid residues in length, and wherein at least 75% of the residues of the EBD polypeptide sequence are selected from G, D, M, K, R, S, Q, P, and E. In other embodiments, at least 80, 85, 90 or 95% of the residues of the EBD polypeptide sequence are selected from G, D, M, K, R, S, Q, P, and E.

In another illustrative embodiment, the EBD polypeptide sequence is positively charged and the amino acid residues which make up the EBD polypeptide comprise disorder-promoting amino acid residues selected from P, Q, S and K. In a more specific embodiment, the disorder-promoting amino acid residues P, Q, S and K are present in about the following amino acid ratios: K:P:Q:S=1:2:1:1, K:P:Q:S=1:4:1:1, K:P:Q:S=2:2:1:1, K:P:Q:S=3:2:1:1, K:P:Q:S=1:2:1:2, K:P:Q:S=2:2:1:2, K:P:Q:S=3:2:1:2, K:P:Q:S=4:2:1:2, or K:P:Q:S=5:2:1:2. In a more specific embodiment, the EDB polypeptide sequence comprises a sequence set forth in SEQ ID NO: 1, SEQ ID NO: 2, SEQ ID NO: 3, SEQ ID NO: 4, SEQ ID NO: 5, SEQ ID NO: 23, or SEQ ID NO: 24, or a fragment thereof, or a sequence having at least 90% identity thereto.

In another illustrative embodiment, the EBD polypeptide sequence is negatively charged and the amino acid residues are disorder-promoting amino acid residues selected from P, Q, S and E. In a more specific embodiment, the disorder-promoting amino acid residues P, Q, S and E are present in about the following amino acid ratios: E:P:Q:S=1:2:1:1, E:P:Q:S=1:4:1:1, E:P:Q:S=2:2:1:1, E:P:Q:S=3:2:1:1, E:P:Q:S=1:2:1:2, E:P:Q:S=2:2:1:2, E:P:Q:S=3:2:1:2, E:P:Q:S=4:2:1:2, or E:P:Q:S=5:2:1:2. In a more specific embodiment, the EDB polypeptide comprises the sequence set forth in SEQ ID NO: 6, SEQ ID NO: 7, SEQ ID NO: 8, SEQ ID NO: 9, SEQ ID NO: 10, SEQ ID NO: 25, SEQ ID NO: 26, SEQ ID NO: 38, SEQ ID NO: 39, SEQ ID NO: 40, or a fragment thereof, or a sequence having at least 90% identity thereto.

In another illustrative embodiment, the EBD polypeptide sequence is negatively charged and the amino acid residues are disorder-promoting amino acid residues selected from P, Q, G and E. In a more specific embodiment, the disorder-promoting amino acid residues P, Q, G and E are present in about the following amino acid ratios: E:P:Q:G=1:2:1:1, E:P:Q:G=1:4:1:1, E:P:Q:G=2:2:1:1, E:P:Q:G=3:2:1:1, E:P:Q:G=1:2:1:2, E:P:Q:G=2:2:1:2, E:P:Q:G=3:2:1:2, E:P:Q:G=4:2:1:2, or E:P:Q:G=5:2:1:2. In a more specific embodiment, the EDB polypeptide comprises the sequence set forth in SEQ ID NO: 41, SEQ ID NO: 42, SEQ ID NO: 43, or a fragment thereof, or a sequence having at least 90% identity thereto.

In another illustrative embodiment, the EBD polypeptide sequence is negatively charged and the amino acid residues are disorder-promoting amino acid residues selected from P, Q, S, G, D and E. In a more specific embodiment, the disorder-promoting amino acid residues P, Q, S, G, D and E are present in about the following amino acid ratios: D:E:P:Q:S:G=1:2:3:1:2:1. In a more specific embodiment, the EDB polypeptide comprises the sequence set forth in SEQ ID NO: 44, or a fragment thereof, or a sequence having at least 85% identity thereto such as the sequence set forth in SEQ ID NO: 45.

In yet another illustrative embodiment, the EBD polypeptide sequence is neutral and the disorder-promoting residues are selected from P, Q, S and G. In a more particular embodiment, the amino acid residues P, Q, S and G are present in about the amino acid ratio of G:P:Q:S=1:2:1:2. In a more particular embodiment, the EDB polypeptide comprises the sequence set forth in SEQ ID NO: 11, SEQ ID NO: 27, or SEQ ID NO: 28, or a fragment thereof, or a sequence having at least 90% identity thereto.

In another illustrative embodiment, the EBD polypeptide sequence is positively charged and the amino acid residues are disorder-promoting amino acid residues selected from P, Q, S and R. In a more specific embodiment, the amino acid residues R, P, Q and S are present in about the following amino acid ratios: R:P:Q:S=1:2:1:2, R:P:Q:S=2:2:1:2, R:P:Q:S=3:2:1:2, R:P:Q:S=4:2:1:2, or R:P:Q:S=5:2:1:2.

In another illustrative embodiment, the EBD polypeptide sequence is negatively charged and the amino acid residues are disorder-promoting amino acid residues are selected from P, Q, S and D. In a more particular embodiment, the amino acid residues D, P, Q and S are present in about the following amino acid ratios: D:P:Q:S=1:2:1:2, D:P:Q:S=2:2:1:2, D:P:Q:S=3:2:1:2, D:P:Q:S=4:2:1:2, or D:P:Q:S=5:2:1:2.

A fusion polypeptide of the invention, comprising an EBD sequence and a heterologous polypeptide sequence, exhibits improved solubility relative to the corresponding heterologous polypeptide in the absence of the EBD sequence. In a related embodiment, the fusion polypeptide has at least 5% increased solubility relative to the heterologous polypeptide sequence, at least 25% increased solubility relative to the heterologous polypeptide sequence, or at least 50% increased solubility relative to the heterologous polypeptide sequence.

In another embodiment, a fusion polypeptide of the invention exhibits reduced aggregation relative to the level of aggregation of the heterologous polypeptide sequence in the absence of the EBD sequence. For example, a fusion polypeptide of the invention generally exhibits at least 10% reduced aggregation relative to the heterologous polypeptide sequence or at least 25% reduced aggregation relative to the heterologous polypeptide sequence.

In another embodiment, a fusion polypeptide of the invention exhibits improved self-folding relative to the heterologous polypeptide sequence in the absence of the EBD sequence.

In another embodiment of the present invention, an EBD sequence employed in a fusion polypeptide comprises an amino acid sequence that maintains a substantially random coil conformation.

In another embodiment, the EBD sequence of a fusion polypeptide of the invention comprises an amino acid sequence that is substantially mutually repulsive.

In another embodiment, the EBD sequence of a fusion polypeptide of the invention comprises an amino acid sequence that remains in substantially constant motion.

In another embodiment of the present invention, the EBD sequence of a fusion polypeptide of the invention is a random sequence of disorder-promoting amino acid residues.

The EBD sequence of a fusion polypeptide of the invention generally comprises between about 5 to 1000 amino acid residues, 5 to 500 amino acid residues, 5 to 400 amino acid residues, 5 to 300 amino acid residues, 5 to 200 amino acid residues, 5 to 100 amino acid residues, 5 to 80 amino acid residues, 5 to 60 amino acid residues, 5 to 40 amino acid residues, 5 to 30 amino acid residues, 5 to 20 amino acid residues, 10 to 30 amino acid residues, 15 to 25 amino acid residues, 10 to 90 amino acid residues, 20 to 80 amino acid residues, 20 to 40 amino acid residues, 30 to 70 amino acid residues, or 40 to 60 amino acid residues.

In a related embodiment, the disorder-promoting EBD sequence comprises no more than about 20 amino acid residues, 30 amino acid residues, 40 amino acid residues, 50 amino acid residues, 100 amino acid residues, 200 amino acid residues, 300 amino acid residues, 400 amino acid residues, 500 amino acid residues, or 1000 amino acid residues.

In yet another related embodiment, the EBD sequence of a fusion polypeptide of the invention comprises at least 2-100 repeats of an EBD sequence set forth above or described herein, or a combination thereof.

In another embodiment, the EBD sequence of a fusion polypeptide of the invention comprises a combination of any one or more of fragments derived from disorder-promoting EBD sequences that are positively charged, negatively charges, or neutral as set here herein.

In another embodiment, an EBD sequence of a fusion polypeptide of the invention is cleavable, e.g., can be removed and/or separated from the heterologous polypeptide sequence after recombinant expression by, for example, enzymatic or chemical cleavage methods.

In another embodiment, an EBD sequence of a fusion polypeptide of the invention is covalently linked at the N-terminus of the heterologous polypeptide sequence of interest. In another embodiment, an EBD sequence of a fusion polypeptide of the invention is covalently linked at the C-terminus of the heterologous polypeptide sequence of interest. In yet another embodiment, an EBD sequence of a fusion polypeptide of the invention is covalently linked at the N- and C-termini of the heterologous polypeptide sequence of interest.

In another embodiment of the invention, the charge of an EBD sequence of a fusion polypeptide of the invention is modulated by, for example, enzymatic and/or chemical methods, in order to modulate the activity of the EBD sequence. In a particular embodiment, the charge of the EBD sequence is modulated by phosphorylation.

According to another aspect of the invention, an isolated polynucleotide is provided, wherein the polynucleotide encodes a fusion polypeptide as described herein or an artificial EBD sequence as described herein.

According to yet another aspect of the invention, there is provided an expression vector comprising an isolated polynucleotide encoding a fusion polypeptide as described herein or an artificial EBD sequence as described herein. In a related embodiment, an expression vector is provided comprising a polynucleotide encoding an EBD sequence and further comprising a cloning site for insertion of a polynucleotide encoding a heterologous polypeptide of interest.

According to yet another aspect of the invention, there is provided a host cell comprising an expression vector as described herein.

According to yet another aspect of the invention, there is provided a kit comprising an isolated polynucleotide as described herein, an isolated polypeptide as described herein and/or an isolated host cell as described herein.

Yet another aspect of the invention provides a method for producing a recombinant protein comprising the steps of: introducing into a host cell an expression vector comprising a polynucleotide sequence encoding a fusion polypeptide, the fusion polypeptide comprising at least one EBD sequence and at least one polypeptide sequence of interest; and expressing the fusion polypeptide in the host cell. In another embodiment, the method further comprises the step of isolating the fusion polypeptide from the host cell. In another related embodiment, the method further comprises the step of removing the EBD sequence from the fusion polypeptide before or after isolating the fusion polypeptide from the host cell.

These and other aspects of the present invention will become apparent upon reference to the following detailed description. All references disclosed herein and in the enclosed Application Data Sheet are hereby incorporated by reference in their entirety as if each was incorporated individually.

BRIEF DESCRIPTION OF THE DRAWINGS

FIGS. 2A and 2B. Amino acid sequence of the randomly generated artificial EB containing the chosen residues in the following proportion: X:P:Q:S=1:2:1:2 (SEQ ID NO:35); X=K, E or G (2A) and sequences of positive, negative and neutral bristles, indicated as $EB_+$ (SEQ ID NO:24), $EB_-$ (SEQ ID NO:26) and $EB_0$ (SEQ ID NO:28) (2B), respectively. The actual X:P:Q:S ratios for these sequences was 5:8:6:11, numbers that are close to the 1:2:1:2 used to generate the sequences.

FIG. 5. Vector map of the pAquoProt and pAquoKin *E. coli* expression plasmids that have been created to harbor entropic bristles. The pAquoProt and pAquoKin vectors are identical except within the expression/cloning region.

FIG. 6. Double stranded sequence of the expression/cloning region of the pAquoProt plasmid (SEQ ID NOS: 54 and 55). The expression/cloning region is comprised of the T7 promoter/operator, ribosomal binding site (RBS), coding sequences for a 6×His tag and enterokinase (EK) cleavage site, multicloning site, coding sequences for HA epitope tag, and T7 terminator (SEQ ID NO:56). The restriction enzymes listed are unique sites not present elsewhere in the plasmid. Entropic bristle domain coding sequences are introduced into the expression/cloning region at the BstBI site positioned between the 6×His tag and EK cleavage coding sequences.

FIG. 7. Double stranded sequence of the expression/cloning region of the pAquoKin plasmid (SEQ ID NOS: 57 and 58). The expression/cloning region is comprised of the T7 promoter/operator, ribosomal binding site (RBS), coding sequences for a 6×His tag and enterokinase cleavage site, multicloning site, coding sequences for the FLAG™ epitope tag, and T7 terminator (SEQ ID NO:59). The restriction enzymes listed are unique sites not present elsewhere in the plasmid. Entropic bristle domain coding sequences are introduced into the pAquoKin expression/cloning region at the BstBI site positioned between the 6×His tag and EK cleavage coding sequences and at the Eco47III site following the C-terminal FLAG™ coding sequence.

FIGS. 8A, 8B, 8C, and 8D. Expression and solubility of TIMP2 with a variety of N-terminal entropic bristles ranging in length from 24 to 250 amino acids or 6×His-EK control fusion (8A). Expression and solubility of TEV protease fused with 3 EBDs that are comprised of the same amino acids but have distinct primary amino acid sequences (8B). Expression and solubility of TNSF13b fused with a 120 amino acid EBD or a 60 amino acid fragment (8C). Expression and solubility of c-Src kinase with an N-terminal fusion or N- and C-terminal EBD fusions. c-Src with entropic bristles fused to both termini is more soluble than N-terminal c-Src fusions (8D). Abbreviations: T, total protein, S, soluble protein, P, insoluble pellet protein. IDs of solubilized proteins are shown below each set of blots.

BRIEF DESCRIPTION OF THE SEQUENCE IDENTIFIERS

Figure 1:
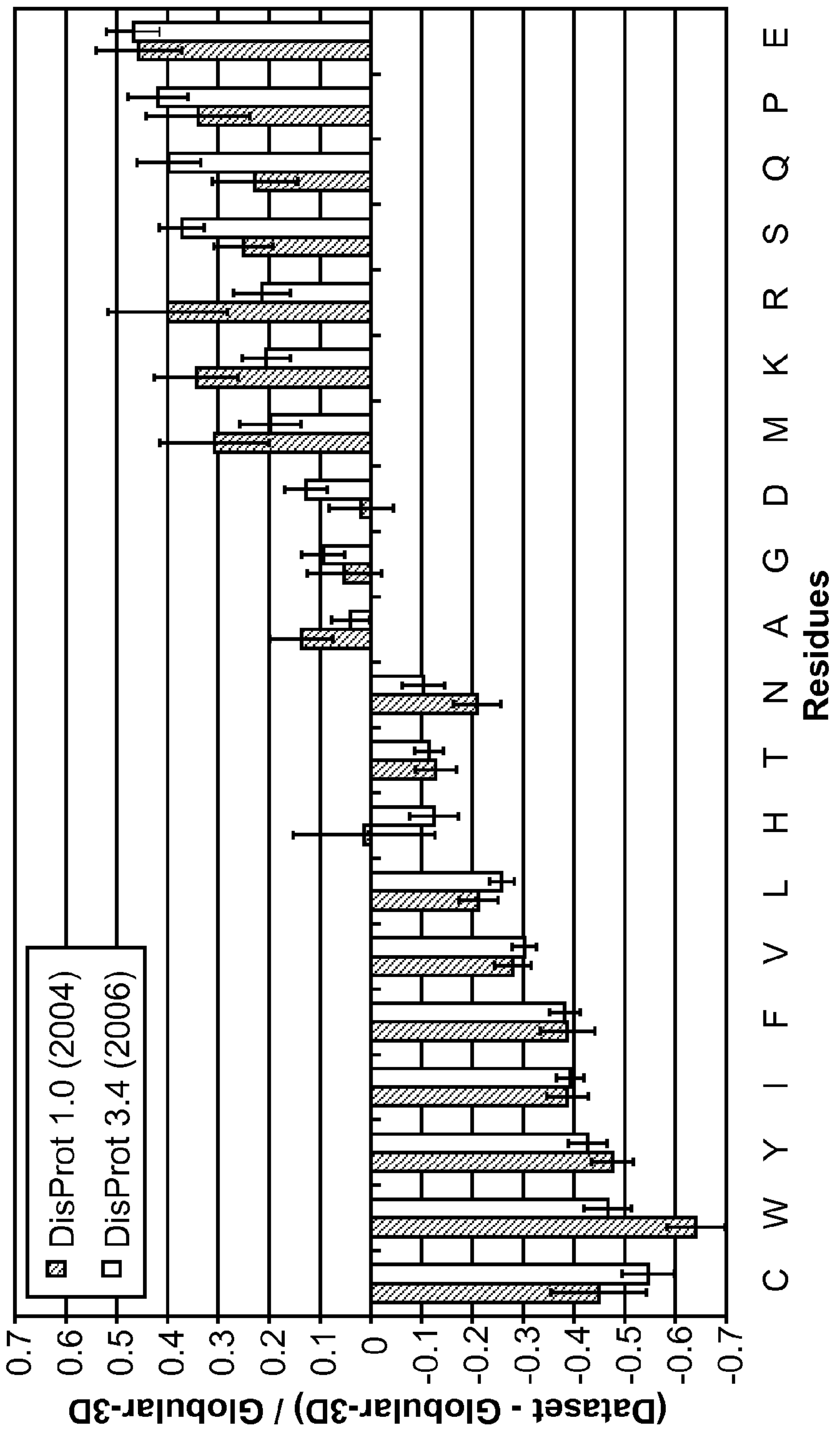
FIG. 1. Amino acid composition, relative to the set of globular proteins Globular-3D, of intrinsically disordered regions 10 residues or longer from the DisProt database. Slanted hash marks indicate DisProt 1.0 (152 proteins), while white indicates DisProt 3.4 (460 proteins). Amino acid compositions were calculated per disordered regions and then averaged. The arrangement of the amino acids is by peak height for the DisProt 3.4 release. Confidence intervals were estimated using per-protein bootstrapping with 10,000 iterations.

SEQ ID NO: 1 is the amino acid sequence of a positively charged EBD domain, EBD(+), which is a random sequence containing disorder-promoting residues P, Q, S and K in about the following amino acid ratios: K:P:Q:S=1:2:1:2. The sequence was produced using the random sequence generator tool located at the Swiss-Prot website: au.expasy.org/tools/randseq.html.

SEQ ID NO: 2 is the amino acid sequence of a positively charged EBD domain, EBD(++), which is a random sequence containing disorder-promoting residues P, Q, S and K in about the following amino acid ratios: K:P:Q:S=2:2:1:2. The sequence was produced using the random sequence generator tool located at the Swiss-Prot website: au.expasy.org/tools/randseq.html.

SEQ ID NO: 3 is the amino acid sequence of a positively charged EBD domain, EBD(+++), which is a random sequence containing disorder-promoting residues P, Q, S and K in about the following amino acid ratios: K:P:Q:S=3:2:1:2. The sequence was produced using the random sequence generator tool located at the Swiss-Prot website: au.expasy.org/tools/randseq.html.

SEQ ID NO: 4 is the amino acid sequence of a positively charged EBD domain, EBD(++++), which is a random sequence containing disorder-promoting residues P, Q, S and K in about the following amino acid ratios: K:P:Q:S=4:2:1:2. The sequence was produced using the random sequence generator tool located at the Swiss-Prot website: au.expasy.org/tools/randseq.html.

SEQ ID NO: 5 is the amino acid sequence of a positively charged EBD domain, EBD(+++++), which is a random sequence containing disorder-promoting residues P, Q, S and K in about the following amino acid ratios: K:P:Q:S=5:2:1:2. The sequence was produced using the random sequence generator tool located at the Swiss-Prot website: au.expasy.org/tools/randseq.html.

SEQ ID NO: 6 is the amino acid sequence of a negatively charged EBD domain, EBD(−), which is a random sequence containing disorder-promoting residues P, Q, S and E in about the following amino acid ratios: E:P:Q:S=1:2:1:2. The sequence was produced using the random sequence generator tool located at the Swiss-Prot website: au.expasy.org/tools/randseq.html.

SEQ ID NO: 7 is the amino acid sequence of a negatively charged EBD domain, EBD(−−), which is a random sequence containing disorder-promoting residues P, Q, S and E in about the following amino acid ratios: E:P:Q:S=2:2:1:2. The sequence was produced using the random sequence generator tool located at the Swiss-Prot website: au.expasy.org/tools/randseq.html.

SEQ ID NO: 8 is the amino acid sequence of a negatively charged EBD domain, EBD(−−−), which is a random sequence containing disorder-promoting residues P, Q, S and E in about the following amino acid ratios: E:P:Q:S=3:2:1:2. The sequence was produced using the random sequence generator tool located at the Swiss-Prot website: au.expasy.org/tools/randseq.html.

SEQ ID NO: 9 is the amino acid sequence of a negatively charged EBD domain, EBD(−−−−), which is a random sequence containing disorder-promoting residues P, Q, S and E in about the following amino acid ratios: E:P:Q:S=4:2:1:2. The sequence was produced using the random sequence generator tool located at the Swiss-Prot website: au.expasy.org/tools/randseq.html.

SEQ ID NO: 10 is the amino acid sequence of a negatively charged EBD domain, EBD(−−−−−) which is a random sequence containing disorder-promoting residues P, Q, S and E in about the following amino acid ratios: E:P:Q:S=5:2:1:2. The sequence was produced using the random sequence generator tool located at the Swiss-Prot website: au.expasy.org/tools/randseq.html.

SEQ ID NO: 11 is the amino acid sequence of a neutral EBD domain, EBD(0), which is a random sequence containing disorder-promoting residues P, Q, S and G in about the following amino acid ratios: G:P:Q:S=1:2:1:2. The sequence was produced using the random sequence generator tool located at the Swiss-Prot website: au.expasy.org/tools/randseq.html.

SEQ ID NO: 12 is a polynucleotide sequence encoding the amino acid sequence of SEQ ID NO: 1. Sequence was produced using the reverse translation tool located at: www.vivo.colostate.edu/molkit/rtranslate/index.html.

SEQ ID NO: 13 is a polynucleotide sequence encoding the amino acid sequence of SEQ ID NO: 2. Sequence was produced using the reverse translation tool located at: www.vivo.colostate.edu/molkit/rtranslate/index.html.

SEQ ID NO: 14 is a polynucleotide sequence encoding the amino acid sequence of SEQ ID NO: 3. Sequence was produced using the reverse translation tool located at: www.vivo.colostate.edu/molkit/rtranslate/index.html.

SEQ ID NO: 15 is a polynucleotide sequence encoding the amino acid sequence of SEQ ID NO: 4. Sequence was produced using the reverse translation tool located at: www.vivo.colostate.edu/molkit/rtranslate/index.html.

SEQ ID NO: 16 is a polynucleotide sequence encoding the amino acid sequence of SEQ ID NO: 5. Sequence was produced using the reverse translation tool located at: www.vivo.colostate.edu/molkit/rtranslate/index.html.

SEQ ID NO: 17 is a polynucleotide sequence encoding the amino acid sequence of SEQ ID NO: 6. Sequence was produced using the reverse translation tool located at: www.vivo.colostate.edu/molkit/rtranslate/index.html.

SEQ ID NO: 18 is a polynucleotide sequence encoding the amino acid sequence of SEQ ID NO: 7. Sequence was produced using the reverse translation tool located at: www.vivo.colostate.edu/molkit/rtranslate/index.html.

SEQ ID NO: 19 is a polynucleotide sequence encoding the amino acid sequence of SEQ ID NO: 8. Sequence was produced using the reverse translation tool located at: www.vivo.colostate.edu/molkit/rtranslate/index.html.

SEQ ID NO: 20 is a polynucleotide sequence encoding the amino acid sequence of SEQ ID NO: 9. Sequence was produced using the reverse translation tool located at: www.vivo.colostate.edu/molkit/rtranslate/index.html.

SEQ ID NO: 21 is a polynucleotide sequence encoding the amino acid sequence of SEQ ID NO: 10. Sequence was produced using the reverse translation tool located at: www.vivo.colostate.edu/molkit/rtranslate/index.html.

SEQ ID NO: 22 is a polynucleotide sequence encoding the amino acid sequence of SEQ ID NO: 11. Sequence was produced using the reverse translation tool located at: www.vivo.colostate.edu/molkit/rtranslate/index.html.

SEQ ID NO: 23 is the amino acid sequence of a positively charged EBD domain, EBD(+), which is a random sequence containing disorder-promoting residues P, Q, S and K in about the following amino acid ratios: K:P:Q:S=1:2:1:2.

The sequence was produced using the random sequence generator tool located at the Swiss-Prot website: au.expasy.org/tools/randseq.html.

SEQ ID NO: 24 is the amino acid sequence of a positively charged EBD domain of SEQ ID NO: 23.

SEQ ID NO: 25 is the amino acid sequence of a negatively charged EBD domain, EBD(−), which is a random sequence containing disorder-promoting residues P, Q, S and E in about the following amino acid ratios: E:P:Q:S=1:2:1:2. The sequence was produced using the random sequence generator tool located at the Swiss-Prot website: au.expasy.org/tools/randseq.html.

SEQ ID NO: 26 is the amino acid sequence of a negatively charged EBD domain of SEQ ID NO: 25.

SEQ ID NO: 27 is the amino acid sequence of a neutral EBD domain, EBD(0), which is a random sequence containing disorder-promoting residues P, Q, S and G in about the following amino acid ratios: G:P:Q:S=1:2:1:2. The sequence was produced using the random sequence generator tool located at the Swiss-Prot website: au.expasy.org/tools/randseq.html.

SEQ ID NO: 28 is the amino acid sequence of a neutral EBD domain of SEQ ID NO: 27.

SEQ ID NO: 29 is a polynucleotide sequence encoding the amino acid sequence of SEQ ID NO: 23. The sequence was produced using the reverse translation tool located at: www.vivo.colostate.edu/molkit/rtranslate/index.html.

SEQ ID NO: 30 is a polynucleotide sequence encoding the amino acid sequence of SEQ ID NO: 24. The sequence was produced using the reverse translation tool located at: www.vivo.colostate.edu/molkit/rtranslate/index.html.

SEQ ID NO: 31 is a polynucleotide sequence encoding the amino acid sequence of SEQ ID NO: 25. The sequence was produced using the reverse translation tool located at: www.vivo.colostate.edu/molkit/rtranslate/index.html.

SEQ ID NO: 32 is a polynucleotide sequence encoding the amino acid sequence of SEQ ID NO: 26. The sequence was produced using the reverse translation tool located at: www.vivo.colostate.edu/molkit/rtranslate/index.html.

SEQ ID NO: 33 is a polynucleotide sequence encoding the amino acid sequence of SEQ ID NO: 27. The sequence was produced using the reverse translation tool located at: www.vivo.colostate.edu/molkit/rtranslate/index.html.

SEQ ID NO: 34 is a polynucleotide sequence encoding the amino acid sequence of SEQ ID NO: 28. The sequence was produced using the reverse translation tool located at: www.vivo.colostate.edu/molkit/rtranslate/index.html.

SEQ ID NO: 35 is the polypeptide sequence of an artificial EBD designed to contain amino acids X:P:Q:S in the following ratio 1:2:1:2, where X is a variable position to generate positive, negative or neutral bristles, and corresponds to one of K, E, or G respectively.

SEQ ID NO: 36 is the polynucleotide sequence of the pAquoProt expression vector backbone. The pAquoProt vector was built by adding the F1 origin of replication, LacI gene, and customized expression/cloning region to an existing pUC19 plasmid.

SEQ ID NO: 37 is the polynucleotide sequence of the pAquoKin expression vector backbone. The pAquoProt vector was built by adding the F1 origin of replication, LacI gene, and customized expression/cloning region to an existing pUC19 plasmid.

SEQ ID NO: 38 is the amino acid sequence of a negatively charged EBD domain, which is a random sequence containing disorder-promoting residues P, Q, S and E in about the following amino acid ratios: E:P:Q:S=1:2:1:1. The sequence was produced using the random sequence generator tool located at the Swiss-Prot website: au.expasy.org/tools/randseq.html.

SEQ ID NO: 39 is the amino acid sequence of a negatively charged EBD domain, which is a random sequence containing disorder-promoting residues P, Q, S and E in about the following amino acid ratios: E:P:Q:S=1:4:1:1. The sequence was produced using the random sequence generator tool located at the Swiss-Prot website: au.expasy.org/tools/randseq.html.

SEQ ID NO: 40 is the amino acid sequence of a negatively charged EBD domain, which is a random sequence containing disorder-promoting residues P, Q, S and E in about the following amino acid ratios: E:P:Q:S=2:2:1:1. The sequence was produced using the random sequence generator tool located at the Swiss-Prot website: au.expasy.org/tools/randseq.html.

SEQ ID NO: 41 is the amino acid sequence of a negatively charged EBD domain, which is a random sequence containing disorder-promoting residues P, Q, G and E in about the following amino acid ratios: E:P:Q:G=1:4:1:1. The sequence was produced using the random sequence generator tool located at the Swiss-Prot website: au.expasy.org/tools/randseq.html.

SEQ ID NO: 42 is the amino acid sequence of a negatively charged EBD domain, which is a random sequence containing disorder-promoting residues P, Q, G and E in about the following amino acid ratios: E:P:Q:G=2:2:1:1. The sequence was produced using the random sequence generator tool located at the Swiss-Prot website: au.expasy.org/tools/randseq.html.

SEQ ID NO: 43 is the amino acid sequence of a negatively charged EBD domain, which is a random sequence containing disorder-promoting residues P, Q, G and E in about the following amino acid ratios: E:P:Q:G=3:2:1:1. The sequence was produced using the random sequence generator tool located at the Swiss-Prot website: au.expasy.org/tools/randseq.html.

SEQ ID NO: 44 is the amino acid sequence of a negatively charged EBD domain, which is a random sequence containing disorder-promoting residues P, Q, S, G, D and E in about the following amino acid ratios: D:E:P:Q:S:G=1:2:3:1:2:1. The sequence was produced using the random sequence generator tool located at the Swiss-Prot website: au.expasy.org/tools/randseq.html.

SEQ ID NO: 45 is the amino acid sequence of a negatively charged EBD domain, in which certain amino acids in SEQ ID NO: 44 were substituted with the hydrophobic amino acids I, L, M, F, and V. The hydrophobic amino acid substitutions comprise approximately 12% of the residues.

SEQ ID NO: 46 is a polynucleotide sequence encoding the amino acid sequence of SEQ ID NO: 38. The sequence was produced using the reverse translation tool located at: www.vivo.colostate.edu/molkit/rtranslate/index.html.

SEQ ID NO: 47 is a polynucleotide sequence encoding the amino acid sequence of SEQ ID NO: 39. The sequence was produced using the reverse translation tool located at: www.vivo.colostate.edu/molkit/rtranslate/index.html.

SEQ ID NO: 48 is a polynucleotide sequence encoding the amino acid sequence of SEQ ID NO: 40. The sequence was produced using the reverse translation tool located at: www.vivo.colostate.edu/molkit/rtranslate/index.html.

SEQ ID NO: 49 is a polynucleotide sequence encoding the amino acid sequence of SEQ ID NO: 41. The sequence was produced using the reverse translation tool located at: www.vivo.colostate.edu/molkit/rtranslate/index.html.

SEQ ID NO: 50 is a polynucleotide sequence encoding the amino acid sequence of SEQ ID NO: 42. The sequence was produced using the reverse translation tool located at: www.vivo.colostate.edu/molkit/rtranslate/index.html.

SEQ ID NO: 51 is a polynucleotide sequence encoding the amino acid sequence of SEQ ID NO: 43. The sequence was produced using the reverse translation tool located at: www.vivo.colostate.edu/molkit/rtranslate/index.html.

SEQ ID NO: 52 is a polynucleotide sequence encoding the amino acid sequence of SEQ ID NO: 44. The sequence was produced using the reverse translation tool located at: www.vivo.colostate.edu/molkit/rtranslate/index.html.

SEQ ID NO: 53 is a polynucleotide sequence encoding the amino acid sequence of SEQ ID NO: 45. The sequence was produced using the reverse translation tool located at: www.vivo.colostate.edu/molkit/rtranslate/index.html.

DETAILED DESCRIPTION OF THE INVENTION

Artificial EBD fusion polynucleotides, polypeptides and vectors are provided by the present invention which offers significant advantages in the context of recombinant polypeptide production, particularly where it is desired to achieve, for example, improved solubility, improved yield, improved folding and/or reduced aggregation of a recombinant polypeptide of interest.

Artificial EBDs take advantage of the unique features of different classes of amino acids that are found within regions of order and disorder. The amino acids compositions of disordered and ordered regions in proteins are significantly different. Based on the analysis of intrinsically disordered proteins and regions within proteins, amino acids can be grouped into 3 categories: 1) order-promoting, 2) disorder-promoting, and 3) neutral (Dunker et al., Intrinsically disordered protein. *J Mol Graph Model,* 2001. 19(1): p. 26-59).

The advantages of the present invention are made possible by proper selection of disorder-promoting residues, order-promoting residues and/or neutral residues, as well as their respective proportions, within an artificial EBD sequence, as described herein. Proteins which have proven difficult to produce by conventional recombinant methodologies can be successfully produced when employing the artificial EBD sequences of the present invention.

The term "disorder-promoting amino acid residue" means an amino acid residue that promotes the disorder of stable tertiary and/or secondary structure within a polypeptide in solution. Disorder-promoting residues include D, M, K, R, S, Q, P, E and G.

The term "order-promoting amino acid residue" means an amino acid residue that promotes stable tertiary and/or secondary structure within a polypeptide in solution. Order-promoting amino acid residues include C, W, Y, I, F, V, L, H, T and N.

Neutral amino acid residues include A. The class of neutral amino acids can also include H, T, N, G, and D, as these amino acids tend to influence the tertiary and/or secondary structures within a protein or polypeptide to a relatively lesser extent then the other amino acids residues in above-defined classes (FIG. 1).

The phrases "about the ratio" and "in about the following amino acid ratio" means a group of amino acids as described herein, wherein the range "about" is determined by the actual ratio of said group of amino acids, first normalized by the lowest integer value within said group and then rounded to the nearest integer value. The resulting ratio if identical to the claimed ratio is then said to be "about" the claimed ratio of the group of amino acids. For example, consider a 100 AA EBD sequence of a fusion polypeptide which has the actual amino acid ratio of X:P:Q:S of 30:26:14:32. The actual amino acid ratio is normalized to 14, the lowest integer value, to yield a ratio of 2.1:1.9:1:2.3, which rounded to the nearest integer value is the ratio 2:2:1:2. Thus, a 100 AA EBD domain with an actual ratio of 30:26:14:32 has about the following amino acid ratio X:P:Q:S=2:2:1:2.

As used herein, the terms "polypeptide" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. Polypeptides of the invention may be prepared using any of a variety of well known recombinant and/or synthetic techniques, illustrative examples of which are further discussed below.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); Oligonucleotide Synthesis (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); *A Practical Guide to Molecular Cloning* (B. Perbal, ed., 1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Fusion polypeptides comprising an EBD sequence and a heterologous polypeptide exhibit improved solubility relative to the corresponding heterologous polypeptide in the absence of the EBD sequence. In one embodiment, for example, the fusion polypeptide has at least 5% increased solubility relative to the heterologous polypeptide sequence alone. In another related embodiment, the fusion polypeptide has at least 25% increased solubility relative to the heterologous polypeptide sequence. In yet another related embodiment, the fusion polypeptide has at least 50% increased solubility relative to the heterologous polypeptide sequence.

The extent of improved solubility provided by an EBD sequence described herein can be determined using any of a number of available approaches (see for example, Kapust, R. B. and D. S. Waugh, *Escherichia coli* maltose-binding protein is uncommonly effective at promoting the solubility of polypeptides to which it is fused. Protein Sci, 1999. 8:1668-74; Fox, J. D., et al., Maltodextrin-binding proteins from diverse bacteria and archaea are potent solubility enhancers. *FEBS Lett,* 2003. 537:53-7; Dyson M R, Shadbolt S P, Vincent K J, Perera R L, McCafferty J. Production of soluble mammalian proteins in *Escherichia coli*: identification of protein features that correlate with successful expression. *BMC Biotechnol.* 2004 Dec. 14; 4(1):32).

Cells from single, drug resistant colony of *E. coli* overproducing the fusion polypeptide are grown to saturation in LB broth (Miller J H. 1972. *Experiments in molecular genetics*. Cold Spring Harbor, N.Y.: Cold Spring Harbor Press. p 433) supplemented with 100 mg/mL ampicillin and 30 mg/mL chloramphenicol at 37° C. The saturated cultures are diluted 50-fold in the same medium and grown in shake-flasks to mid-log phase ($A_{600}$~0.5-0.7), at which time IPTG is added to a final concentration of 1 mM. After 3 h, the cells are recovered by centrifugation. The cell pellets are resuspended in 0.1 culture volumes of lysis buffer (50 mM Tris-HCl (pH 8.0), 150 mM NaCl, 1 mM EDTA), and disrupted by sonication. A total protein sample is collected from the cell suspension after sonication, and a soluble protein sample is collected from the supernatant after the insoluble debris is pelleted by centrifugation (20,000×g). These samples are subjected to SDS-PAGE and proteins are visualized by staining with Coomassie Brilliant Blue. At least three independent experiments are typically performed to obtain numerical estimates of the solubility of each fusion protein in *E. coli.* Coomassie-stained gels will be scanned with a gel-scanning densitometer and the pixel densities of the bands corresponding to the fusion proteins are obtained directly by volumetric integration. In each lane, the collective density of all *E. coli* proteins that are larger than the largest fusion protein are also determined by volumetric integration and used to normalize the values in each lane relative to the others. The percent solubility of each fusion protein is calculated by dividing the amount of soluble fusion protein by the total amount of fusion protein in the cells, after first subtracting the normalized background values obtained from negative control lanes (cells containing no expression vector). Descriptive statistical data (e.g., the mean and standard deviation) is then generated using standard methods.

The presence of an EBD sequence in fusion polypeptides of the present invention can also serve to reduce the extent of aggregation of a heterologous polypeptide sequence. In one embodiment, for example, the fusion polypeptide exhibits at least 10% reduced aggregation relative to the heterologous polypeptide. In another embodiment, the fusion polypeptide has at least 25% reduced aggregation relative to the heterologous polypeptide.

The extent of reduced aggregation provided by the fusion polypeptides of the present invention can be determined using any of a number of available techniques (see for example, Kapust, R. B. and D. S. Waugh, *Escherichia coli* maltose-binding protein is uncommonly effective at promoting the solubility of polypeptides to which it is fused. *Protein Sci,* 1999. 8:1668-74; Fox, J. D., et al., Maltodextrin-binding proteins from diverse bacteria and archaea are potent solubility enhancers. *FEBS Lett,* 2003. 537:53-7).

Cells from single, drug resistant colony of *E. coli* overproducing the fusion polypeptide are grown to saturation in LB broth (Miller J H. 1972. *Experiments in molecular genetics*. Cold Spring Harbor, N.Y.: Cold Spring Harbor Press. p 433) supplemented with 100 mg/mL ampicillin and 30 mg/mL chloramphenicol at 37° C. The saturated cultures are diluted 50-fold in the same medium and grown in shake-flasks to mid-log phase ($A_{600}$~0.5-0.7), at which time IPTG is added to a final concentration of 1 mM. After 3 h, the cells are recovered by centrifugation. The cell pellets are resuspended in 0.1 culture volumes of lysis buffer (50 mM Tris-HCl (pH 8.0), 150 mM NaCl, 1 mM EDTA), and disrupted by sonication. A total protein sample is collected from the cell suspension after sonication, and an insoluble protein sample is collected from the pellet after the centrifugation (20,000×g). These samples are subjected to SDS-PAGE and proteins are visualized by staining with Coomassie Brilliant Blue. At least three independent experiments are typically performed to obtain numerical estimates of the solubility of each fusion protein in *E. coli*. Coomassie-stained gels are scanned with a gel-scanning densitometer and the pixel densities of the bands corresponding to the fusion proteins are obtained directly by volumetric integration. In each lane, the collective density of all insoluble *E. coli* proteins that are larger than the largest fusion protein is also determined by volumetric integration and used to normalize the values in each lane relative to the others. The percent insolubility of each fusion protein is calculated by dividing the amount of insoluble fusion protein by the total amount of fusion protein in the cells, after first subtracting the normalized background values obtained from negative control lanes (cells containing no expression vector). Descriptive statistical data (e.g., the mean and standard deviation) is generated by standard methods.

The presence of an EBD sequence in the fusion polypeptides of the present invention can also serve to improve the folding characteristics of the fusion polypeptides relative to the corresponding heterologous polypeptide, e.g., by minimizing interference caused by interaction with other proteins.

Assays for evaluating the folding characteristics of a fusion polypeptide of the invention can be carried out using conventional techniques, such as circular dichroism spectroscopy in far ultra-violet region, circular dichroism in near ultra-violet region, nuclear magnetic resonance spectroscopy, infra-red spectroscopy, Raman spectroscopy, intrinsic fluorescence spectroscopy, extrinsic fluorescence spectroscopy, fluorescence resonance energy transfer, fluorescence anisotropy and polarization, steady-state fluorescence, time-domain fluorescence, numerous hydrodynamic techniques including gel-filtration, viscometry, small-angle X-ray scattering, small angle neutron scattering, dynamic light scattering, static light scattering, scanning microcalorimetry, and limited proteolysis.

In another embodiment of the invention, an EBD comprises an amino acid sequence that maintains a substantially random coil conformation. Whether a given amino acid sequence maintains a substantially random coil conformation can be determined by circular dichroism spectroscopy in far ultra-violet region, nuclear magnetic resonance spectroscopy, infra-red spectroscopy, Raman spectroscopy, fluorescence spectroscopy, numerous hydrodynamic techniques including gel-filtration, viscometry, small-angle X-ray scattering, small angle neutron scattering, dynamic light scattering, static light scattering, scanning microcalorimetry, and limited proteolysis.

In another embodiment of the invention, an EBD sequence comprises an amino acid sequence that is substantially mutually repulsive. This property of being mutually repulsive can be determined by simple calculations of charge distribution within the polypeptide sequence. In yet another embodiment of the invention, an EBD sequence comprises an amino acid sequence that remains in substantially constant motion, particularly in an aqueous environment. The property of being in substantially constant motion can be determined by nuclear magnetic resonance spectroscopy, small-angle X-ray scattering, small angle neutron scattering, dynamic light scattering, intrinsic fluorescence spectroscopy, extrinsic fluorescence spectroscopy, fluorescence resonance energy transfer, fluorescence anisotropy and polarization, steady-state fluorescence, time-domain fluorescence.

In another embodiment, the fusion polypeptides of the invention further comprise independent cleavable linkers, which allow an EBD sequence, for example at either the N or C terminus, to be easily cleaved from a heterologous polypeptide sequence of interest. Such cleavable linkers are known and available in the art. This embodiment thus provides improved isolation and purification of a heterologous polypeptide sequence and facilitates downstream high-throughput processes.

The present invention also provides polypeptide fragments of an EBD polypeptide sequence described herein, wherein the fragment comprises at least about 5, 10, 15, 20, 25, 50, or 100 contiguous amino acids, or more, including all intermediate lengths, of an EBD polypeptide sequence set forth herein, or those encoded by a polynucleotide sequence set forth herein. In a preferred embodiment, an EBD fragment provides similar or improved activity relative to the activity of the EBD sequence from which it is derived (wherein the activity includes, for example, one or more of improved solubility, improved folding, reduced aggregation and/or improved yield, when in fusion with a heterologous polypeptide sequence of interest.

In another aspect, the present invention provides variants of an EBD polypeptide sequence described herein. EBD polypeptide variants will typically exhibit at least about 70%, 75%, 80%, 85%, 90%, 91%, 92%, 93%, 94%, 95%, 96%, 97%, 98%, or 99% or more identity (e.g., determined as described below), along its length, to an EBD polypeptide sequence set forth herein. Preferably the EBD variant provides similar or improved activity relative to the activity of the EBD sequence from which the variant was derived (wherein the activity includes one or more of improved solubility, improved folding, reduced aggregation and/or improved yield, when in fusion with a heterologous polypeptide sequence of interest.

An EBD polypeptide variant thus refers to a polypeptide that differs from an EBD polypeptide sequence disclosed herein in one or more substitutions, deletions, additions and/or insertions. Such variants may be naturally occurring or may be synthetically generated, for example, by modifying one or more of the EBD polypeptide sequences of the invention and evaluating their activity as described herein and/or using any of a number of techniques well known in the art.

In certain instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the EBD polynucleotides and polypeptides of the present invention and still obtain a functional molecule that encodes a variant or derivative polypeptide with desirable activity. When it is desired to alter the amino acid sequence of an EBD polypeptide to create an equivalent or an improved EBD variant or EBD fragment, one skilled in the art can readily change one or more of the codons of the encoding DNA sequence, for example according to Table 1.

For example, certain amino acids may be substituted for other amino acids in a protein structure without appreciable loss of desired activity. It is thus contemplated that various changes may be made in the EBD polypeptide sequences of the invention, or corresponding DNA sequences which encode said EBD polypeptide sequences, without appreciable loss of their desired activity.

TABLE 1

| Amino Acids | | | Codons | | | | | |
|---|---|---|---|---|---|---|---|---|
| Alanine | Ala | A | GCA | GCC | GCG | | GCU | |
| Cysteine | Cys | C | UGC | | | UGU | | |
| Aspartic acid | Asp | D | GAC | | | GAU | | |
| Glutamic acid | Glu | E | GAA | | | GAG | | |
| Phenylalanine | Phe | F | UUC | | | UUU | | |
| Glycine | Gly | G | GGA | GGC | GGG | | GGU | |
| Histidine | His | H | CAC | | | CAU | | |
| Isoleucine | Ile | I | AUA | AUC | | AUU | | |
| Lysine | Lys | K | AAA | | | AAG | | |
| Leucine | Leu | L | UUA | UUG | CUA | CUC | CUG | CUU |
| Methionine | Met | M | | | AUG | | | |
| Asparagine | Asn | N | AAC | | | AAU | | |
| Proline | Pro | P | CCA | CCC | CCG | | CCU | |
| Glutamine | Gln | Q | CAA | | | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | | ACU | |
| Valine | Val | V | GUA | GUC | GUG | | GUU | |
| Tryptophan | Trp | W | | | UGG | | | |
| Tyrosine | Tyr | Y | UAC | | | UAU | | |

In making such changes, the hydropathic index of amino acids may also be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn has potential bearing on the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Therefore, according to certain embodiments, amino acids within an EBD sequence of the invention may be substituted by other amino acids having a similar hydropathic index or score. Preferably, any such changes result in an EBD sequence with a similar level of activity as the unmodified EBD sequence. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Thus, an amino acid can be substituted for another having a similar hydrophilicity value and in many cases still retain a desired level of activity. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like.

Amino acid substitutions within an EBD sequence of the invention may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes.

In an illustrative embodiment, a variant EBD polypeptide differs from the corresponding unmodified EBD sequence by substitution, deletion or addition of five percent of the original amino acids or fewer. Variants may also (or alternatively) be modified by, for example, the deletion or addition of amino acids that have minimal influence on the desired activity.

A polypeptide of the invention may further comprise a signal (or leader) sequence at the N-terminal end of the polypeptide, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support.

As noted above, the present invention provides EBD polypeptide variant sequences which share some degree of sequence identity with an EBD polypeptide specifically described herein, such as those having at least 40%, 50%, 60%, 70%, 80%, 90% or 95% identity with an EBD polypeptide sequence described herein. When comparing polypeptide sequences to evaluate their extent of shared sequence identity, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., (1978) *A model of evolutionary change in proteins—Matrices for detecting distant relationships*. In Dayhoff, M. O. (ed.) *Atlas of Protein Sequence and Structure*, National Biomedical Research Foundation, Washington D.C. Vol. 5, Suppl. 3, pp. 345-358; Hein J. (1990) Unified Approach to Alignment and Phylogenes, pp. 626-645 *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS*

4:11-17 (1988); Robinson, E. D., *Comb. Theor* 11:105 (1971); Saitou, N. Nei, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In another aspect of the invention, there is provided an isolated polynucleotide sequence encoding a fusion polypeptide, the fusion polypeptide comprising at least one EBD sequence and at least one heterologous polypeptide sequence of interest. In a related aspect, the invention provides expression vectors comprising a polynucleotide encoding an EBD fusion polypeptide of the invention. In another related aspect, an expression vector of the invention comprises a polynucleotide encoding one or more EBD sequence and further comprises a multiple cloning site for the insertion of a polynucleotide encoding a heterologous polypeptide sequence of interest.

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references).

In addition, any polynucleotide of the invention, such as a polynucleotide encoding an EBD polypeptide sequence, or a vector comprising a polynucleotide encoding an EBD polypeptide sequence, may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

The terms "DNA" and "polynucleotide" are used essentially interchangeably herein to refer to a DNA molecule that has been isolated free of total genomic DNA of a particular species. "Isolated", as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will also be recognized, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

In addition to the EBD polynucleotide sequences set forth herein, the present invention also provides EBD polynucleotide variants having substantial identity to an EBD polynucleotide sequence disclosed herein, for example those comprising at least 50% sequence identity, preferably at least, 55%, 60%, 65%, 70%, 75%, 80%, 85%, 90%, 95%, 96%, 97%, 98%, or 99% or higher, sequence identity compared to an EBD polynucleotide sequence of this invention using the methods described herein, (e.g., BLAST analysis using standard parameters, as described below). One skilled in this art will recognize that these values can be appropriately adjusted to determine corresponding identity of polypeptides encoded by two polynucleotide sequences by taking into account codon degeneracy, amino acid similarity, reading frame positioning and the like.

Typically, EBD polynucleotide variants will contain one or more substitutions, additions, deletions and/or insertions, preferably such that the activity (e.g., improved folding, reduced aggregation and/or improved yield, when in fusion with a heterologous sequence of interest) of the polypeptide encoded by the variant polynucleotide is not substantially diminished relative to the corresponding unmodified polynucleotide sequence.

In additional embodiments, the present invention provides polynucleotide fragments comprising or consisting of various lengths of contiguous stretches of sequence identical to or complementary to one or more of the EBD polynucleotide sequences disclosed herein. For example, polynucleotides are provided by this invention that comprise or consist of at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of the disclosed sequence or at both ends of the disclosed sequence. Preferably, an EBD polynucleotide fragment of the invention encodes a fusion polypeptide that retains one or more desired activities, e.g., improved folding, reduced aggregation and/or improved yield, when in fusion with a heterologous sequence of interest.

The EBD polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

It will be appreciated by those of ordinary skill in the art that, as a result of the degeneracy of the genetic code, there are many nucleotide sequences that will encode a polypeptide as described herein. Some of these polynucleotides bear minimal homology to the native polynucleotide sequence. Nonetheless, polynucleotides that vary due to differences in codon usage are specifically contemplated by the present invention. Further, different alleles of an EBD polynucleotide sequence provided herein are within the scope of the present invention. Alleles are endogenous sequences that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In another embodiment of the invention, a mutagenesis approach, such as site-specific mutagenesis, may be employed for the preparation of variants and/or derivatives of the EBD polynucleotides and polypeptides described herein. By this approach, for example, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the present invention contemplates the mutagenesis of the disclosed polynucleotide sequences to alter one or more activities/properties of the encoded polypeptide. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length may be employed, in about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention wherein one or more desired activities is improved or modified.

In other embodiments of the present invention, the polynucleotide sequences provided herein can be advantageously used as probes or primers for nucleic acid hybridization. As such, it is contemplated that nucleic acid segments that comprise or consist of a sequence region of at least about a 15 nucleotide long contiguous sequence that has the same sequence as, or is complementary to, a 15 nucleotide long contiguous sequence disclosed herein may be used. Longer contiguous identical or complementary sequences, e.g., those of about 20, 30, 40, 50, 100, 200, 500, 1000 (including all intermediate lengths) and even up to full length sequences will also be of use in certain embodiments.

Many template dependent processes are available to amplify a target sequence of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

As noted, the EBD fusion polynucleotides, polypeptides and vectors of the present invention are advantageous in the context of recombinant polypeptide production, particularly where it is desired to achieve, for example, improved solubility, improved yield, improved folding and/or reduced aggregation of a heterologous polypeptide to which an EBD polypeptide sequence has been operably fused. Therefore, another aspect of the invention provides methods for producing a recombinant protein, for example by introducing into a host cell an expression vector comprising a polynucleotide sequence encoding a fusion polypeptide as described herein, e.g., a fusion polypeptide comprising at least one EBD sequence and at least one heterologous polypeptide sequence of interest; and expressing the fusion polypeptide in the host cell. In a related embodiment, the method further comprises the step of isolating the fusion polypeptide from the host cell. In another embodiment, the method further comprises the step of removing an EBD sequence from the fusion polypeptide before or after isolating the fusion polypeptide from the host cell.

For recombinant production of a fusion polypeptide of the invention, DNA sequences encoding the polypeptide components of a fusion polypeptide (e.g., one or more EBD sequences and a heterologous polypeptide sequence of interest) may be assembled using conventional methodologies. In one example, the components may be assembled separately and ligated into an appropriate expression vector. For example, the 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the activities of both component polypeptides.

A peptide linker sequence may be employed to separate an EBD polypeptide sequence from a heterologous polypeptide sequence by some defined distance, for example a distance sufficient to ensure that the advantages of the invention are achieved, e.g., advantages such as improved folding, reduced aggregation and/or improved yield. Such a peptide linker sequence may be incorporated into the fusion polypeptide using standard techniques well known in the art. Suitable peptide linker sequences may be chosen based, for example, on the factors such as: (1) their ability to adopt a flexible extended conformation; and (2) their inability to adopt a secondary structure that could interfere with the activity of the EBD sequence. Illustrative peptide linker sequences, for example, may contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length, for example.

The ligated DNA sequences of a fusion polynucleotide are operably linked to suitable transcriptional and/or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The EBD and heterologous polynucleotide sequences may comprise a sequence as described herein, or may comprise a sequence that has been modified to facilitate recombinant polypeptide production. As will be understood by those of skill in the art, it may be advantageous in some instances to produce polypeptide-encoding polynucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In a particular embodiment, a fusion polynucleotide is engineered to further comprise a cleavage site located between the EBD polypeptide-encoding sequence and the heterologous polypeptide sequence, so that the hetereolous polypeptide may be cleaved and purified away from an EBD polypeptide sequence at any desired stage following expression of the fusion polypeptide. Illustratively, a fusion polynucleotide of the invention may be designed to include heparin, thrombin, or factor Xa protease cleavage sites.

In order to express a desired polypeptide, the nucleotide sequences encoding the polypeptide, or functional equivalents, may be inserted into appropriate expression vector, i.e., a vector which contains the necessary elements for the transcription and translation of an inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al., (1989) Molecular Cloning, A Laboratory Manual, Cold Spring Harbor Press, Plainview, N.Y., and Ausubel, F. M. et al., (1989) Current Protocols in Molecular Biology, John Wiley & Sons, New York. N.Y.

A variety of expression vector/host systems may be utilized to contain and express polynucleotide sequences of the present invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as pBLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke, G. and S. M. Schuster (1989) *J. Biol. Chem.* 264:5503-5509); and the like. Proteins made in such systems may be designed to include heparin, thrombin, or factor Xa protease cleavage sites so that the cloned polypeptide of interest can be released from the EBD moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al., (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1671-1680; Broglie, R. et al., (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al., (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the polypeptide from cell culture. The polypeptide produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to polynucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor Xa or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263-281) while the enterokinase cleavage site provides a means for purifying the desired polypeptide from the fusion protein. Further discussion of vectors which comprise fusion proteins can be found in Kroll, D. J. et al., (1993; *DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Polypeptide synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

According to another aspect, the present invention further provides binding agents, such as antibodies and antigen-binding fragments thereof, that specifically bind to an EBD sequence according to the present invention, or to a portion, variant or derivative thereof. Such binding agents may be used, for example, to detect the presence of a polypeptide comprising an EBD sequence, to facilitate purification of a polypeptide comprising an EBD sequence, and the like. An antibody, or antigen-binding fragment thereof, is said to "specifically bind" to a polypeptide if it reacts at a detectable level (within, for example, an ELISA assay) with the polypeptide, and does not react detectably with unrelated polypeptides under similar conditions.

Antibodies and other binding agents can be prepared using conventional methodologies. For example, monoclonal antibodies specific for a polypeptide of interest may be prepared using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of "humanized" antibody molecules comprising an antigen-binding site derived from a non-human immunoglobulin have been described, including chimeric antibodies having rodent V regions and their associated CDRs fused to human constant domains (Winter et al. (1991) *Nature* 349:293-299; Lobuglio et al. (1989) *Proc. Nat. Acad. Sci. USA* 86:4220-4224; Shaw et al. (1987) *J. Immunol.* 138:4534-4538; and Brown et al., (1987) *Cancer Res.* 47:3577-3583), rodent CDRs grafted into a human supporting FR prior to fusion with an appropriate human antibody constant domain (Riechmann et al. (1988) *Nature* 332:323-327; Verhoeyen et al. (1988) *Science* 239:1534-1536; and Jones et al. (1986) *Nature* 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

Yet another aspect of the invention provides kits comprising one or more compositions described herein, e.g., an isolated EBD polynucleotide, polypeptide, antibody, vector, host cell, etc. In a particular embodiment, the invention provides a kit containing an expression vector comprising a polynucleotide sequence encoding an EBD polypeptide sequence and a multiple cloning site for easily introducing into the vector a polynucleotide sequence encoding a heterologous polypeptide sequence of interest. In another embodiment, the expression vector further comprises an engineered cleavage site to facilitate separation of the EBD polypeptide sequence from the heterologous polypeptide sequence of interest following recombinant production.

The following Examples are offered by way of illustration and not by way of limitation.

EXAMPLES

Example 1

Artificial EBDs Effectively Solubilize Insoluble Proteins

To address host cell toxicity problems associated with the use of certain naturally-occurring EBD sequences in fusion with heterologous proteins, artificial sequences were designed. Our knowledge of the intrinsic protein disorder phenomenon allowed us to design highly disordered artificial EBD sequences with desirable charge properties. Further, the likelihood that a completely artificial sequence would possess cytotoxicity due to the specific interaction with cellular components seemed to be minimal.

Designing the Artificial Entropic Bristles

In order to serve as an artificial EBD, a polypeptide chain should be highly flexible and disordered. Statistical comparisons of amino acid compositions indicated that disordered and ordered regions in proteins are different to a significant degree. Based on the analysis of intrinsically disordered (ID) proteins and disordered regions within proteins, amino acid residues were categorized as (1) order-promoting, (2) disorder-promoting and (3) neutral (Dunker, et al., *J Mol Graph Model,* 2001. 19(1): p. 26-59). FIG. 1 presents relative amino acid compositions of ID regions available in the DisProt database (Sickmeier et al. *Bioinformatics,* 2005. 21(1): p. 137-40). The amino acid compositions were compared using a profiling approach (Dunker, et al., *J Mol Graph Model,* 2001. 19(1): p. 26-59). FIG. 1 shows that certain order-promoting residues include C, W, Y, I, F, V, L, H, T, and N, disorder-promoting residues include D, M, K, R, S, Q, P, E, and G, while neutral residues include A. It is notable that H, T, N, G, and D are borderline by the 0.1 fractional difference criterion, and so these residues could also be considered neutral in certain contexts.

The right-most bars representing the most disorder-promoting residues (E, P, Q, S, and K) together with the disorder-neutral residue G were chosen as basis for the de novo design of artificial EBDs. An artificial EBD was designed to contain the chosen residues in about the following amino acid ratios: X:P:Q:S=1:2:1:2, where X is a variable position to generate positive, negative or neutral bristles, and corresponds to one of K, E, or G, respectively.

The 1:2:1:2 proportions for X:P:Q:S were based on the following observations. Proline disrupts secondary structure (except for polyproline II helix) and contains hydrophobic surfaces for weak binding to possible aggregation patches, so a high proportion of P was chosen. PolyQ spontaneously aggregates, so a low proportion of Q was chosen to avoid aggregation-prone continuous stretches of Q. The side chain of serine is hydrophilic, but its ability to hydrogen bond with the backbone leads to very high conformational variability, so a high proportion of S was chosen. Since structured regions of proteins never contain long regions of very low complexity (Romero et al., *Proteins.* 2001. 42(1): p. 38-48), a small number of different amino acids (e.g., a low complexity bristle) reduces the chance of accidental formation of stable tertiary structure by stable interactions with other parts of the protein.

Based on these prerequisites, a 100 residue long random sequence was generated. The resulting sequence is shown in FIG. 2. Then, a fragment of this sequence, underlined sequence in FIG. 2A, was chosen to serve as the de novo EBD. This general sequence was used to generate EBDs that were positive (EB+), negative (EB−) and neutral (EB0) (FIG. 2B).

Target Protein Selection

Thirteen proteins previously shown to be insoluble without fusions or shown to be insoluble even when fused to maltose-binding protein (MBP) were selected (Kapust et al., *Protein Sci,* 1999. 8(8): p. 1668-74; Kataeva et al., *J Proteome Res,* 2005. 4(6): p. 1942-51). Nine of these proteins were insoluble even at 30° C. of induction (Kataeva et al., *J Proteome Res,* 2005. 4(6): p. 1942-51). The proteins had molecular masses from 8.4 to 28.3 kDa; isoelectric points (pI) from 3.55 to 10.9, and net charges from +20 to −17. These proteins and some of their properties are listed in Table 2.

Cloning Methods

To attach EBDs to N-termini of target proteins, the Gateway Cloning Technique (Invitrogen) based on a specific recombination of homologous DNA sequences was used. For polymerase chain reaction (PCR) accuracy, the high fidelity and specificity AccuPrime Pfx DNA polymerase (Invitrogen) was used (Takagi et al., *Appl Environ Microbiol,* 1997. 63(11): p. 4504-10). Primers were designed and optimized using XPression Primer 3.0 software. PCR products were purified using Wizard SV Gel and PCR Clean-Up System (Promega) or by mini-dialysis using Millipore. To generate entry clones, pDONR221 (Invitrogen) was used as an entry vector. All entry clones have been verified by sequencing. For the creation of expression clones, pDEST-42 destination vector (Gateway) was used. A point point mutation in pDEST-42 was done using QuickChange II XL Site-Directed Mutagenesis Kit (Stratagene). One Shot TOP10 and BL21 Star (DE3) One Shot competent cells (Invitrogen) were commonly used for transformation with BP and LR reactions, respectively. Plasmid DNAs were purified using Wizard Plus SV Minipreps DNA Purification System (Promega). To create maltose-binding protein (MBP) fusions the target genes were amplified by PCR using forward and reverse primers flanked by attB1 and attB2 sites, respectively, and cloned into entry vector as described above. To create expression clones, pDEST-544 vector (Invitrogen) was used. Proteins expressed from this vector had an MBP at their N-termini.

Cell Growth and Lysis

Cultures were grown in an LB medium supplied with 100 μg/mL ampicillin at 37° C. overnight and used next morning to start new 1 ml cultures. The tubes were incubated with shaking at 37° C. for 4 hours. Then IPTG was added to a final concentration of 1 mM and the tubes were shaken for additional 4 h at either 37° C. or 30° C. The cells were collected by centrifugation and lysed chemically using the combination of mild nonionic detergent and a lysozyme (B-PER Reagent, Thermo). The suspensions were stirred for 30 min at room temperature. The lysed solution was designated as a "whole fraction". The "soluble fraction" was obtained by removal of insoluble fraction by centrifugation. The whole and the soluble fractions were used for the detection of protein expression and solubility, respectively.

Design of Cloning Strategy

Figure 3:
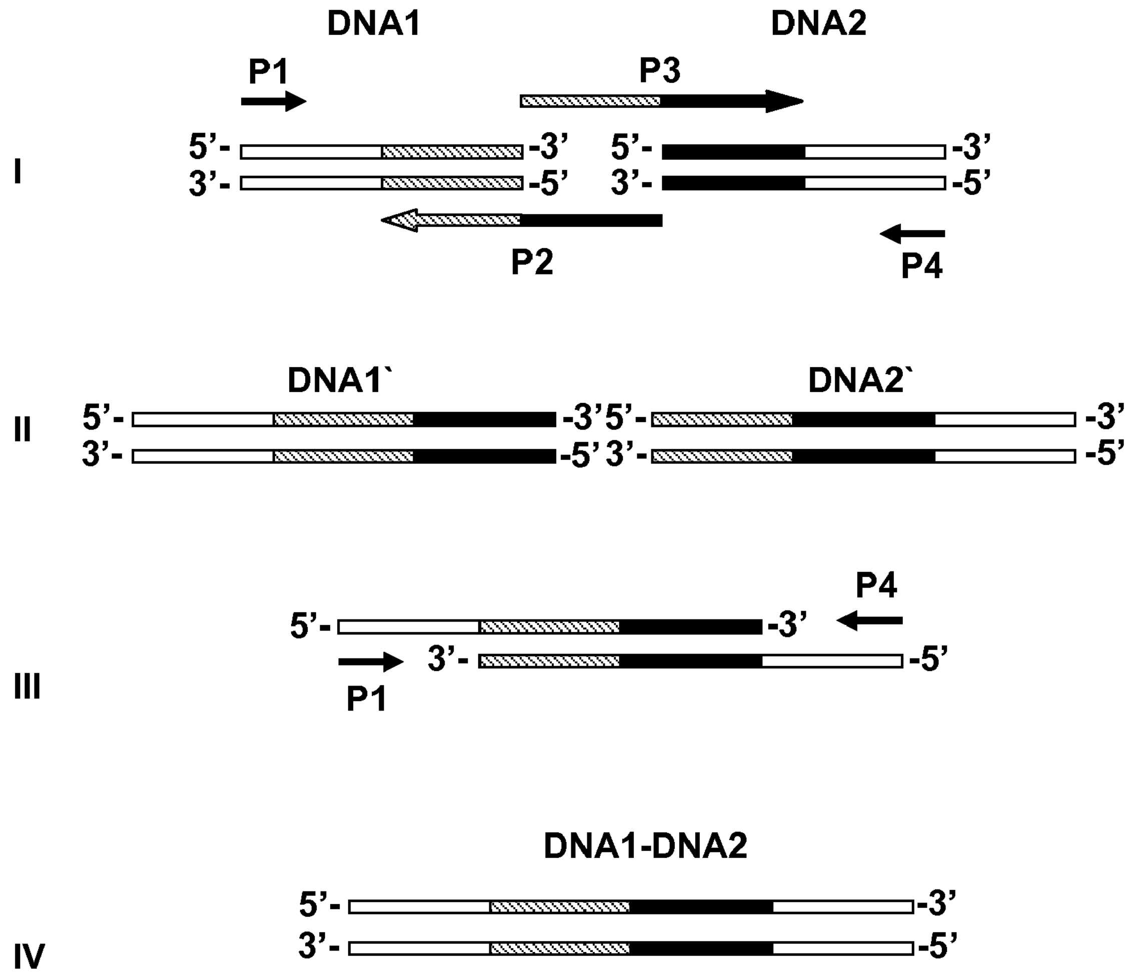
FIG. 3. Ligation of two DNA sequences via PCR. I, amplification of DNA1 and DNA2 sequences using reversed DNA1 overlapping primer P2 and DNA2 forward overlapping primer P3. II, Products of the PCR1 bearing overlapping fragments. III, PCR2 annealing step. IV. Final product composed of DNA1+DNA2.

To avoid translation of the eleven amino acid residues attB1 recombination site, (i.e. for native protein expression), its start codon (ATG) was mutated to ATA encoding isoleucine. For the same reason, Shine-Dalgarno (SD) sequence followed by a linker (L) and a start codon were inserted between the attB1 site and the entropic bristle sequence. Original reversed transcripts of 30 amino acid residues of the designed artificial EBDs were 90 bases long. After addition of a 5'-fragment (the attB1 site, the Shine Dalgarno, the linker, and the start codon), the resulted DNA fragment to be synthesized was over 140 bases long. To minimize mistakes upon synthesis of such a large DNA fragment, the putative DNA sequence of each EBD was divided into three pieces. Each piece was amplified and linked to the next one using set of PCRs and overlapping primers (see FIG. 3) (Kataeva et al., *J Proteome Res,* 2005. 4(6): p. 1942-51). After generating of EBD DNA fragments, target genes with a stop codons at their 3'-termini were amplified by PCR and linked to the 3'-terminus of each entropic bristle using the above principle (FIG. 3). Thus, each final PCR product had the following composition: attB1-SD-L-EBD-Target Gene-stop-attB2. The constructs were inserted into cloning vector. Plasmid DNAs of the clones were isolated and verified by sequencing. The "right" clones were used (1) as sources of DNA sequences encoding EBDs and (2) to make expression clones in LR reaction.

Expression and Solubility Test

To evaluate protein expression and solubility, the proteins of the whole and soluble fractions were separated by SDS-PAGE using NuPAGE 4-12% Bis-Tris Gels and the supplied reagents (Invitrogen). Gels were stained with Coomassie Blue Reagent.

Figure 4A:
FIGS. 4A and 4B. Expression and solubility of ten *C. thermocellum* proteins with N-terminal entropic bristles induced at 37° C. (4A), or MBP-fusions induced at 37° C. and 30° C. (4B). Abbreviations: T, total protein, S, soluble protein, U, uninduced cells. IDs of solubilized proteins and the corresponding EBDs are shown in italics.
Figure 4B:
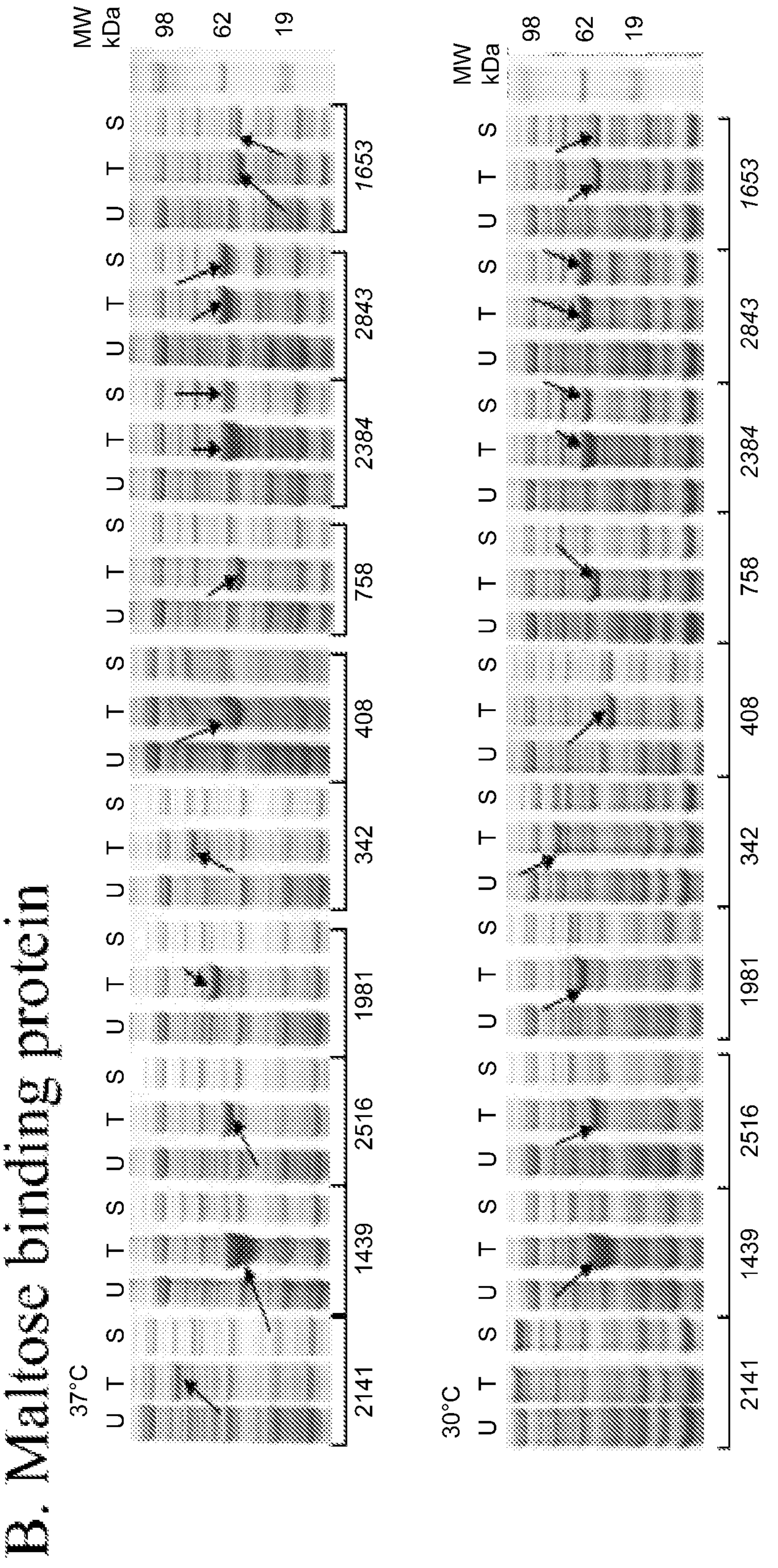

Results: Expression and Solubility of Fusion Proteins Comprising Artificial EBDs FIG. 4 and Table 2 show that artificial EBDs fused to the N-termini of target proteins was highly effective. Eleven out of thirteen insoluble proteins were solubilized by this approach (Highlighted portions of Table 2 represent the proteins that were solubilized by fusion to artificial EBDs or to MBP). The level of expression of all EBD-fusions was good. At 37° C. of induction, neutral EB0 solubilized 1 protein. Charged EB+ and EB− solubilized 5 and 6 proteins, respectively. Decreasing induction temperature improved soluble protein expression (Kataeva et al., *J Proteome Res,* 2005. 4(6): p. 1942-51). Induction at 30° C. did not change solubility of EBD0 fusions but resulted in 4 and 1 more soluble EBD+ and EBD− fusion proteins, respectively. FIG. 4 illustrates expression and solubility of 10 bacterial proteins fused either to artificial EBDs (FIG. 4A) or to maltose-binding protein (FIG. 4B), whereas Table 2 summarizes the results of the solubility studies.

TABLE 2

| | | | | 37° C. | | | | | | 30° C. | | | | | | 37° C. | | 30° C. | |
|---|---|---|---|---|---|---|---|---|---|---|---|---|---|---|---|---|---|---|---|
| | | | | $EBD_+$ | | $EBD_-$ | | $EBD_0$ | | $EBD_+$ | | $EBD_-$ | | $EBD_0$ | | MBP fusion | | | |
| Protein | MW (kDa) | pI | Charge | E | S | E | S | E | S | E | S | E | S | E | S | E | S | E | S |
| 342-Transposase_mut | 23.3 | 10.9 | 20 | 1 | 0 | 1 | 0 | 1 | 0 | 1 | 0 | 1 | 0 | 1 | 0 | 1 | 0 | 1 | 0 |
| 1981-IF-2B | 17.1 | 10 | 6.5 | 1 | 0 | 1 | 1 | 1 | 0 | 1 | 0 | 1 | 1 | 1 | 0 | 1 | 0 | 1 | 0 |
| 2516-DUF199 | 9.2 | 9.55 | 3 | 1 | 0 | 1 | 0 | 1 | 0 | 1 | 0 | 1 | 0 | 1 | 0 | 1 | 0 | 1 | 0 |
| 758-DUF111 | 12.5 | 7.3 | 5 | 1 | 1 | 1 | 1 | 1 | 0 | 1 | 1 | 1 | 1 | 1 | 0 | 1 | 0 | 1 | 0 |
| 2843-Cons_hypoth95 | 21.7 | 6.8 | 0.5 | 1 | 1 | 1 | 1 | 1 | 1 | 1 | 1 | 1 | 1 | 1 | 1 | 1 | 1 | 1 | 1 |
| 408-UbiA | 12.4 | 5.8 | -0.5 | 1 | 1 | 1 | 1 | 1 | 0 | 1 | 1 | 1 | 1 | 1 | 0 | 1 | 0 | 1 | 0 |
| 2384-HD | 21.1 | 5.5 | -1.5 | 1 | 0 | 1 | 0 | 1 | 0 | 1 | 1 | 1 | 1 | 1 | 0 | 1 | 1 | 1 | 1 |
| CATΔ9 | 26.7 | 5.2 | -14 | 1 | 0 | 1 | 1 | 0 | 0 | 1 | 1 | 1 | 0 | 0 | 0 | 1 | 0 | 1 | 0 |
| 2141-DNA_gyraseB_C | 23.2 | 5.2 | -3 | 1 | 1 | 1 | 0 | 1 | 0 | 1 | 1 | 1 | 0 | 1 | 0 | 1 | 0 | 0 | 0 |
| GFP | 28.3 | 5.13 | -14 | 1 | 0 | 1 | 0 | 1 | 0 | 1 | 1 | 1 | 1 | 0 | 0 | 1 | 1 | 1 | 1 |
| p16 | 17.7 | 4.94 | -5 | 1 | 0 | 1 | 0 | 1 | 0 | 1 | 1 | 1 | 0 | 0 | 0 | 1 | 0 | 1 | 0 |
| 1653-UPF0004 | 17.1 | 4.4 | -8.5 | 1 | 1 | 1 | 0 | 1 | 0 | 1 | 1 | 1 | 0 | 1 | 0 | 1 | 1 | 1 | 1 |
| 1439-AAA_div | 8.4 | 3.55 | -17 | 1 | 0 | 1 | 1 | 1 | 0 | 1 | 0 | 1 | 1 | 1 | 0 | 1 | 0 | 1 | 0 |

E = expression; S = solubilization; 1 = soluble; 0 = insoluble

In summary, fusion of MBP significantly increased the solubility of just 4 of 13 proteins, at 37° C. or at 30° C., whereas the artificial EBD of the present invention increased the solubility for 11 of the 13 previously insoluble proteins.

Example 2

Development of Novel EBD-Fusion Expression Vectors

A. Design of the AquoProt/AquoKin Vector Backbone

This example describes the cloning of the generic 4.2 kilobase pAquoProt and pAquoKin vector backbone. pUC19 is the source for the dsDNA polypeptide used to build the AquoProt and AquoKin vectors. Functional features already present in the pUC19 vector include the DNA sequence encoding ampicillin resistance and the *E. coli* high copy origin. Additional features in the hybrid plasmid include an f1 origin, allowing for in vitro translation system compatibility; a novel cloning/expression cassette allowing for expression of a unique synthetic polypeptide fusion to a target protein (described in detail below); and the LacI gene enabling host-independent control of the promoter controlling protein translation within the *E coli*. Digestion of the pUC19 vector with the EcoO1091 restriction enzyme allowed ligation of the f1 origene fragment in an anti-sense orientation. Next, the pUC19 vector containing antisense f1-origin was digested with NdeI and PvuII restriction enzymes to allow for the directional insertion of the synthesized cloning/expression cassette described below. This step was completed prior to the insertion of the LacI gene due to the presence of PvuII sites in the LacI gene coding sequence. The pUC19 vector containing antisense f1-origin and the cloning/expression cassette was digested using the SapI restriction site, and LacI was ligated in a sense orientation. The resultant product of these cloning steps is shown in FIG. 5, and is termed the pAquoProt vector backbone. In addition, the cloning/expression cassette can be partially replaced by digestion at SalI and NdeI sites followed by ligation of the AquoKin expression cassette to yield the pAquoKin vector backbone.

B. Design of the AquoProt Cloning/Expression Cassette.

This example describes the functional features designed into the 378 bp cloning/expression cassette that will result in the pAquoProt vector (FIG. 6). Preceding 5' to 3' from the ribosomal binding site (AAGAG, start by 100) several features were added to distinguish this cloning region from the original pUC19 vector. The DNA fragment for an N-terminal poly-histidine (His-tag) preceded by a start codon was inserted to aid purification and detection. Downstream of the His-tag a unique BstBI restriction site (start by 144) was added. Cleavage of the BstBI site was utilized for the in-frame insertion of the artificial fusion sequences described in claims 1-23). A DNA fragment encoding the recognition sequence for the endopeptidase, enterokinase, follows the BstBI and facilitates post-translational cleavage of the His-tag and fusion-peptide. This accommodates end-user needs to remove fusion polypeptides as applications dictate. Next the unique restriction sites BamHI, MfeI, EcoRV, KpnI, HindIII, Eag1, NotI, XhoI are present to assist cloning of the desired protein encoding cDNA into the vector. Finally, a C-terminal HA-tag encoding sequence (start by 224) exists so that the hybrid polypeptide can be post-translationally detected via immunochemistry. Alternatively, a stop codon can be placed as the final codon of the user-inserted protein polypeptide to prevent the addition of the post-translational addition of the HA-tag.

C. Design of the AquoKin Expression/Cloning Cassette

This example describes the functional features designed into the 381 bp cloning/expression cassette that distinguish the pAquokin vector (FIG. 7) from the pAquoProt vector (FIG. 6). First, a second solubility-aiding polypeptide described within claims X-Z will be cloned into the Eco47III site (start bp247). This restriction site is downstream of the C-terminal affinity tag, and results in the translation of a hybrid user-inserted protein with N- and C-terminal solubility-aiding EBD fusions. The vector has been designed such that these fusions can be simultaneously removed by post-translational digestion with the endopeptidase, enterokinase. To facilitate the one-step cleavage of both fusions the C-terminal affinity tag was changed from an HA-tag to the FLAG™-tag recognition sequence (U.S. Pat. No. 4,703,004) which also encodes the enterokinase consensus site. The resultant post-translational cleavage product will be the user-inserted protein sequence with a c-terminal DYKDDDK sequence that allows detection of the hybrid-polypeptide via immunochemistry.

Example 3

Artificial EBDs Effectively Solubilize Insoluble Proteins

Example 1 demonstrated that the 30 amino acid negatively charged EBDs were more effective in some instances than the neutral and positive EBDs. Therefore, additional negatively charged artificial EBDs were designed to expand the range of synthetic fusion tags. These further EBDs contain amino acids in the following approximate ratios: E:P:Q:S=1:2:1:1, E:P:Q:S=1:4:1:1, E:P:Q:S=2:2:1:1; E:P:Q:G=1:4:1:1, E:P:Q:G=2:2:1:1, E:P:Q:G=3:2:1:1, D:E:P:Q:S:G=1:2:3:1:2:1, and the D:E:P:Q:S:G=1:2:3:1:2:1 EBD sequence was also modified to contain the hydrophobic patches comprised of amino acids I, L, M, F, and V such that the EBD had approximately 12% overall hydrophobic character. Based on these amino acid ratios, 120 to 250 residue long sequences were generated computationally. The resulting polypeptide sequences are represented as SEQ ID NOs: 38-45. The EBD amino acid sequences were reverse translated into polynucleotide open reading frames and synthesized de novo (SEQ ID NOs: 46-53). The polynucleotide sequences were utilized as templates to generate novel EBDs of differing lengths and amino acid compositions. Once PCR amplified, the novel EBD coding sequences were cloned into the BstBI site of the pAquoProt vector backbone such that target proteins expressed from these plasmids have an N-terminal fusion consisting of a His-tag-EBD-EK cleavage site. Likewise, novel EBD coding sequences were cloned in various combinations into the BstBI site and Eco47III site of the pAquoKin vector backbone such that a heterologous protein expressed from this plasmid has EBDs translationally fused to both termini. A large library of expression vectors was generated by combining various EBDs into generic expression vectors to further evaluate the physical properties that are advantageous for promoting the soluble expression of a fusion partner. Table 3 lists a subset of the EBDs that have been tested and their physical properties. These EBDs span a range of lengths (24 to 250 amino acids) and exhibit a variety of amino acid compositions. Regardless of the sequence diversity between individual EBDs, all of these EBDs are low complexity, unstructured, synthetic fusion tags with negative net charges.

TABLE 3

| Seq ID (A.A. #s) | Parent A.A. ratio | EBD length | MW | Net Charge | pI |
|---|---|---|---|---|---|
| SeqID 7 (96-120) | E:P:Q:G = 1:4:1:1 | 24 | 2.5 kDa | −6 | 3.63 |
| SeqID 5 (61-120) | E:P:Q:S = 2:2:1:1 | 60 | 6.8 kDa | −24 | 3.08 |
| SeqID 9 (1-60) | E:P:Q:G = 2:2:1:1 | 60 | 6.3 kDa | −18 | 3.09 |
| SeqID 11 (1-60) | E:P:Q:G = 3:2:1:1 | 60 | 6.7 kDa | −25 | 2.97 |
| SeqID 9 (47-120) | E:P:Q:G = 2:2:1:1 | 74 | 7.9 kDa | −23 | 3.10 |
| SeqID 11 (1-120) | E:P:Q:G = 3:2:1:1 | 120 | 13.1 kDa | −51 | 2.75 |
| SeqID 13 (1-144) | D:E:P:Q:S:G = 1:2:3:1:2:1 | 144 | 15 kDa | −41 | 2.69 |
| SeqID 15 (1-250) | SeqID 13 + I, L, M, F V | 250 | 26.1 kDa | −65 | 2.48 |
| SeqID 15 (1-81) | SeqID 13 + I, L, M, F V | 81 | 8.8 kDa | −27 | 2.87 |

EBD Performance Testing

Various insoluble target proteins were selected to test the solubility-enhancing performance of the EBDs. cDNA clones for the recalcitrant proteins were either purchased from commercial sources or obtained elsewhere. The coding region for each target protein was amplified by PCR with the high fidelity AccuPrime Pfx DNA polymerase (Invitrogen) from their respective cDNA clones using primers designed for use with the In-Fusion Advantage PCR cloning kit (Clontech). The various EBD-containing expression plasmids were digested with the restriction enzyme BamHI and gel purified. The target gene PCR products were then cloned into the expression vectors at the BamHI restriction site following the standard In-fusion cloning protocol from Clontech. Following the cloning reactions chemically competent Acella cells (EdgeBio) were used for transformation.

Cell Growth and Lysis

Cultures were grown in LB medium supplied with 100 μg/mL ampicillin at 37° C. overnight. The following morning 150 μL of culture was pelleted, raised in fresh medium and added to start a 3 mL culture. The culture tubes were incubated with shaking at 37° C. for 2 hours. IPTG was then added to a final concentration of 0.2 mM and the tubes were shaken for additional 5 to 6 hrs at 25° C. The cells were collected by centrifugation and lysed chemically using the B-PER Reagent (Thermo). The suspensions were kept for 10 min at room temperature. The lysed solution was designated as a "total cell lysate". The "soluble fractions" and "pellet fractions" were separated following centrifugation. The total cell extracts, soluble fractions, and pellet fractions were used for the detection of protein expression and solubility, respectively.

Expression and Solubility Test

To evaluate protein expression and solubility, the total cell extract (T), soluble fraction (S), and pellet fraction (P) were separated by SDS-PAGE using NuPAGE 4-12% Bis-Tris Gels and the supplied reagents (Invitrogen). The proteins were transferred to PVDF membranes (Invitrogen) and probed with anti-His probe antibodies following a standard western blotting protocol. Following development, the protein gel blots were scanned with a flatbed scanner and the band intensity was compared between soluble and pellet fractions NIH ImageJ software.

Results: Comparison of Solubility-Enhancement by Artificial EBDs

In order to compare solubility-enhancement by various EBDs, proteins that were known to be insoluble were cloned into the pAquoProt series of expression vectors and overexpressed in *E. coli* under a standard set of conditions. The negative control for these experiments was the same target protein expressed from the unmodified AquoProt plasmid that did not harbor an EBD but does translationally fuse an N-terminal His-tag and EK cleavage site to the target protein. The human metalloproteinase inhibitor TIMP2 is an example of a protein that is entirely insoluble when expressed in *E. coli* with an N-terminal His-tag (FIG. 8A). However, when 5 unique EBDs ranging in length from 24 to 250 amino acids are included in the fusion tag, a portion of the recombinant TIMP2 is detectable in the soluble fraction (FIG. 8A). These results indicate that EBDs can vary greatly in composition and length and still improve the solubility of fusion partners. To evaluate the contribution of the primary amino acid sequence and overall physical properties to solubility enhancement, the TEV protease was expressed as a fusion to an N-terminal His-tag or three N-terminal EBDs that are composed of the same four amino acids and have similar physical properties but differ in primary amino acid sequence (Table 3). The solubility studies demonstrate that TEV protease solubility improves when fused to all three EBDs with similar physical characteristics but distinct primary sequences are fused to the N-terminus (FIG. 8B). We also tested whether fragments of longer EBDs could themselves be effective solubilization agents. The human B cell activating factor (TNSF13b) was translationally fused to an N terminal tag containing a 120 amino acid EBD and a tag containing a 60 amino acid fragment of the longer EBD. Both EBDs improved the solubility of TNSF13b over the His-tag control construct (FIG. 8C). In some examples a single EBD fusion was insufficient to drastically improve the solubility of a partner. Therefore, the AquoKin expression vector was prepared to facilitate the addition of EBD fusion to both termini of a target protein. To demonstrate the effectiveness of this strategy, the tyrosine kinase c-Src was expressed with an N-terminal His tag or 250 amino acid EBD (SeqID 15 (1-250). The N-terminal EBD did improve c-Src solubility somewhat (FIG. 8D). However, when a second EBD (SeqID 15 (1-81)) was added to the C-terminus of c-Src the majority of the fusion protein was detected in the soluble fraction (FIG. 8D).

Conclusions

In summary, the translational fusion of negatively charged EBDs to recalcitrant proteins can dramatically improve solubility. Moreover, the EBDs are defined not by a specific amino acid sequence but instead by their physical properties. These results clearly demonstrate that synthetic polypeptides that are disordered and charged make for effective EBDs. The EBDs can be synthesized, for example, by combining disorder-promoting amino acids in a large variety of amino acid compositions and ratios. The variety of potential EBDs is further expanded by specifically engineering variants to contain specific desired features (e.g. hydrophobic pockets like those found in chaperone proteins; SEQ ID NO 45). The effective length of EBDs is also not fixed as demonstrated by the fact that EBDs ranging in length from 24 to 250 can be effectively employed. Adding EBDs to both termini of a target protein has also been shown to improve solubility over recombinant proteins that have a single fusion tag, demonstrating yet another solubilization strategy according to the present invention.

What is claimed:

1. An isolated polynucleotide encoding an entropic bristle domain (EBD) polypeptide as set forth in SEQ ID NO selected from the group consisting of SEQ ID NO: 1, SEQ ID NO: 11, SEQ ID NO: 40, SEQ ID NO: 43 and SEQ ID NO: 44, or a fragment thereof, or a sequence having at least 90% identity to SEQ ID NO: 1, SEQ ID NO: 11, SEQ ID NO: 40, SEQ ID NO: 43 or SEQ ID NO: 44, and at least one heterologous polypeptide sequence, wherein said EBD, or said fragment thereof, or said sequence having 90% identity to SEQ ID NO: 1, SEQ ID NO: 11, SEQ ID NO: 40, SEQ ID NO: 43 or SEQ ID NO: 44 has increased solubility relative to the heterologous polypeptide sequence without said EBD, reduced aggregation relative to the heterologous polypeptide sequence without said EBD and/or improved folding relative to the heterologous polypeptide sequence without said EBD.

2. An isolated polynucleotide encoding an isolated fusion polypeptide comprising an EBD as set forth in SEQ ID NO selected from the group consisting of SEQ ID NO: 1, SEQ ID NO: 11, SEQ ID NO: 40, SEQ ID NO: 43 and SEQ ID NO: 44, or a fragment thereof, or a sequence having at least 90% identity to SEQ ID NO: 1, SEQ ID NO: 11, SEQ ID NO: 40, SEQ ID NO: 43 or SEQ ID NO: 44, and at least one heterologous polypeptide sequence, wherein the fusion polypeptide comprising said EBD, or said fragment thereof, or said sequence having 90% identity to SEQ ID NO: 1, SEQ ID NO: 11, SEQ ID NO: 40, SEQ ID NO: 43 or SEQ ID NO: 44 has increased solubility relative to the heterologous polypeptide sequence, reduced aggregation relative to the heterologous polypeptide sequence and/or improved folding relative to the heterologous polypeptide sequence.

3. An expression vector comprising the isolated polynucleotide according to claim 1.

4. The expression vector of claim 3 comprising the sequences set forth in SEQ ID NO: 36 and SEQ ID NO: 37.

5. An isolated host cell comprising the expression vector according to claim 3.

6. A kit comprising the isolated polynucleotide according to any one of claims 1 and 2, the expression vector according to any one of claim 3 or 4, or the isolated host cell according to claim 5.

7. A method for producing a recombinant protein comprising the steps of:

(a) introducing into a host cell the isolated polynucleotide according to any one of claims 1 and 2 or the expression vector according to any one of claim 3 or 4; and (b) expressing in the host cell a fusion polypeptide comprising at least one EBD sequence and at least one heterologous polypeptide sequence.

* * * * *

SEQUENCE LISTING

```
<160> NUMBER OF SEQ ID NOS: 59

<210> SEQ ID NO 1
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 1
```

-continued

```
Ser Gln Ser Pro Lys Pro Ser Ser Gln Ser Gln Ser Gln Pro Pro Ser
 1               5                  10                  15

Ser Lys Lys Ser Lys Gln Gln Gln Gln Pro Lys Ser Pro Ser Ser Ser
            20                  25                  30

Pro Gln Ser Gln Ser Pro Ser Ser Lys Pro Ser Ser Ser Ser Pro Gln
        35                  40                  45

Gln Pro Ser Lys Ser Ser Lys Ser Pro Lys Pro Pro Ser Pro Ser Pro
    50                  55                  60

Pro Pro Ser Lys Lys Pro Lys Ser Pro Ser Lys Pro Ser Pro Lys Pro
65                  70                  75                  80

Pro Ser Pro Pro Lys Ser Lys Ser Pro Lys Gln Pro Gln Ser Ser Ser
                85                  90                  95

Gln Ser Gln Ser Ser Ser Ser Lys Ser Ser Gln Pro Pro Ser Pro Pro
            100                 105                 110

Ser Ser Gln Lys Pro Ser Gln Ser Gln Ser Ser Ser Gln Pro Lys Pro
        115                 120                 125

Ser Ser Pro Lys Pro Gln Ser Ser Pro Gln Lys Gln Ser Pro Ser Gln
    130                 135                 140

Pro Lys Lys Ser Gln Lys Pro Lys Lys Gln Lys Lys Pro Gln Gln Pro
145                 150                 155                 160

Ser Ser Pro Gln Pro Lys Pro Gln Ser Gln Pro Gln Pro Pro Gln Ser
                165                 170                 175

Ser Ser Ser Lys Ser Ser Pro Gln Ser Ser Gln Gln Ser Ser Gln Ser
            180                 185                 190

Pro Pro Pro Pro Pro Pro Ser Ser Ser Ser Pro Pro Lys Ser Lys Pro
        195                 200                 205

Ser Lys Pro Gln Ser Gln Lys Pro Pro Ser Pro Ser Ser Lys Pro Lys
    210                 215                 220

Ser Lys Ser Ser Pro Gln Lys Ser Ser Ser Pro Ser Pro Lys Ser Lys
225                 230                 235                 240

Ser Pro Gln Pro Pro Lys Gln Gln Ser Pro Pro Lys Pro Pro Pro Lys
                245                 250                 255

Ser Pro Gln Pro Lys Pro Ser Pro Pro Ser Ser Pro Lys Lys Pro Lys
            260                 265                 270

Pro Pro Pro Ser Pro Lys Ser Gln Ser Ser Ser Gln Pro Ser Pro Lys
        275                 280                 285

Ser Lys Ser Gln Pro Pro Ser Ser Ser Gln Pro Ser Pro Ser Ser Ser
    290                 295                 300

Gln Gln Ser Gln Ser Pro Gln Pro Ser Ser Gln Lys Pro Pro Gln Ser
305                 310                 315                 320

Pro Ser Gln Lys Ser Lys Lys Ser Ser Pro Pro Ser Pro Pro Pro Pro
                325                 330                 335

Pro Ser Pro Pro Ser Gln Lys Gln Pro Pro Pro Pro Ser Ser Pro Lys
            340                 345                 350

Pro Pro Pro Gln Gln Ser Pro Gln Lys Ser Pro Lys Ser Pro Lys Gln
        355                 360                 365

Ser Lys Gln Ser Pro Pro Ser Gln Pro Ser Pro Pro Pro Pro Pro Ser
    370                 375                 380

Ser Pro Gln Pro Lys Pro Ser Ser Gln Pro Lys Pro Gln Ser Lys Gln
385                 390                 395                 400

Pro Gln Gln Pro Ser Lys Ser Lys Pro Pro Pro Pro Gln Ser Lys Pro
                405                 410                 415

Pro Pro Gln Ser Pro Ser Lys Pro Gln Gln Gln Pro Ser Pro Pro Lys
            420                 425                 430
```

-continued

```
Pro Pro Ser Lys Pro Lys Pro Pro Pro Gln Pro Lys Ser Lys Ser Lys
        435                 440                 445

Lys Pro Lys Gln Ser Pro Lys Ser Pro Lys Ser Pro Pro Lys Lys Ser
    450                 455                 460

Ser Gln Lys Ser Ser Ser Pro Pro Gln Ser Pro Lys Lys Gln Lys Ser
465                 470                 475                 480

Gln Ser Pro Ser Ser Ser Gln Pro Pro Lys Pro Pro Lys Pro Pro Ser
                485                 490                 495

Ser Pro Pro Pro Pro Ser Ser Ser Lys Pro Pro Ser Lys Lys Pro Gln
            500                 505                 510

Ser Ser Ser Ser Ser Pro Ser Pro Ser Gln Gln Pro Gln Pro Ser Ser
        515                 520                 525

Pro Ser Gln Pro Pro Pro Ser Ser Pro Pro Pro Pro Gln Pro Ser Gln
    530                 535                 540

Pro Pro Ser Pro Ser Ser Lys Lys Lys Gln Lys Gln Pro Gln Gln Lys
545                 550                 555                 560

Pro Pro Gln Gln Gln Ser Gln Lys Ser Lys Gln Gln Lys Gln Gln Lys
                565                 570                 575

Ser Ser Pro Pro Pro Ser Ser Ser Ser Pro Ser Lys Lys Pro Pro Pro
            580                 585                 590

Pro Ser Ser Pro Lys Ser Gln Lys Lys Lys Pro Pro Ser Gln Pro Ser
        595                 600                 605

Pro Gln Pro Ser Ser Ser Gln Ser Pro Ser Gln Gln Ser Gln Ser Lys
    610                 615                 620

Pro Ser Ser Ser Pro Gln Pro Ser Pro Gln Pro Lys Ser Gln Ser Pro
625                 630                 635                 640

Gln Ser Gln Lys Pro Ser Pro Gln Ser Ser Pro Ser Lys Ser Lys Pro
                645                 650                 655

Pro Ser Ser Ser Ser Gln Pro Lys Pro Ser Ser Pro Ser Gln Gln Pro
            660                 665                 670

Ser Gln Pro Pro Lys Ser Ser Lys Ser Lys Gln Pro Pro Pro Pro Ser
        675                 680                 685

Gln Gln Pro Ser Pro Lys Gln Ser Ser Ser Ser Pro Lys Lys Lys Pro
    690                 695                 700

Pro Gln Pro Pro Lys Lys Gln Ser Gln Gln Lys Pro Pro Pro Gln Pro
705                 710                 715                 720

Pro Pro Pro Ser Pro Pro Pro Pro Gln Gln Lys Ser Ser Ser Ser Lys
                725                 730                 735

Ser Lys Gln Lys Ser Lys Pro Ser Pro Ser Gln Ser Ser Pro Ser Pro
            740                 745                 750

Pro Ser Pro Pro Pro Pro Gln Ser Pro Lys Gln Lys Ser Ser Lys Ser
        755                 760                 765

Pro Pro Lys Gln Pro Ser Pro Pro Gln Pro Gln Ser Pro Lys Lys Gln
    770                 775                 780

Pro Gln Lys Ser Pro Pro Ser Gln Ser Pro Ser Ser Gln Ser Ser Pro
785                 790                 795                 800

Gln Pro Ser Pro Pro Pro Ser Ser Ser Gln Ser Pro Pro Pro Pro Lys
                805                 810                 815

Ser Ser Gln Ser Ser Ser Ser Ser Ser Lys Pro Pro Pro Ser Pro Lys
            820                 825                 830

Pro Pro Pro Gln Pro Ser Pro Gln Ser Ser Gln Pro Gln Lys Lys Ser
        835                 840                 845

Gln Pro Ser Ser Ser Lys Ser Pro Lys Pro Pro Pro Pro Ser Ser Lys
```

-continued

```
    850                 855                 860

Pro Pro Lys Gln Ser Ser Pro Lys Pro Ser Gln Pro Pro Ser Ser Gln
865                 870                 875                 880

Ser Lys Gln Gln Lys Gln Ser Lys Lys Lys Ser Lys Lys Lys Pro Ser
                885                 890                 895

Pro Pro Lys Lys Ser Lys Gln Pro Gln Pro Gln Ser Pro Ser Lys Ser
            900                 905                 910

Pro Lys Lys Pro Ser Ser Lys Ser Ser Lys Ser Pro Pro Lys Ser Ser
        915                 920                 925

Pro Ser Ser Pro Ser Lys Ser Pro Pro Gln Lys Pro Pro Ser Gln Lys
    930                 935                 940

Ser Ser Lys Pro Pro Pro Pro Ser Ser Ser Gln Ser Lys Pro Gln Gln
945                 950                 955                 960

Ser Pro Lys Pro Ser Lys Pro Ser Pro Pro Ser Ser Ser Ser Pro Pro
                965                 970                 975

Gln Gln Gln Ser Ser Ser Ser Lys Gln Ser Gln Ser Pro Pro Pro Pro
            980                 985                 990

Ser Ser Pro Ser Pro Ser Pro Ser
        995                 1000


<210> SEQ ID NO 2
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 2

Lys Pro Pro Pro Lys Ser Gln Lys Lys Ser Ser Lys Lys Pro Gln Gln
 1               5                  10                  15

Lys Ser Ser Lys Ser Pro Lys Ser Lys Lys Ser Ser Lys Pro Gln Lys
            20                  25                  30

Gln Lys Ser Lys Pro Pro Lys Ser Lys Ser Gln Pro Pro Lys Lys Ser
        35                  40                  45

Lys Gln Pro Ser Lys Lys Lys Lys Pro Ser Lys Lys Pro Pro Lys Ser
    50                  55                  60

Lys Gln Gln Lys Pro Lys Lys Lys Ser Pro Ser Pro Pro Pro Gln Ser
65                  70                  75                  80

Pro Ser Ser Lys Lys Lys Pro Ser Ser Ser Pro Lys Pro Lys Lys Lys
                85                  90                  95

Pro Ser Pro Pro Ser Ser Lys Ser Lys Lys Pro Lys Ser Pro Ser Pro
            100                 105                 110

Ser Lys Ser Lys Gln Gln Ser Pro Gln Lys Ser Pro Ser Pro Lys Ser
        115                 120                 125

Lys Gln Gln Ser Ser Lys Lys Ser Pro Ser Ser Ser Gln Ser Pro Pro
    130                 135                 140

Lys Ser Lys Lys Ser Ser Lys Lys Ser Ser Lys Lys Ser Pro Ser Gln
145                 150                 155                 160

Lys Lys Gln Pro Gln Pro Gln Ser Ser Pro Pro Lys Pro Pro Gln Pro
                165                 170                 175

Lys Pro Ser Pro Lys Pro Ser Ser Ser Pro Pro Pro Lys Pro Gln Gln
            180                 185                 190

Pro Pro Lys Pro Pro Ser Gln Lys Ser Pro Pro Lys Pro Lys Pro Ser
        195                 200                 205

Ser Pro Ser Gln Lys Lys Ser Ser Gln Lys Ser Lys Gln Lys Gln Pro
```

-continued

```
    210                 215                 220

Pro Pro Pro Ser Ser Lys Pro Ser Lys Ser Lys Pro Lys Lys Lys Lys
225                 230                 235                 240

Ser Ser Pro Lys Gln Pro Pro Pro Ser Pro Gln Gln Ser Ser Lys Pro
                245                 250                 255

Lys Lys Ser Ser Ser Ser Gln Lys Ser Pro Pro Gln Lys Gln Gln Lys
            260                 265                 270

Pro Ser Ser Gln Ser Ser Ser Pro Pro Pro Gln Ser Lys Ser Lys Lys
        275                 280                 285

Ser Ser Pro Lys Lys Ser Pro Pro Lys Ser Lys Pro Ser Gln Pro Gln
    290                 295                 300

Pro Ser Ser Ser Lys Pro Pro Lys Ser Lys Ser Ser Gln Gln Ser Ser
305                 310                 315                 320

Ser Ser Gln Lys Lys Pro Ser Gln Gln Gln Pro Ser Ser Pro Lys Lys
                325                 330                 335

Pro Gln Ser Pro Pro Ser Pro Pro Pro Lys Pro Pro Pro Pro Gln Ser
            340                 345                 350

Ser Ser Ser Lys Ser Pro Pro Lys Lys Ser Lys Ser Ser Pro Lys Gln
        355                 360                 365

Pro Pro Ser Pro Pro Ser Gln Ser Ser Gln Gln Ser Ser Lys Ser Ser
    370                 375                 380

Pro Ser Pro Pro Lys Lys Lys Lys Gln Pro Lys Gln Ser Lys Pro Lys
385                 390                 395                 400

Gln Gln Pro Ser Lys Gln Ser Lys Lys Lys Pro Pro Pro Gln Pro Lys
                405                 410                 415

Lys Ser Pro Gln Lys Gln Lys Ser Gln Pro Lys Lys Gln Gln Gln Lys
            420                 425                 430

Pro Ser Pro Gln Pro Lys Ser Ser Ser Lys Ser Ser Lys Pro Ser Ser
        435                 440                 445

Pro Lys Lys Lys Pro Gln Ser Ser Pro Pro Gln Gln Lys Gln Pro Ser
    450                 455                 460

Lys Pro Pro Gln Ser Pro Ser Pro Gln Lys Ser Gln Lys Ser Pro Gln
465                 470                 475                 480

Pro Pro Ser Pro Pro Lys Ser Pro Gln Pro Pro Lys Lys Ser Lys Ser
                485                 490                 495

Ser Ser Ser Lys Ser Lys Lys Ser Ser Ser Gln Lys Pro Pro Pro Gln
            500                 505                 510

Pro Lys Pro Ser Gln Pro Lys Ser Pro Pro Ser Gln Ser Lys Lys Pro
        515                 520                 525

Ser Lys Pro Pro Ser Pro Pro Ser Lys Pro Lys Gln Pro Gln Ser Pro
    530                 535                 540

Lys Ser Lys Gln Gln Ser Ser Pro Pro Ser Ser Pro Ser Lys Ser Lys
545                 550                 555                 560

Gln Lys Pro Pro Lys Gln Ser Ser Gln Pro Ser Gln Pro Pro Pro Lys
                565                 570                 575

Ser Pro Ser Pro Ser Ser Pro Lys Ser Lys Pro Lys Pro Lys Pro Ser
            580                 585                 590

Gln Ser Ser Lys Ser Ser Lys Lys Lys Pro Ser Lys Pro Pro Ser Gln
        595                 600                 605

Ser Pro Ser Gln Lys Lys Ser Ser Lys Ser Pro Pro Pro Lys Ser Lys
    610                 615                 620

Pro Pro Pro Ser Gln Ser Pro Lys Ser Lys Lys Lys Ser Pro Ser Gln
625                 630                 635                 640
```

```
Lys Ser Lys Lys Lys Lys Gln Lys Lys Pro Lys Pro Lys Pro Pro Pro
                645                 650                 655

Ser Gln Lys Lys Gln Gln Lys Ser Ser Ser Pro Pro Pro Ser Lys Lys
            660                 665                 670

Ser Ser Pro Ser Lys Ser Lys Pro Pro Ser Pro Pro Ser Lys Lys Ser
        675                 680                 685

Ser Lys Ser Pro Pro Pro Lys Lys Lys Pro Pro Pro Gln Ser Pro Ser
    690                 695                 700

Pro Lys Gln Ser Pro Gln Pro Lys Lys Pro Ser Lys Ser Ser Pro Pro
705                 710                 715                 720

Gln Gln Ser Pro Lys Lys Lys Ser Pro Lys Gln Pro Pro Ser Lys Pro
                725                 730                 735

Lys Pro Lys Pro Pro Pro Lys Gln Lys Pro Ser Ser Lys Pro Gln Lys
            740                 745                 750

Ser Ser Ser Lys Ser Lys Lys Pro Lys Pro Pro Ser Lys Gln Ser Gln
        755                 760                 765

Lys Lys Ser Lys Gln Pro Gln Ser Pro Gln Pro Ser Ser Lys Gln Lys
    770                 775                 780

Pro Lys Pro Lys Gln Ser Ser Pro Pro Lys Ser Lys Ser Lys Lys Lys
785                 790                 795                 800

Pro Pro Gln Lys Lys Pro Ser Gln Pro Lys Ser Ser Lys Pro Ser Ser
                805                 810                 815

Lys Pro Lys Lys Lys Gln Pro Pro Pro Pro Gln Pro Lys Pro Pro Gln
            820                 825                 830

Lys Lys Ser Lys Gln Ser Ser Lys Ser Pro Pro Pro Pro Ser Lys Lys
        835                 840                 845

Ser Lys Pro Ser Lys Lys Ser Gln Gln Gln Lys Ser Gln Ser Pro Ser
    850                 855                 860

Pro Lys Ser Ser Pro Pro Ser Pro Lys Pro Lys Lys Ser Pro Pro Pro
865                 870                 875                 880

Ser Ser Ser Pro Ser Ser Ser Pro Ser Ser Pro Lys Pro Pro Ser Ser
                885                 890                 895

Gln Ser Gln Lys Lys Gln Ser Pro Lys Gln Gln Pro Ser Lys Gln Lys
            900                 905                 910

Ser Ser Pro Pro Lys Lys Ser Lys Lys Pro Lys Lys Pro Pro Pro Ser
        915                 920                 925

Pro Ser Ser Lys Lys Lys Lys Pro Lys Lys Ser Lys Ser Lys Lys Pro
    930                 935                 940

Pro Ser Pro Lys Gln Lys Lys Ser Lys Gln Lys Ser Lys Pro Lys Pro
945                 950                 955                 960

Pro Lys Gln Pro Gln Ser Ser Gln Pro Pro Lys Gln Pro Lys Pro Gln
                965                 970                 975

Gln Gln Ser Gln Ser Ser Gln Pro Pro Gln Gln Ser Gln Lys Pro Gln
            980                 985                 990

Lys Pro Lys Ser Pro Gln Gln Ser
        995                 1000
```

```
<210> SEQ ID NO 3
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 3
```

-continued

```
Gln Ser Ser Ser Pro Pro Lys Ser Ser Ser Gln Ser Lys Ser Ser Ser
 1               5                  10                  15

Ser Ser Ser Ser Ser Pro Ser Pro Lys Ser Pro Ser Ser Pro Ser Lys
            20                  25                  30

Pro Pro Pro Pro Ser Lys Lys Lys Pro Lys Ser Lys Lys Lys Gln Ser
        35                  40                  45

Ser Pro Lys Ser Ser Lys Pro Lys Lys Pro Lys Gln Lys Lys Ser Pro
    50                  55                  60

Pro Pro Gln Lys Pro Lys Lys Ser Pro Ser Lys Pro Lys Ser Lys Pro
65                  70                  75                  80

Ser Ser Ser Lys Lys Lys Lys Ser Gln Gln Gln Ser Ser Gln Lys Ser
                85                  90                  95

Gln Ser Lys Gln Pro Lys Lys Pro Gln Pro Ser Pro Lys Lys Pro Lys
            100                 105                 110

Ser Pro Lys Lys Pro Pro Lys Pro Gln Pro Lys Ser Ser Pro Lys Gln
        115                 120                 125

Ser Lys Gln Lys Pro Ser Lys Lys Lys Pro Ser Ser Lys Pro Lys Ser
    130                 135                 140

Lys Ser Lys Lys Lys Ser Gln Lys Pro Lys Gln Ser Lys Lys Ser Ser
145                 150                 155                 160

Ser Lys Pro Pro Ser Lys Ser Lys Lys Lys Gln Pro Lys Pro Lys Lys
                165                 170                 175

Lys Ser Lys Ser Ser Ser Ser Lys Ser Ser Lys Ser Pro Ser Lys Ser
            180                 185                 190

Lys Ser Pro Gln Ser Ser Lys Ser Ser Pro Pro Lys Lys Pro Lys Pro
        195                 200                 205

Lys Lys Pro Lys Pro Lys Ser Ser Lys Ser Pro Lys Ser Pro Pro Lys
    210                 215                 220

Lys Lys Pro Gln Ser Gln Lys Gln Pro Lys Ser Gln Ser Pro Gln Pro
225                 230                 235                 240

Gln Lys Lys Pro Lys Gln Ser Ser Lys Gln Lys Pro Lys Ser Lys Lys
                245                 250                 255

Ser Pro Lys Lys Pro Pro Lys Lys Ser Lys Pro Lys Ser Pro Pro Pro
            260                 265                 270

Pro Lys Lys Pro Lys Pro Lys Lys Ser Ser Lys Gln Pro Lys Ser Gln
        275                 280                 285

Ser Ser Gln Lys Lys Pro Lys Pro Pro Pro Pro Ser Pro Pro Lys Gln
    290                 295                 300

Lys Pro Gln Lys Ser Ser Ser Pro Pro Lys Gln Gln Ser Lys Lys Pro
305                 310                 315                 320

Ser Pro Pro Gln Lys Pro Lys Pro Lys Ser Ser Pro Ser Pro Ser Lys
                325                 330                 335

Ser Ser Gln Ser Lys Lys Lys Lys Pro Lys Lys Pro Lys Gln Ser Pro
            340                 345                 350

Pro Gln Lys Pro Pro Ser Lys Gln Ser Pro Gln Lys Pro Lys Ser Ser
        355                 360                 365

Ser Pro Pro Lys Lys Lys Lys Ser Ser Lys Lys Gln Lys Lys Lys Gln
    370                 375                 380

Lys Lys Gln Lys Ser Ser Gln Ser Lys Pro Ser Gln Lys Pro Pro Ser
385                 390                 395                 400

Lys Pro Lys Ser Ser Ser Ser Lys Lys Lys Gln Ser Lys Lys Lys Lys
                405                 410                 415

Pro Pro Gln Lys Ser Ser Lys Lys Gln Gln Ser Pro Pro Lys Gln Ser
            420                 425                 430
```

-continued

```
Pro Lys Pro Ser Pro Lys Lys Lys Lys Pro Lys Lys Lys Gln Lys Lys
        435                 440                 445

Ser Pro Lys Gln Ser Gln Pro Lys Lys Pro Lys Pro Ser Lys Pro Gln
    450                 455                 460

Lys Ser Gln Lys Lys Ser Pro Ser Pro Lys Pro Pro Pro Gln Pro Lys
465                 470                 475                 480

Pro Gln Lys Lys Ser Pro Pro Lys Pro Lys Pro Lys Ser Pro Ser Pro
                485                 490                 495

Pro Pro Ser Gln Lys Pro Lys Lys Pro Ser Lys Pro Gln Gln Ser Pro
            500                 505                 510

Gln Lys Lys Pro Pro Pro Lys Ser Gln Lys Lys Pro Lys Pro Pro Lys
        515                 520                 525

Lys Lys Ser Lys Ser Ser Ser Pro Pro Gln Ser Lys Gln Gln Lys Lys
    530                 535                 540

Lys Lys Lys Lys Ser Pro Lys Ser Lys Lys Ser Lys Gln Pro Gln Pro
545                 550                 555                 560

Lys Gln Lys Lys Lys Ser Lys Pro Lys Ser Pro Ser Gln Lys Pro Lys
                565                 570                 575

Gln Ser Ser Ser Lys Gln Lys Lys Ser Pro Lys Pro Lys Pro Ser Pro
            580                 585                 590

Lys Ser Ser Lys Pro Gln Pro Lys Lys Lys Lys Lys Pro Ser Lys Lys
        595                 600                 605

Lys Lys Lys Lys Lys Gln Lys Pro Pro Pro Gln Ser Lys Lys Pro Lys
    610                 615                 620

Ser Pro Pro Pro Lys Pro Lys Pro Lys Ser Ser Ser Lys Lys Pro Pro
625                 630                 635                 640

Pro Lys Pro Ser Lys Pro Gln Ser Lys Lys Gln Ser Lys Ser Lys Lys
                645                 650                 655

Lys Pro Pro Lys Gln Lys Lys Lys Pro Lys Lys Ser Pro Lys Lys Lys
            660                 665                 670

Lys Lys Pro Pro Ser Ser Lys Ser Ser Pro Lys Ser Pro Pro Ser Gln
        675                 680                 685

Gln Ser Pro Pro Pro Pro Lys Gln Ser Lys Gln Pro Pro Ser Gln Ser
    690                 695                 700

Lys Lys Pro Pro Lys Pro Pro Lys Lys Lys Ser Ser Lys Lys Lys Lys
705                 710                 715                 720

Lys Ser Lys Lys Pro Gln Lys Gln Pro Lys Lys Lys Ser Ser Ser Lys
                725                 730                 735

Gln Ser Lys Ser Lys Pro Pro Ser Pro Ser Gln Pro Pro Ser Pro Ser
            740                 745                 750

Lys Pro Pro Ser Pro Lys Lys Lys Ser Pro Ser Gln Ser Lys Pro Lys
        755                 760                 765

Gln Lys Ser Pro Ser Lys Ser Ser Lys Ser Lys Gln Ser Lys Pro Ser
    770                 775                 780

Lys Gln Gln Pro Lys Gln Lys Pro Gln Ser Ser Gln Lys Pro Lys Ser
785                 790                 795                 800

Pro Lys Ser Lys Lys Lys Ser Gln Lys Lys Gln Ser Ser Ser Pro Pro
                805                 810                 815

Lys Ser Lys Ser Gln Gln Pro Lys Pro Ser Gln Lys Lys Pro Pro Lys
            820                 825                 830

Gln Gln Ser Ser Lys Ser Pro Gln Lys Ser Ser Lys Gln Lys Pro Ser
        835                 840                 845

Lys Pro Ser Ser Pro Lys Pro Gln Ser Lys Gln Ser Lys Gln Gln Lys
```

```
    850                 855                 860

Lys Lys Lys Gln Ser Lys Gln Pro Pro Lys Gln Lys Lys Pro Ser Lys
865                 870                 875                 880

Ser Lys Lys Pro Pro Pro Lys Pro Pro Pro Lys Ser Lys Pro Lys Gln
                885                 890                 895

Lys Lys Pro Gln Lys Lys Pro Lys Ser Ser Lys Lys Pro Gln Gln Pro
            900                 905                 910

Ser Pro Ser Ser Pro Ser Ser Lys Ser Ser Lys Lys Ser Lys Ser Lys
        915                 920                 925

Gln Lys Pro Pro Pro Gln Pro Pro Pro Ser Gln Lys Lys Lys Lys Pro
    930                 935                 940

Pro Pro Lys Ser Gln Lys Lys Pro Lys Lys Lys Lys Ser Ser Pro Ser
945                 950                 955                 960

Lys Lys Lys Pro Pro Lys Lys Lys Ser Pro Ser Gln Ser Ser Gln Lys
                965                 970                 975

Ser Lys Ser Ser Ser Gln Ser Pro Pro Gln Gln Pro Pro Gln Lys Pro
            980                 985                 990

Lys Lys Ser Lys Gln Lys Lys Lys
        995                 1000


<210> SEQ ID NO 4
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 4

Ser Ser Lys Pro Lys Lys Ser Pro Pro Ser Lys Lys Gln Ser Gln Ser
 1               5                  10                  15

Lys Lys Ser Lys Pro Lys Lys Lys Lys Ser Gln Lys Pro Lys Lys Ser
            20                  25                  30

Ser Pro Lys Lys Lys Ser Lys Ser Ser Lys Lys Pro Ser Pro Pro Gln
        35                  40                  45

Pro Ser Lys Gln Pro Lys Gln Gln Ser Pro Ser Lys Gln Ser Lys Ser
    50                  55                  60

Pro Lys Ser Gln Lys Pro Pro Ser Pro Pro Lys Lys Lys Gln Lys Lys
65                  70                  75                  80

Pro Ser Lys Gln Pro Lys Ser Pro Lys Pro Pro Lys Ser Lys Ser Gln
                85                  90                  95

Gln Pro Lys Pro Lys Pro Gln Gln Pro Lys Lys Lys Pro Lys Pro Ser
            100                 105                 110

Lys Pro Pro Pro Pro Ser Ser Gln Lys Gln Gln Lys Ser Lys Ser Pro
        115                 120                 125

Ser Gln Lys Lys Lys Lys Pro Ser Lys Lys Pro Lys Lys Lys Gln Pro
    130                 135                 140

Lys Gln Ser Pro Ser Ser Lys Pro Ser Ser Gln Pro Lys Gln Pro Pro
145                 150                 155                 160

Gln Lys Lys Lys Lys Pro Lys Pro Lys Lys Lys Lys Lys Gln Lys Gln
                165                 170                 175

Pro Lys Lys Pro Lys Lys Lys Lys Ser Pro Lys Lys Lys Pro Lys Pro
            180                 185                 190

Pro Lys Ser Lys Lys Lys Lys Pro Lys Ser Ser Lys Lys Ser Lys Pro
        195                 200                 205

Gln Lys Pro Ser Pro Pro Lys Ser Pro Lys Pro Lys Pro Lys Pro Lys
```

-continued

```
    210                 215                 220

Lys Lys Pro Lys Ser Lys Lys Ser Lys Ser Ser Lys Pro Lys Pro Pro
225                 230                 235                 240

Ser Lys Lys Lys Pro Pro Pro Ser Pro Pro Ser Ser Pro Lys Gln Lys
                245                 250                 255

Ser Lys Ser Pro Pro Lys Lys Lys Pro Lys Gln Lys Pro Lys Gln Lys
            260                 265                 270

Ser Lys Ser Ser Ser Pro Gln Pro Lys Pro Pro Ser Ser Pro Lys Lys
        275                 280                 285

Lys Lys Lys Gln Ser Lys Ser Lys Lys Pro Ser Lys Lys Ser Pro Pro
    290                 295                 300

Lys Lys Lys Lys Ser Gln Gln Lys Ser Ser Lys Lys Pro Lys Lys Pro
305                 310                 315                 320

Lys Lys Ser Lys Lys Ser Ser Lys Lys Lys Ser Lys Pro Gln Ser Lys
                325                 330                 335

Pro Lys Ser Ser Lys Lys Lys Lys Ser Ser Ser Lys Ser Ser Pro Lys
            340                 345                 350

Lys Pro Lys Pro Gln Gln Pro Lys Lys Lys Lys Gln Gln Lys Lys Lys
        355                 360                 365

Lys Ser Ser Lys Pro Lys Gln Lys Lys Ser Gln Lys Lys Pro Ser Lys
    370                 375                 380

Lys Lys Pro Lys Lys Pro Lys Gln Lys Lys Ser Lys Lys Ser Pro Pro
385                 390                 395                 400

Lys Lys Gln Ser Lys Gln Pro Pro Gln Lys Lys Ser Lys Lys Lys Gln
                405                 410                 415

Lys Pro Pro Ser Gln Lys Lys Ser Gln Ser Ser Pro Lys Pro Lys Pro
            420                 425                 430

Pro Gln Lys Pro Lys Lys Lys Ser Pro Lys Pro Pro Lys Lys Pro Gln
        435                 440                 445

Lys Lys Pro Lys Ser Lys Gln Ser Ser Ser Lys Pro Ser Lys Pro Pro
    450                 455                 460

Pro Pro Lys Lys Pro Pro Lys Lys Pro Lys Pro Lys Lys Lys Lys Lys
465                 470                 475                 480

Lys Ser Lys Lys Ser Ser Lys Lys Lys Lys Gln Pro Ser Pro Lys Lys
                485                 490                 495

Pro Lys Ser Lys Lys Lys Lys Lys Ser Ser Lys Pro Ser Lys Pro Ser
            500                 505                 510

Gln Gln Lys Ser Pro Lys Ser Lys Pro Ser Ser Ser Pro Gln Ser Lys
        515                 520                 525

Gln Pro Lys Gln Ser Ser Ser Ser Ser Lys Lys Pro Lys Lys Pro Pro
    530                 535                 540

Ser Lys Ser Lys Gln Pro Ser Ser Lys Ser Pro Lys Ser Pro Pro Pro
545                 550                 555                 560

Lys Pro Ser Gln Lys Pro Pro Pro Gln Lys Lys Pro Lys Gln Lys Lys
                565                 570                 575

Ser Lys Lys Pro Pro Lys Lys Lys Lys Lys Pro Gln Lys Pro Lys Lys
            580                 585                 590

Ser Ser Pro Ser Pro Pro Pro Ser Pro Lys Gln Lys Lys Lys Gln Pro
        595                 600                 605

Pro Ser Lys Gln Pro Lys Ser Lys Lys Ser Ser Gln Lys Lys Ser Ser
    610                 615                 620

Lys Ser Lys Lys Lys Lys Lys Lys Lys Pro Pro Lys Lys Ser Lys Ser
625                 630                 635                 640
```

-continued

Pro Pro Ser Gln Ser Lys Ser Lys Pro Ser Pro Pro Pro Lys Lys Pro
645 650 655

Lys Lys Gln Ser Ser Gln Gln Ser Lys Ser Gln Gln Ser Ser Lys Pro
660 665 670

Lys Pro Lys Pro Lys Lys Pro Pro Pro Lys Gln Ser Pro Ser Pro Ser
675 680 685

Ser Gln Lys Lys Lys Lys Pro Lys Ser Lys Lys Pro Ser Ser Pro Ser
690 695 700

Ser Pro Lys Ser Ser Ser Pro Ser Ser Ser Pro Ser Lys Ser Ser Lys
705 710 715 720

Gln Lys Pro Ser Ser Pro Ser Lys Pro Lys Lys Pro Lys Lys Lys Pro
725 730 735

Lys Lys Lys Pro Lys Lys Pro Lys Lys Gln Pro Lys Gln Lys Pro Lys
740 745 750

Lys Pro Pro Pro Ser Lys Lys Pro Lys Pro Pro Ser Lys Ser Gln Ser
755 760 765

Lys Lys Pro Lys Gln Lys Lys Ser Ser Pro Lys Lys Lys Lys Ser Lys
770 775 780

Lys Ser Lys Lys Ser Lys Gln Gln Lys Gln Gln Lys Lys Lys Ser Gln
785 790 795 800

Lys Lys Ser Lys Ser Ser Pro Pro Lys Ser Lys Lys Gln Lys Gln Ser
805 810 815

Lys Lys Pro Lys Gln Pro Lys Lys Lys Gln Ser Lys Ser Pro Lys Lys
820 825 830

Gln Lys Lys Pro Lys Ser Ser Pro Ser Gln Lys Gln Gln Gln Lys Lys
835 840 845

Lys Lys Gln Pro Ser Lys Ser Ser Lys Lys Pro Lys Gln Lys Lys Lys
850 855 860

Ser Lys Gln Ser Lys Pro Lys Gln Pro Lys Lys Ser Ser Pro Pro Lys
865 870 875 880

Ser Pro Ser Lys Gln Ser Lys Lys Ser Pro Ser Lys Ser Gln Lys Pro
885 890 895

Gln Ser Lys Lys Ser Pro Lys Ser Lys Lys Lys Ser Ser Lys Lys Lys
900 905 910

Lys Lys Lys Lys Lys Pro Lys Lys Pro Lys Lys Lys Pro Lys Lys Ser
915 920 925

Lys Ser Ser Ser Gln Lys Lys Ser Lys Gln Pro Lys Ser Pro Ser Gln
930 935 940

Lys Ser Ser Lys Lys Lys Lys Pro Lys Gln Ser Ser Lys Lys Lys Gln
945 950 955 960

Lys Lys Gln Lys Gln Lys Lys Lys Gln Pro Ser Ser Lys Pro Gln Pro
965 970 975

Lys Lys Lys Gln Pro Lys Lys Lys Gln Lys Lys Pro Lys Lys Lys Lys
980 985 990

Ser Pro Lys Ser Pro Lys Pro Lys
995 1000

<210> SEQ ID NO 5
<211> LENGTH: 1000
<212> TYPE: PRT
<213> ORGANISM: Artificial Sequence
<220> FEATURE:
<223> OTHER INFORMATION: Randomly generated sequence, created by ExPASy WWW server tool

<400> SEQUENCE: 5

-continued

```
Lys Lys Lys Gln Pro Lys Lys Ser Gln Gln Lys Lys Lys Lys Lys Lys
 1               5                  10                  15

Gln Ser Lys Pro Lys Gln Lys Lys Pro Pro Ser Ser Lys Pro Pro Lys
            20                  25                  30

Gln Lys Lys Lys Gln Pro Lys Lys Ser Pro Ser Lys Ser Ser Ser Lys
        35                  40                  45

Lys Lys Gln Lys Ser Pro Lys Pro Gln Lys Lys Pro Lys Lys Pro Lys
    50                  55                  60

Lys Pro Lys Lys Ser Lys Lys Gln Pro Gln Gln Pro Pro Ser Lys Pro
65                  70                  75                  80

Ser Pro Gln Ser Lys Ser Lys Gln Pro Gln Gln Lys Lys Pro Pro Lys
                85                  90                  95

Pro Lys Pro Pro Lys Lys Pro Lys Lys Lys Lys Gln Pro Ser Gln Lys
            100                 105                 110

Gln Ser Lys Pro Pro Lys Ser Gln Ser Gln Lys Lys Ser Ser Lys Gln
        115                 120                 125

Lys Ser Pro Ser Lys Pro Lys Gln Lys Ser Ser Lys Lys Lys Lys Lys
    130                 135                 140

Lys Pro Ser Ser Ser Pro Ser Lys Ser Lys Lys Lys Lys Pro Lys Ser
145                 150                 155                 160

Lys Pro Pro Lys Lys Ser Lys Pro Lys Lys Lys Lys Lys Ser Gln Ser
                165                 170                 175

Lys Lys Pro Lys Lys Lys Lys Pro Lys Gln Gln Gln Lys Pro Lys Pro
            180                 185                 190

Ser Lys Gln Gln Lys Pro Lys Pro Ser Ser Lys Lys Ser Ser Pro Lys
        195                 200                 205

Lys Lys Pro Lys Gln Lys Pro Lys Pro Gln Pro Lys Pro Lys Lys Pro
    210                 215                 220

Lys Pro Pro Lys Pro Lys Gln Lys Lys Lys Ser Lys Pro Lys Pro Lys
225                 230                 235                 240

Ser Pro Lys Lys Lys Gln Gln Gln Gln Pro Lys Pro Pro Gln Lys Ser
                245                 250                 255

Pro Lys Lys Ser Pro Pro Lys Lys Pro Lys Pro Lys Lys Ser Ser Pro
            260                 265                 270

Ser Lys Ser Pro Ser Lys Pro Lys Lys Gln Lys Pro Lys Lys Pro Ser
        275                 280                 285

Ser Gln Lys Lys Pro Lys Ser Lys Ser Pro Pro Lys Lys Gln Ser Lys
    290                 295                 300

Lys Ser Lys Ser Lys Ser Lys Lys Lys Ser Pro Ser Ser Lys Lys Ser
305                 310                 315                 320

Lys Pro Lys Lys Ser Ser Pro Lys Lys Pro Lys Ser Lys Lys Gln Ser
                325                 330                 335

Lys Ser Lys Ser Gln Lys Pro Lys Ser Lys Gln Ser Ser Pro Lys Gln
            340                 345                 350

Lys Lys Lys Ser Gln Lys Ser Lys Pro Gln Lys Ser Lys Lys Lys Ser
        355                 360                 365

Ser Pro Lys Lys Gln Lys Ser Lys Lys Lys Lys Ser Pro Lys Lys Pro
    370                 375                 380

Ser Lys Pro Pro Lys Lys Lys Pro Pro Lys Ser Lys Gln Ser Lys Lys
385                 390                 395                 400

Lys Gln Ser Pro Lys Pro Lys Pro Pro Ser Pro Ser Pro Lys Pro Lys
                405                 410                 415

Lys Lys Ser Lys Lys Lys Lys Lys Lys Gln Pro Ser Ser Lys Lys Gln
            420                 425                 430
```

-continued

```
Pro Lys Lys Pro Ser Lys Lys Lys Lys Gln Ser Pro Ser Lys Gln Pro
        435                 440                 445

Lys Ser Lys Ser Ser Lys Lys Lys Pro Pro Lys Lys Gln Pro Lys Lys
    450                 455                 460

Pro Lys Lys Lys Lys Gln Ser Ser Lys Lys Pro Lys Lys Ser Pro Gln
465                 470                 475                 480

Lys Lys Ser Lys Lys Pro Gln Ser Ser Pro Lys Lys Ser Pro Ser Lys
                485                 490                 495

Gln Pro Lys Lys Lys Lys Pro Lys Lys Pro Lys Lys Pro Lys Lys Lys
            500                 505                 510

Lys Pro Gln Ser Ser Pro Ser Lys Pro Pro Pro Lys Ser Gln Ser Lys
        515                 520                 525

Gln Lys Ser Pro Pro Lys Ser Ser Ser Lys Lys Lys Gln Lys Lys Pro
    530                 535                 540

Lys Pro Lys Lys Lys Lys Lys Pro Ser Lys Lys Lys Pro Pro Pro Ser
545                 550                 555                 560

Lys Lys Pro Lys Lys Ser Lys Lys Ser Lys Ser Lys Lys Lys Ser Lys
                565                 570                 575

Lys Lys Ser Pro Pro Lys Lys Ser Lys Lys Lys Gln Pro Lys Pro Pro
            580                 585                 590

Lys Lys Ser Lys Lys Lys Ser Ser Lys Gln Ser Lys Pro Lys Lys Ser
        595                 600                 605

Pro Lys Pro Lys Ser Lys Lys Lys Ser Lys Lys Gln Lys Ser Ser Ser
    610                 615                 620

Lys Lys Ser Pro Pro Pro Lys Ser Lys Pro Pro Lys Pro Ser Gln Pro
625                 630                 635                 640

Pro Lys Ser Lys Lys Lys Lys Pro Pro Ser Lys Lys Lys Pro Lys Lys
                645                 650                 655

Gln Lys Ser Ser Gln Lys Pro Lys Ser Ser Gln Lys Lys Lys Pro Pro
            660                 665                 670

Lys Pro Lys Lys Gln Pro Lys Ser Lys Lys Pro Lys Lys Pro Lys Lys
        675                 680                 685

Gln Gln Gln Lys Lys Pro Pro Lys Lys Lys Lys Lys Lys Lys Lys Lys
    690                 695                 700

Lys Pro Lys Pro Lys Lys Pro Pro Lys Pro Gln Ser Lys Ser Lys Lys
705                 710                 715                 720

Lys Lys Lys Ser Pro Pro Ser Pro Pro Ser Pro Lys Lys Lys Lys Lys
                725                 730                 735

Gln Lys Lys Lys Ser Lys Lys Lys Lys Pro Lys Lys Lys Pro Gln Lys
            740                 745                 750

Lys Ser Ser Lys Gln Lys Lys Lys Lys Pro Ser Ser Ser Lys Pro Lys
        755                 760                 765

Ser Gln Ser Lys Lys Ser Ser Lys Lys Pro Lys Gln Ser Lys Gln Lys
    770                 775                 780

Lys Ser Gln Ser Lys Lys Ser Ser Ser Lys Ser Lys Pro Gln Lys Lys
785                 790                 795                 800

Ser Lys Lys Lys Lys Lys Lys Lys Pro Lys Lys Lys Lys Lys Lys Lys
                805                 810                 815

Ser Lys Ser Lys Ser Ser Gln Ser Gln Lys Lys Lys Lys Lys Ser Pro
            820                 825                 830

Lys Lys Lys Lys Lys Lys Ser Lys Lys Lys Lys Ser Lys Lys Pro Pro
        835                 840                 845

Lys Pro Lys Lys Gln Ser Lys Lys Ser Lys Ser Lys Pro Pro Pro Ser
```

-continued

```
    850                 855                 860

Lys Pro Lys Ser Ser Lys Ser Lys Pro Lys Lys Pro Pro Lys Lys Lys
865                 870                 875                 880

Lys Gln Lys Lys Lys Gln Lys Ser Lys Pro Ser Lys Lys Ser Pro Ser
                885                 890                 895

Lys Pro Pro Ser Lys Pro Ser Lys Gln Lys Lys Lys Ser Gln Lys Lys
            900                 905                 910

Gln Pro Gln Pro Pro Lys Lys Gln Pro Pro Lys Ser Lys Pro Lys Pro
        915                 920                 925

Pro Lys Pro Gln Lys Ser Ser Lys Lys Lys Lys Lys Pro Ser Lys Lys
    930                 935                 940

Pro Pro Lys Lys Lys Ser Lys Lys Gln Lys Lys Lys Lys Ser Gln Ser
945                 950                 955                 960

Gln Lys Lys Ser Ser Ser Gln Lys Pro Lys Ser Ser Lys Ser Ser Gln
                965                 970                 975

Lys Lys Pro Lys Lys Lys Ser Lys Ser Ser Lys Gln Lys Ser Lys Lys
            980                 985                 990

Gln Lys Ser Lys Lys Lys Pro Lys
        995                 1000


<210> SEQ ID NO 6
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 6

Glu Glu Pro Ser Pro Ser Pro Pro Glu Ser Ser Ser Glu Pro Pro Pro
 1               5                  10                  15

Pro Pro Pro Pro Gln Pro Pro Glu Pro Pro Gln Gln Ser Glu Gln Pro
            20                  25                  30

Gln Glu Ser Ser Pro Ser Gln Ser Gln Ser Glu Pro Ser Glu Gln Gln
        35                  40                  45

Gln Glu Ser Ser Ser Ser Glu Gln Glu Ser Ser Ser Pro Pro Glu Ser
    50                  55                  60

Gln Glu Glu Pro Gln Ser Glu Gln Pro Ser Ser Pro Pro Glu Pro Gln
65                  70                  75                  80

Pro Gln Ser Gln Ser Ser Gln Pro Pro Pro Ser Glu Ser Pro Ser Gln
                85                  90                  95

Gln Ser Glu Pro Pro Pro Glu Gln Ser Gln Ser Pro Ser Ser Pro Ser
            100                 105                 110

Ser Ser Ser Gln Gln Ser Gln Pro Pro Ser Ser Glu Pro Ser Glu Pro
        115                 120                 125

Ser Pro Ser Ser Pro Gln Ser Ser Pro Ser Pro Ser Pro Gln Gln Ser
    130                 135                 140

Pro Glu Glu Ser Glu Ser Gln Pro Gln Ser Pro Ser Ser Gln Ser Pro
145                 150                 155                 160

Pro Gln Pro Pro Ser Glu Pro Ser Pro Pro Gln Ser Ser Glu Pro Pro
                165                 170                 175

Glu Pro Pro Ser Ser Glu Pro Gln Pro Ser Pro Ser Ser Pro Pro Gln
            180                 185                 190

Pro Glu Ser Pro Ser Ser Ser Ser Ser Pro Pro Ser Pro Pro Ser Pro
        195                 200                 205

Gln Glu Pro Ser Pro Glu Gln Pro Pro Pro Pro Pro Pro Pro Gln Ser
```

-continued

```
    210                 215                 220

Pro Glu Ser Pro Pro Ser Glu Pro Pro Gln Ser Pro Pro Glu Gln Glu
225                 230                 235                 240

Pro Glu Gln Pro Pro Glu Pro Glu Ser Ser Pro Pro Gln Ser Gln Ser
                245                 250                 255

Ser Glu Pro Gln Ser Gln Pro Glu Pro Gln Ser Ser Glu Gln Ser Glu
            260                 265                 270

Glu Ser Glu Ser Gln Gln Glu Pro Pro Ser Ser Pro Glu Pro Pro Ser
        275                 280                 285

Pro Glu Glu Glu Gln Pro Ser Pro Ser Ser Pro Ser Pro Pro Gln Ser
    290                 295                 300

Pro Pro Glu Pro Pro Pro Ser Ser Glu Pro Glu Ser Ser Pro Ser Ser
305                 310                 315                 320

Glu Ser Pro Ser Glu Gln Ser Pro Pro Glu Pro Ser Glu Gln Ser Ser
                325                 330                 335

Gln Ser Pro Ser Pro Ser Pro Pro Gln Gln Glu Gln Ser Pro Pro Ser
            340                 345                 350

Gln Ser Ser Pro Glu Pro Pro Ser Ser Pro Glu Pro Glu Glu Ser Pro
        355                 360                 365

Pro Pro Glu Pro Glu Ser Ser Ser Ser Pro Ser Ser Ser Gln Pro Glu
    370                 375                 380

Glu Gln Pro Ser Ser Pro Ser Pro Pro Ser Pro Pro Ser Ser Ser Gln
385                 390                 395                 400

Ser Ser Pro Ser Ser Gln Ser Pro Ser Ser Pro Glu Glu Ser Pro Ser
                405                 410                 415

Pro Pro Pro Pro Pro Glu Ser Glu Pro Ser Pro Gln Gln Pro Ser
            420                 425                 430

Pro Pro Gln Gln Glu Pro Pro Pro Ser Gln Ser Ser Pro Ser Gln Gln
        435                 440                 445

Ser Pro Pro Pro Pro Ser Ser Pro Pro Pro Ser Glu Gln Pro Pro Gln
    450                 455                 460

Glu Pro Gln Pro Pro Ser Gln Ser Ser Gln Pro Pro Glu Pro Ser Ser
465                 470                 475                 480

Gln Ser Glu Pro Ser Pro Pro Pro Gln Ser Pro Pro Gln Pro Glu Ser
                485                 490                 495

Pro Gln Pro Ser Ser Ser Ser Gln Pro Ser Ser Glu Pro Pro Ser Pro
            500                 505                 510

Ser Ser Ser Pro Pro Glu Pro Ser Pro Ser Pro Glu Gln Pro Pro Pro
        515                 520                 525

Ser Pro Ser Gln Glu Glu Pro Ser Gln Glu Pro Ser Gln Ser Glu Ser
    530                 535                 540

Ser Glu Gln Ser Gln Ser Pro Pro Ser Pro Ser Glu Ser Ser Gln Ser
545                 550                 555                 560

Pro Pro Gln Ser Ser Ser Ser Pro Gln Ser Pro Glu Pro Gln Pro Pro
                565                 570                 575

Pro Ser Glu Ser Gln Glu Ser Gln Pro Pro Pro Ser Glu Ser Gln Pro
            580                 585                 590

Ser Pro Glu Glu Ser Ser Pro Ser Ser Gln Ser Glu Gln Pro Ser Gln
        595                 600                 605

Ser Gln Glu Pro Gln Gln Ser Pro Pro Gln Pro Ser Pro Glu Gln Pro
    610                 615                 620

Glu Ser Glu Gln Glu Ser Pro Ser Pro Ser Glu Glu Ser Glu Ser Ser
625                 630                 635                 640
```

```
Ser Ser Gln Ser Pro Pro Pro Ser Pro Gln Glu Pro Ser Pro Pro Ser
                645                 650                 655

Glu Ser Gln Ser Ser Pro Ser Ser Pro Pro Gln Pro Ser Ser Ser Gln
            660                 665                 670

Glu Ser Pro Ser Ser Gln Pro Gln Pro Gln Ser Gln Ser Pro Pro Gln
        675                 680                 685

Gln Pro Gln Gln Ser Pro Pro Pro Ser Pro Pro Pro Gln Gln Ser Glu
    690                 695                 700

Glu Gln Glu Gln Glu Ser Glu Pro Gln Glu Pro Gln Pro Gln Ser Ser
705                 710                 715                 720

Pro Glu Ser Pro Ser Ser Glu Ser Glu Ser Glu Ser Ser Pro Glu Gln
                725                 730                 735

Pro Pro Gln Pro Pro Pro Ser Pro Glu Pro Pro Pro Pro Ser Pro Ser
            740                 745                 750

Pro Ser Pro Pro Ser Glu Ser Gln Pro Ser Gln Pro Gln Pro Ser Ser
        755                 760                 765

Ser Ser Glu Ser Pro Glu Glu Ser Pro Gln Pro Pro Pro Glu Glu Ser
    770                 775                 780

Pro Ser Ser Ser Ser Ser Glu Glu Pro Pro Gln Pro Glu Glu Glu Gln
785                 790                 795                 800

Ser Ser Glu Pro Ser Ser Gln Ser Pro Ser Ser Ser Pro Ser Pro Ser
                805                 810                 815

Gln Ser Glu Ser Gln Ser Gln Ser Ser Ser Glu Ser Ser Ser Ser Glu
            820                 825                 830

Ser Glu Ser Gln Ser Pro Glu Pro Glu Glu Pro Glu Pro Pro Ser Gln
        835                 840                 845

Glu Ser Pro Pro Glu Gln Pro Gln Gln Glu Gln Gln Pro Glu Glu Ser
    850                 855                 860

Ser Ser Ser Ser Ser Ser Pro Gln Ser Glu Pro Pro Glu Glu Pro Ser
865                 870                 875                 880

Pro Gln Gln Gln Gln Ser Ser Ser Ser Ser Pro Glu Ser Ser Pro Pro
                885                 890                 895

Pro Glu Gln Glu Gln Pro Glu Gln Ser Pro Gln Pro Pro Ser Gln Ser
            900                 905                 910

Pro Gln Ser Ser Ser Gln Glu Ser Ser Glu Pro Gln Pro Glu Gln Gln
        915                 920                 925

Ser Pro Glu Glu Glu Pro Ser Pro Ser Gln Ser Ser Ser Ser Ser Pro
    930                 935                 940

Ser Pro Pro Pro Pro Glu Gln Ser Glu Gln Pro Glu Pro Pro Glu Ser
945                 950                 955                 960

Pro Glu Pro Gln Gln Gln Ser Pro Gln Pro Pro Ser Ser Gln Glu Pro
                965                 970                 975

Glu Glu Pro Glu Pro Gln Ser Pro Pro Glu Ser Glu Pro Pro Glu Glu
            980                 985                 990

Glu Ser Gln Ser Pro Gln Pro Gln
        995                 1000
```

```
<210> SEQ ID NO 7
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 7
```

-continued

```
Glu Gln Pro Glu Pro Pro Ser Glu Ser Pro Ser Pro Ser Pro Pro Ser
 1               5                  10                  15

Ser Glu Ser Ser Pro Pro Pro Ser Ser Glu Pro Ser Ser Pro Gln Ser
            20                  25                  30

Gln Ser Pro Glu Glu Glu Pro Ser Gln Ser Gln Pro Ser Glu Ser Ser
        35                  40                  45

Pro Glu Pro Ser Pro Glu Gln Ser Ser Pro Ser Glu Glu Glu Gln Pro
    50                  55                  60

Pro Glu Ser Ser Gln Ser Gln Glu Ser Gln Glu Pro Pro Glu Ser Pro
65                  70                  75                  80

Pro Gln Gln Pro Ser Pro Pro Ser Gln Glu Ser Ser Glu Gln Glu Ser
                85                  90                  95

Pro Glu Gln Glu Glu Ser Glu Pro Pro Ser Glu Glu Pro Glu Pro Pro
            100                 105                 110

Ser Glu Ser Ser Glu Glu Glu Gln Glu Gln Ser Pro Gln Ser Pro Ser
        115                 120                 125

Ser Glu Pro Glu Pro Glu Gln Ser Gln Glu Ser Pro Ser Ser Ser Glu
    130                 135                 140

Ser Pro Ser Pro Glu Glu Ser Pro Pro Gln Pro Pro Glu Pro Pro Glu
145                 150                 155                 160

Ser Pro Pro Pro Ser Pro Glu Gln Glu Gln Gln Pro Glu Glu Glu Ser
                165                 170                 175

Pro Pro Gln Pro Glu Ser Ser Pro Ser Glu Ser Ser Ser Pro Glu Ser
            180                 185                 190

Pro Gln Glu Pro Pro Ser Ser Pro Pro Pro Glu Ser Ser Glu Glu Glu
        195                 200                 205

Glu Ser Gln Glu Ser Ser Pro Gln Gln Ser Glu Glu Gln Ser Ser Ser
    210                 215                 220

Pro Ser Pro Ser Gln Ser Glu Ser Gln Gln Glu Ser Pro Glu Pro Pro
225                 230                 235                 240

Ser Gln Pro Pro Ser Ser Ser Glu Pro Ser Ser Pro Ser Pro Ser Pro
                245                 250                 255

Glu Pro Glu Pro Gln Gln Pro Gln Gln Gln Ser Gln Pro Glu Ser Pro
            260                 265                 270

Ser Pro Ser Pro Gln Gln Pro Ser Gln Pro Ser Glu Glu Ser Pro Glu
        275                 280                 285

Ser Pro Glu Pro Pro Ser Ser Glu Pro Ser Glu Pro Ser Glu Glu Pro
    290                 295                 300

Glu Ser Glu Gln Glu Pro Ser Ser Pro Pro Glu Ser Ser Glu Pro Glu
305                 310                 315                 320

Gln Ser Gln Glu Glu Pro Glu Pro Glu Gln Ser Gln Ser Glu Ser Ser
                325                 330                 335

Pro Glu Glu Ser Pro Glu Ser Ser Glu Gln Gln Gln Glu Pro Glu Pro
            340                 345                 350

Pro Ser Pro Ser Ser Gln Ser Pro Pro Ser Ser Pro Pro Ser Ser Glu
        355                 360                 365

Pro Pro Ser Pro Pro Glu Pro Ser Pro Ser Ser Glu Ser Pro Glu Gln
    370                 375                 380

Gln Gln Glu Glu Gln Pro Ser Glu Glu Pro Gln Ser Ser Ser Glu Glu
385                 390                 395                 400

Gln Ser Gln Ser Ser Glu Pro Pro Glu Pro Ser Pro Gln Ser Ser Pro
                405                 410                 415

Ser Pro Gln Ser Glu Pro Pro Glu Gln Glu Gln Glu Glu Pro Glu Gln
            420                 425                 430
```

-continued

Ser Glu Pro Gln Pro Glu Pro Pro Glu Gln Ser Pro Glu Pro Ser Ser
        435                 440                 445

Ser Pro Glu Gln Gln Pro Glu Pro Pro Pro Gln Ser Ser Ser Pro Pro
    450                 455                 460

Ser Gln Glu Glu Ser Ser Pro Pro Glu Glu Ser Ser Pro Glu Glu Ser
465                 470                 475                 480

Ser Glu Glu Pro Ser Ser Glu Gln Gln Gln Glu Pro Ser Ser Pro Gln
                485                 490                 495

Glu Pro Glu Pro Ser Ser Gln Pro Pro Glu Pro Pro Gln Gln Pro Glu
            500                 505                 510

Pro Glu Pro Ser Glu Pro Pro Pro Ser Gln Ser Glu Pro Pro Pro Ser
        515                 520                 525

Pro Pro Glu Glu Gln Gln Ser Ser Pro Pro Glu Pro Glu Pro Pro Pro
    530                 535                 540

Glu Ser Pro Ser Gln Glu Glu Pro Pro Ser Ser Ser Gln Glu Glu Gln
545                 550                 555                 560

Gln Glu Pro Glu Ser Gln Glu Pro Glu Glu Ser Gln Pro Glu Pro Pro
                565                 570                 575

Ser Pro Pro Gln Pro Glu Glu Glu Ser Pro Gln Ser Glu Glu Pro Pro
            580                 585                 590

Ser Pro Ser Gln Pro Ser Pro Ser Glu Glu Gln Ser Glu Pro Ser Gln
        595                 600                 605

Gln Gln Glu Pro Ser Gln Pro Ser Glu Ser Pro Glu Ser Pro Gln Glu
    610                 615                 620

Ser Glu Gln Glu Pro Glu Glu Pro Glu Ser Ser Pro Glu Glu Glu Ser
625                 630                 635                 640

Pro Ser Pro Gln Ser Pro Pro Ser Ser Pro Pro Pro Glu Ser Glu Glu
                645                 650                 655

Gln Pro Glu Glu Gln Pro Pro Gln Gln Ser Pro Glu Pro Pro Pro Ser
            660                 665                 670

Ser Pro Glu Ser Pro Glu Ser Glu Pro Glu Glu Ser Pro Pro Glu Glu
        675                 680                 685

Ser Glu Glu Gln Pro Gln Gln Pro Ser Gln Glu Glu Pro Pro Glu Ser
    690                 695                 700

Gln Glu Ser Ser Ser Pro Gln Ser Ser Ser Glu Glu Ser Pro Pro Pro
705                 710                 715                 720

Gln Glu Ser Glu Gln Pro Glu Pro Glu Ser Glu Gln Glu Pro Pro Pro
                725                 730                 735

Glu Gln Gln Pro Glu Gln Ser Glu Gln Ser Ser Glu Gln Gln Pro Pro
            740                 745                 750

Pro Glu Ser Ser Gln Pro Pro Ser Ser Ser Ser Glu Ser Glu Glu Glu
        755                 760                 765

Glu Glu Ser Ser Glu Gln Glu Pro Ser Ser Ser Glu Glu Pro Glu Ser
    770                 775                 780

Ser Glu Ser Ser Ser Glu Gln Ser Ser Glu Ser Glu Glu Ser Glu Glu
785                 790                 795                 800

Glu Pro Pro Gln Gln Gln Glu Glu Ser Pro Pro Ser Glu Glu Glu Glu
                805                 810                 815

Gln Gln Gln Pro Pro Pro Glu Pro Glu Ser Glu Ser Pro Glu Gln Ser
            820                 825                 830

Gln Pro Ser Glu Pro Ser Pro Ser Ser Glu Ser Gln Glu Glu Pro Gln
        835                 840                 845

Glu Pro Ser Ser Ser Pro Ser Pro Glu Glu Pro Gln Glu Glu Ser Glu

-continued

```
    850                 855                 860

Glu Ser Pro Pro Glu Ser Pro Glu Ser Ser Gln Pro Ser Pro Ser Ser
865                 870                 875                 880

Gln Glu Pro Pro Glu Ser Glu Glu Ser Gln Pro Glu Gln Glu Ser Ser
                885                 890                 895

Pro Glu Glu Pro Glu Pro Pro Pro Pro Glu Pro Glu Glu Pro Pro Pro
            900                 905                 910

Pro Pro Ser Pro Glu Pro Glu Glu Glu Glu Gln Pro Gln Pro Ser Gln
        915                 920                 925

Gln Ser Ser Ser Gln Glu Glu Glu Ser Glu Ser Ser Glu Glu Pro Ser
    930                 935                 940

Ser Glu Pro Ser Ser Glu Pro Glu Glu Ser Ser Ser Ser Ser Pro Ser
945                 950                 955                 960

Ser Glu Gln Gln Ser Glu Ser Gln Glu Glu Pro Glu Glu Glu Ser Glu
                965                 970                 975

Glu Pro Pro Pro Ser Ser Glu Ser Pro Glu Glu Glu Glu Glu Pro Ser
            980                 985                 990

Glu Pro Pro Glu Ser Ser Glu Pro
        995                 1000


<210> SEQ ID NO 8
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 8

Ser Pro Glu Gln Pro Glu Pro Gln Pro Glu Pro Glu Gln Glu Ser Glu
 1               5                  10                  15

Pro Glu Pro Ser Glu Pro Pro Pro Ser Gln Glu Glu Glu Ser Glu Glu
            20                  25                  30

Glu Glu Gln Ser Glu Gln Pro Glu Glu Glu Ser Ser Glu Pro Ser Pro
        35                  40                  45

Glu Ser Ser Pro Ser Pro Gln Glu Pro Ser Pro Gln Gln Glu Pro Pro
    50                  55                  60

Ser Glu Pro Gln Gln Glu Ser Glu Pro Ser Gln Ser Pro Ser Ser Glu
65                  70                  75                  80

Ser Glu Gln Ser Glu Glu Gln Glu Pro Gln Glu Glu Ser Glu Ser Glu
                85                  90                  95

Glu Ser Pro Glu Ser Ser Pro Ser Ser Glu Pro Ser Glu Glu Glu Ser
            100                 105                 110

Glu Gln Ser Glu Ser Ser Glu Glu Glu Glu Pro Pro Ser Pro Pro Ser
        115                 120                 125

Pro Glu Glu Glu Ser Pro Glu Ser Gln Glu Gln Gln Glu Pro Glu Gln
    130                 135                 140

Gln Ser Glu Pro Glu Glu Glu Ser Ser Ser Ser Pro Ser Pro Glu Pro
145                 150                 155                 160

Ser Glu Glu Pro Pro Pro Glu Ser Glu Pro Ser Glu Glu Ser Pro Pro
                165                 170                 175

Ser Glu Gln Ser Glu Pro Glu Pro Pro Pro Glu Ser Ser Glu Pro Pro
            180                 185                 190

Gln Gln Glu Gln Glu Ser Glu Glu Ser Ser Ser Pro Pro Glu Ser Glu
        195                 200                 205

Pro Pro Glu Gln Ser Ser Glu Pro Glu Glu Glu Gln Gln Ser Glu Glu
```

-continued

```
    210                 215                 220

Glu Glu Ser Pro Glu Glu Glu Ser Ser Glu Glu Ser Ser Pro Glu Gln
225                 230                 235                 240

Ser Ser Ser Ser Ser Glu Glu Glu Ser Ser Glu Glu Pro Glu Ser Pro
                245                 250                 255

Glu Glu Glu Glu Pro Ser Gln Pro Glu Gln Pro Gln Gln Ser Pro Pro
            260                 265                 270

Gln Glu Ser Pro Pro Glu Glu Ser Gln Glu Pro Pro Ser Glu Ser Ser
        275                 280                 285

Ser Ser Glu Gln Ser Ser Glu Ser Gln Ser Gln Ser Pro Ser Ser Ser
    290                 295                 300

Ser Glu Pro Gln Glu Pro Gln Pro Pro Glu Pro Ser Ser Gln Glu Glu
305                 310                 315                 320

Pro Glu Pro Pro Glu Gln Glu Pro Glu Pro Ser Gln Pro Ser Glu Glu
                325                 330                 335

Ser Ser Pro Ser Ser Glu Pro Glu Glu Ser Pro Pro Glu Glu Glu Ser
            340                 345                 350

Glu Ser Ser Glu Ser Glu Glu Ser Glu Glu Glu Glu Glu Glu Glu Glu
        355                 360                 365

Ser Pro Ser Pro Ser Pro Gln Glu Pro Ser Ser Gln Pro Pro Ser Glu
    370                 375                 380

Glu Pro Ser Glu Glu Pro Ser Pro Glu Glu Gln Glu Ser Glu Glu Glu
385                 390                 395                 400

Glu Ser Pro Ser Ser Ser Glu Gln Glu Glu Pro Ser Gln Ser Glu Gln
                405                 410                 415

Gln Ser Pro Pro Ser Ser Pro Pro Glu Ser Glu Gln Ser Gln Glu Glu
            420                 425                 430

Glu Pro Glu Glu Glu Glu Gln Pro Pro Glu Pro Ser Gln Ser Pro Glu
        435                 440                 445

Glu Ser Glu Ser Glu Glu Gln Gln Ser Ser Glu Ser Glu Pro Pro Gln
    450                 455                 460

Ser Pro Pro Glu Glu Pro Glu Pro Glu Gln Gln Gln Ser Ser Ser Glu
465                 470                 475                 480

Glu Ser Glu Gln Glu Ser Glu Pro Ser Gln Glu Glu Ser Glu Ser Glu
                485                 490                 495

Ser Glu Glu Ser Glu Glu Ser Ser Pro Ser Ser Ser Pro Gln Pro Glu
            500                 505                 510

Glu Pro Glu Ser Glu Glu Glu Gln Pro Ser Pro Ser Pro Glu Ser Gln
        515                 520                 525

Glu Pro Glu Glu Ser Glu Pro Ser Glu Glu Pro Ser Gln Ser Pro Glu
    530                 535                 540

Glu Glu Glu Glu Glu Pro Glu Pro Glu Pro Gln Gln Ser Glu Glu Glu
545                 550                 555                 560

Gln Pro Gln Glu Ser Ser Gln Gln Glu Glu Glu Glu Pro Pro Glu Ser
                565                 570                 575

Glu Gln Gln Pro Ser Ser Glu Gln Glu Glu Ser Glu Glu Pro Gln Gln
            580                 585                 590

Glu Glu Pro Ser Glu Ser Gln Pro Gln Pro Pro Glu Ser Ser Pro Pro
        595                 600                 605

Ser Pro Pro Pro Pro Glu Glu Pro Ser Gln Glu Glu Ser Glu Gln Glu
    610                 615                 620

Pro Glu Glu Glu Gln Ser Pro Pro Glu Pro Glu Glu Gln Glu Pro Ser
625                 630                 635                 640
```

-continued

```
Pro Ser Glu Ser Glu Glu Ser Pro Pro Glu Ser Glu Ser Ser Glu Glu
                645                 650                 655

Gln Gln Glu Glu Ser Glu Pro Glu Ser Glu Glu Glu Pro Pro Gln Gln
            660                 665                 670

Ser Glu Glu Gln Gln Ser Gln Pro Glu Glu Glu Glu Glu Glu Gln Ser
        675                 680                 685

Glu Glu Pro Ser Ser Ser Pro Pro Glu Pro Pro Gln Gln Glu Pro Ser
    690                 695                 700

Ser Pro Ser Glu Gln Pro Pro Gln Pro Glu Glu Pro Glu Pro Glu Glu
705                 710                 715                 720

Glu Ser Glu Glu Pro Ser Pro Glu Gln Pro Ser Glu Ser Ser Glu Pro
                725                 730                 735

Pro Glu Ser Pro Glu Glu Pro Ser Pro Pro Pro Pro Ser Ser Glu Glu
            740                 745                 750

Ser Glu Ser Glu Ser Glu Gln Pro Glu Glu Gln Pro Glu Ser Glu Glu
        755                 760                 765

Pro Pro Ser Ser Pro Ser Glu Ser Ser Glu Glu Pro Glu Glu Glu Pro
    770                 775                 780

Glu Glu Glu Gln Pro Ser Glu Pro Gln Pro Pro Ser Glu Gln Pro Ser
785                 790                 795                 800

Pro Pro Glu Glu Pro Gln Glu Glu Ser Glu Glu Glu Pro Pro Ser Glu
                805                 810                 815

Glu Pro Ser Gln Ser Glu Ser Pro Glu Pro Glu Pro Ser Pro Ser Ser
            820                 825                 830

Pro Pro Pro Gln Glu Pro Glu Gln Pro Ser Ser Ser Glu Gln Ser Pro
        835                 840                 845

Pro Glu Pro Ser Glu Gln Ser Pro Pro Ser Gln Glu Glu Pro Glu Glu
    850                 855                 860

Glu Pro Ser Gln Ser Glu Gln Glu Ser Glu Glu Gln Pro Gln Glu Glu
865                 870                 875                 880

Pro Pro Gln Pro Ser Pro Glu Pro Ser Pro Gln Glu Pro Ser Glu Pro
                885                 890                 895

Glu Pro Glu Glu Pro Pro Glu Glu Glu Pro Pro Gln Pro Pro Pro Ser
            900                 905                 910

Ser Glu Pro Glu Glu Gln Glu Ser Ser Ser Pro Glu Pro Gln Gln Pro
        915                 920                 925

Gln Pro Ser Ser Ser Pro Glu Glu Glu Pro Pro Glu Glu Ser Pro Glu
    930                 935                 940

Pro Ser Pro Gln Pro Glu Pro Glu Ser Glu Pro Glu Glu Glu Gln Ser
945                 950                 955                 960

Pro Ser Glu Gln Glu Pro Glu Glu Glu Glu Ser Gln Glu Pro Ser Ser
                965                 970                 975

Pro Gln Glu Pro Glu Glu Glu Gln Ser Glu Ser Glu Ser Pro Ser Pro
            980                 985                 990

Glu Pro Glu Pro Glu Pro Glu Glu
        995                 1000
```

```
<210> SEQ ID NO 9
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 9
```

-continued

```
Pro Gln Glu Pro Ser Glu Ser Glu Ser Pro Gln Pro Ser Glu Ser Glu
 1               5                  10                  15

Glu Glu Gln Pro Glu Gln Glu Ser Pro Glu Gln Ser Ser Glu Glu Pro
            20                  25                  30

Ser Gln Glu Gln Glu Glu Gln Glu Glu Pro Ser Glu Glu Glu Glu Pro
        35                  40                  45

Glu Glu Ser Pro Glu Pro Ser Glu Glu Gln Glu Pro Pro Pro Pro Glu
    50                  55                  60

Glu Pro Glu Glu Ser Pro Pro Glu Pro Glu Glu Glu Glu Glu Glu Glu
65                  70                  75                  80

Ser Glu Ser Pro Glu Pro Gln Ser Glu Ser Glu Glu Glu Ser Pro Glu
                85                  90                  95

Glu Pro Pro Gln Ser Glu Glu Pro Gln Ser Pro Gln Pro Glu Pro Ser
            100                 105                 110

Pro Glu Glu Glu Pro Pro Glu Pro Glu Gln Pro Glu Pro Ser Pro Gln
        115                 120                 125

Ser Glu Glu Pro Gln Glu Pro Gln Glu Glu Glu Glu Pro Glu Glu Pro
    130                 135                 140

Glu Pro Glu Glu Glu Glu Pro Pro Glu Glu Glu Ser Glu Glu Ser Ser
145                 150                 155                 160

Gln Glu Ser Pro Ser Glu Glu Pro Ser Ser Ser Pro Glu Ser Glu Glu
                165                 170                 175

Glu Glu Glu Pro Pro Gln Glu Pro Ser Ser Glu Ser Glu Pro Glu Glu
            180                 185                 190

Glu Ser Pro Gln Glu Glu Glu Glu Ser Glu Gln Ser Gln Glu Ser Glu
        195                 200                 205

Glu Gln Gln Glu Glu Ser Pro Ser Pro Glu Ser Glu Ser Ser Pro Pro
    210                 215                 220

Glu Ser Gln Glu Ser Glu Ser Glu Glu Glu Glu Gln Glu Ser Glu Ser
225                 230                 235                 240

Ser Ser Gln Pro Ser Glu Pro Glu Glu Glu Gln Glu Glu Glu Glu Glu
                245                 250                 255

Ser Pro Glu Pro Glu Gln Glu Pro Glu Pro Glu Glu Ser Ser Ser Ser
            260                 265                 270

Ser Glu Ser Gln Ser Glu Ser Ser Glu Gln Glu Ser Ser Gln Glu Ser
        275                 280                 285

Glu Gln Ser Pro Pro Glu Glu Glu Glu Ser Glu Ser Ser Gln Glu Ser
    290                 295                 300

Glu Ser Pro Glu Ser Glu Gln Glu Gln Pro Pro Glu Glu Ser Glu Glu
305                 310                 315                 320

Glu Gln Pro Pro Glu Glu Pro Glu Glu Gln Pro Gln Glu Pro Gln Ser
                325                 330                 335

Ser Pro Gln Glu Ser Pro Ser Ser Pro Glu Ser Glu Ser Pro Pro Ser
            340                 345                 350

Glu Pro Pro Pro Ser Glu Glu Glu Glu Pro Pro Glu Gln Glu Glu Pro
        355                 360                 365

Pro Glu Ser Glu Glu Glu Pro Glu Glu Glu Glu Glu Glu Glu Glu Glu
    370                 375                 380

Pro Glu Glu Glu Glu Glu Glu Pro Ser Glu Glu Ser Pro Glu Ser Glu
385                 390                 395                 400

Ser Glu Pro Pro Pro Pro Ser Ser Glu Pro Ser Glu Pro Ser Glu Pro
                405                 410                 415

Glu Ser Pro Glu Glu Glu Ser Ser Pro Glu Glu Ser Gln Ser Pro Glu
            420                 425                 430
```

```
Glu Glu Glu Glu Glu Ser Glu Glu Glu Pro Gln Pro Glu Ser Ser Glu
        435                 440                 445

Pro Glu Glu Pro Glu Glu Gln Glu Gln Gln Glu Glu Gln Glu Glu Pro
    450                 455                 460

Pro Ser Pro Gln Pro Pro Glu Glu Gln Pro Gln Gln Gln Glu Gln Glu
465                 470                 475                 480

Gln Ser Glu Pro Ser Glu Gln Gln Glu Gln Pro Ser Ser Ser Pro Glu
                485                 490                 495

Ser Glu Glu Glu Ser Glu Pro Glu Glu Pro Glu Pro Glu Gln Glu Ser
            500                 505                 510

Pro Pro Glu Ser Glu Glu Glu Ser Glu Gln Pro Pro Glu Ser Pro Ser
        515                 520                 525

Ser Glu Pro Ser Ser Pro Glu Glu Ser Gln Glu Ser Ser Ser Pro Glu
    530                 535                 540

Ser Pro Glu Ser Pro Ser Pro Pro Glu Ser Ser Gln Pro Glu Glu Glu
545                 550                 555                 560

Pro Gln Gln Glu Pro Glu Pro Ser Ser Pro Gln Pro Gln Glu Gln Pro
                565                 570                 575

Glu Glu Glu Glu Ser Pro Pro Pro Ser Ser Pro Glu Gln Pro Glu Glu
            580                 585                 590

Pro Glu Glu Glu Ser Ser Ser Gln Ser Ser Gln Glu Glu Gln Pro Ser
        595                 600                 605

Glu Glu Glu Ser Glu Glu Glu Glu Ser Gln Glu Glu Pro Ser Glu Ser
    610                 615                 620

Ser Glu Glu Pro Glu Glu Glu Glu Glu Glu Pro Pro Glu Ser Gln Ser
625                 630                 635                 640

Glu Glu Gln Ser Gln Glu Glu Gln Pro Glu Ser Pro Gln Glu Glu Glu
                645                 650                 655

Gln Ser Glu Ser Pro Pro Gln Pro Pro Glu Glu Pro Glu Glu Gln Ser
            660                 665                 670

Ser Gln Glu Glu Ser Glu Glu Glu Gln Pro Ser Glu Gln Ser Ser Glu
        675                 680                 685

Glu Pro Ser Ser Glu Ser Glu Glu Ser Glu Pro Gln Glu Ser Glu Glu
    690                 695                 700

Glu Glu Pro Pro Ser Glu Pro Glu Ser Glu Gln Gln Ser Glu Glu Pro
705                 710                 715                 720

Pro Gln Ser Gln Glu Glu Ser Pro Gln Pro Ser Pro Ser Glu Pro Glu
                725                 730                 735

Glu Glu Glu Gln Pro Ser Glu Glu Glu Pro Ser Gln Glu Gln Glu Pro
            740                 745                 750

Glu Glu Glu Glu Glu Glu Glu Ser Ser Glu Pro Pro Glu Glu Glu Glu
        755                 760                 765

Pro Gln Glu Glu Pro Glu Glu Pro Pro Glu Glu Glu Glu Glu Glu Glu
    770                 775                 780

Gln Ser Glu Glu Glu Glu Glu Pro Glu Glu Pro Ser Glu Gln Glu Glu
785                 790                 795                 800

Glu Pro Pro Glu Glu Pro Glu Glu Ser Glu Ser Glu Ser Pro Ser Pro
                805                 810                 815

Glu Pro Ser Ser Ser Glu Gln Ser Ser Pro Ser Glu Gln Glu Gln Ser
            820                 825                 830

Ser Glu Glu Ser Gln Pro Glu Pro Glu Pro Glu Glu Gln Ser Glu Glu
        835                 840                 845

Ser Ser Gln Pro Pro Glu Pro Glu Pro Pro Pro Pro Pro Glu Ser Glu
```

```
    850                 855                 860

Ser Ser Ser Ser Glu Ser Glu Ser Glu Gln Ser Glu Ser Gln Glu Glu
865                 870                 875                 880

Pro Glu Pro Ser Glu Glu Pro Ser Glu Gln Ser Ser Glu Ser Glu Glu
                885                 890                 895

Pro Glu Ser Glu Glu Glu Glu Glu Ser Pro Glu Glu Pro Glu Gln Glu
            900                 905                 910

Gln Pro Ser Glu Pro Glu Glu Pro Glu Pro Glu Ser Glu Gln Glu Glu
        915                 920                 925

Glu Ser Glu Ser Pro Pro Pro Pro Pro Ser Glu Glu Ser Pro Pro Gln
    930                 935                 940

Ser Ser Glu Pro Ser Pro Glu Glu Gln Pro Gln Glu Ser Glu Pro Glu
945                 950                 955                 960

Pro Glu Pro Ser Ser Pro Pro Glu Pro Pro Pro Glu Glu Glu Ser Ser
                965                 970                 975

Glu Pro Glu Ser Glu Glu Glu Ser Glu Ser Ser Glu Gln Glu Pro Glu
            980                 985                 990

Glu Pro Pro Glu Ser Glu Ser Glu
        995                 1000


<210> SEQ ID NO 10
<211> LENGTH: 1000
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 10

Glu Glu Glu Glu Ser Ser Pro Pro Glu Glu Glu Glu Ser Ser Pro Glu
 1               5                  10                  15

Pro Glu Glu Pro Glu Pro Glu Pro Ser Pro Pro Gln Glu Glu Glu Glu
            20                  25                  30

Glu Pro Ser Pro Gln Glu Gln Gln Pro Gln Gln Gln Glu Ser Ser Gln
        35                  40                  45

Glu Glu Glu Gln Glu Pro Glu Glu Glu Glu Gln Glu Ser Ser Ser Pro
    50                  55                  60

Gln Glu Glu Pro Pro Gln Pro Glu Glu Glu Pro Glu Pro Glu Glu Glu
65                  70                  75                  80

Glu Glu Ser Ser Ser Glu Glu Glu Glu Pro Glu Glu Gln Glu Gln Pro
                85                  90                  95

Glu Pro Glu Glu Glu Pro Ser Pro Glu Ser Ser Glu Ser Glu Ser Ser
            100                 105                 110

Ser Ser Glu Glu Glu Glu Glu Gln Pro Ser Gln Pro Glu Ser Ser Pro
        115                 120                 125

Ser Glu Glu Glu Gln Pro Gln Glu Pro Glu Glu Pro Glu Pro Glu Glu
    130                 135                 140

Glu Ser Pro Ser Pro Pro Glu Glu Gln Glu Glu Glu Ser Glu Ser Glu
145                 150                 155                 160

Glu Glu Gln Glu Gln Ser Glu Pro Glu Glu Ser Glu Glu Glu Glu Glu
                165                 170                 175

Pro Ser Ser Pro Gln Ser Glu Gln Glu Glu Pro Gln Glu Pro Glu Pro
            180                 185                 190

Glu Glu Gln Glu Glu Glu Pro Pro Glu Glu Glu Gln Glu Pro Pro
        195                 200                 205

Glu Ser Glu Ser Pro Glu Glu Gln Glu Glu Glu Gln Pro Pro Ser Pro
```

-continued

```
    210                 215                 220

Glu Glu Glu Ser Glu Glu Glu Glu Glu Pro Glu Glu Glu Glu Glu Gln
225                 230                 235                 240

Glu Glu Ser Glu Glu Glu Glu Ser Gln Ser Pro Ser Glu Glu Pro Glu
                245                 250                 255

Pro Glu Glu Ser Ser Ser Pro Glu Ser Glu Glu Pro Pro Glu Glu Glu
            260                 265                 270

Ser Ser Glu Glu Ser Ser Glu Glu Ser Gln Glu Glu Ser Pro Ser Pro
        275                 280                 285

Glu Glu Glu Glu Glu Ser Ser Glu Ser Glu Gln Pro Pro Glu Ser Pro
    290                 295                 300

Ser Glu Ser Gln Glu Ser Pro Ser Gln Ser Glu Glu Glu Ser Gln Glu
305                 310                 315                 320

Glu Pro Pro Glu Glu Glu Ser Ser Pro Glu Glu Glu Pro Pro Pro Ser
                325                 330                 335

Pro Ser Glu Ser Glu Pro Pro Glu Glu Glu Glu Glu Pro Ser Glu Ser
            340                 345                 350

Glu Glu Glu Glu Pro Pro Pro Glu Glu Glu Glu Ser Ser Ser Glu Glu
        355                 360                 365

Gln Glu Ser Glu Glu Pro Glu Ser Glu Glu Glu Ser Pro Glu Glu Gln
    370                 375                 380

Ser Glu Glu Glu Glu Glu Ser Gln Glu Ser Ser Pro Glu Pro Pro Glu
385                 390                 395                 400

Glu Ser Pro Ser Glu Gln Pro Glu Pro Ser Pro Pro Glu Pro Glu Ser
                405                 410                 415

Glu Ser Ser Glu Pro Glu Glu Glu Glu Glu Glu Glu Glu Glu Pro Pro
            420                 425                 430

Ser Ser Glu Glu Glu Glu Ser Glu Glu Pro Glu Gln Pro Glu Glu Glu
        435                 440                 445

Gln Glu Glu Pro Gln Glu Glu Glu Glu Ser Pro Ser Glu Glu Ser Pro
    450                 455                 460

Glu Glu Pro Glu Glu Ser Glu Pro Glu Glu Glu Ser Glu Glu Glu Glu
465                 470                 475                 480

Pro Glu Gln Gln Pro Glu Glu Glu Pro Pro Glu Glu Glu Glu Gln Glu
                485                 490                 495

Ser Ser Glu Pro Ser Ser Pro Pro Ser Glu Glu Gln Ser Glu Glu Pro
            500                 505                 510

Glu Glu Gln Glu Glu Pro Pro Glu Pro Ser Gln Pro Glu Pro Gln Gln
        515                 520                 525

Glu Ser Glu Ser Ser Ser Pro Ser Glu Ser Gln Pro Glu Ser Gln Glu
    530                 535                 540

Ser Glu Glu Glu Glu Glu Glu Glu Ser Glu Glu Glu Ser Glu Pro
545                 550                 555                 560

Ser Gln Glu Pro Glu Glu Gln Gln Pro Glu Glu Glu Glu Glu Glu Glu
                565                 570                 575

Glu Glu Pro Glu Glu Glu Glu Glu Gln Ser Glu Pro Glu Glu Ser Ser
            580                 585                 590

Glu Gln Gln Glu Pro Pro Gln Ser Ser Gln Pro Gln Glu Glu Ser Glu
        595                 600                 605

Gln Glu Gln Glu Glu Pro Gln Ser Pro Glu Glu Glu Ser Pro Pro Pro
    610                 615                 620

Glu Glu Glu Glu Pro Gln Glu Glu Pro Pro Glu Pro Glu Glu Glu Glu
625                 630                 635                 640
```

```
Pro Ser Glu Gln Pro Pro Ser Ser Pro Pro Glu Glu Gln Ser Glu Gln
                645                 650                 655

Pro Glu Gln Ser Glu Pro Gln Ser Glu Ser Pro Ser Gln Pro Glu Ser
            660                 665                 670

Ser Glu Gln Pro Glu Glu Gln Pro Glu Pro Pro Ser Pro Gln Ser Ser
        675                 680                 685

Glu Glu Ser Glu Glu Pro Glu Glu Glu Glu Gln Ser Glu Glu Pro Ser
    690                 695                 700

Pro Ser Gln Ser Glu Ser Ser Ser Ser Pro Glu Glu Ser Glu Pro Pro
705                 710                 715                 720

Glu Glu Glu Glu Glu Glu Glu Glu Pro Glu Glu Pro Glu Gln Glu Glu
                725                 730                 735

Glu Gln Ser Glu Pro Gln Glu Gln Glu Pro Ser Glu Glu Ser Ser Glu
            740                 745                 750

Pro Glu Glu Glu Ser Ser Pro Ser Ser Gln Ser Ser Glu Gln Ser Ser
        755                 760                 765

Ser Glu Glu Glu Ser Glu Ser Glu Gln Ser Ser Pro Pro Pro Glu Glu
    770                 775                 780

Glu Ser Pro Glu Glu Glu Glu Pro Glu Glu Glu Glu Pro Glu Glu Ser
785                 790                 795                 800

Pro Glu Glu Glu Ser Glu Glu Ser Pro Glu Ser Glu Glu Ser Glu Glu
                805                 810                 815

Ser Ser Glu Glu Gln Glu Glu Ser Ser Pro Glu Glu Glu Pro Ser Glu
            820                 825                 830

Gln Glu Glu Pro Pro Glu Gln Glu Pro Glu Ser Pro Pro Glu Gln Glu
        835                 840                 845

Glu Glu Glu Glu Gln Ser Glu Pro Gln Glu Glu Glu Pro Pro Glu Ser
    850                 855                 860

Ser Glu Pro Glu Glu Glu Ser Pro Pro Glu Glu Pro Gln Ser Glu Glu
865                 870                 875                 880

Glu Glu Glu Glu Pro Gln Pro Glu Ser Glu Ser Glu Pro Glu Glu Pro
                885                 890                 895

Ser Pro Glu Pro Glu Ser Glu Glu Ser Glu Glu Glu Pro Glu Ser Glu
            900                 905                 910

Ser Ser Ser Pro Pro Glu Ser Ser Ser Glu Glu Glu Glu Glu Glu Pro
        915                 920                 925

Glu Glu Gln Ser Glu Glu Glu Glu Glu Ser Gln Glu Glu Glu Glu Gln
    930                 935                 940

Glu Glu Glu Pro Ser Gln Glu Glu Glu Glu Pro Glu Glu Gln Gln Pro
945                 950                 955                 960

Pro Ser Glu Glu Glu Glu Gln Pro Glu Gln Ser Glu Glu Pro Glu Pro
                965                 970                 975

Ser Glu Pro Ser Glu Glu Glu Pro Glu Pro Glu Glu Ser Pro Pro Glu
            980                 985                 990

Ser Gln Pro Pro Ser Glu Glu Pro
        995                 1000
```

<210> SEQ ID NO 11
<211> LENGTH: 1000
<212> TYPE: PRT
<213> ORGANISM: Artificial Sequence
<220> FEATURE:
<223> OTHER INFORMATION: Randomly generated sequence, created by ExPASy
WWW server tool

<400> SEQUENCE: 11

-continued

```
Gly Gln Gln Gly Ser Ser Pro Pro Ser Pro Ser Gln Gly Gly Gln Pro
 1               5                  10                  15

Pro Ser Ser Gln Pro Ser Gln Gln Ser Ser Ser Ser Pro Pro Pro Ser
            20                  25                  30

Pro Pro Pro Ser Ser Pro Pro Ser Gln Pro Pro Ser Pro Pro Ser Ser
        35                  40                  45

Gly Ser Gly Ser Ser Ser Pro Ser Gln Gly Ser Pro Pro Ser Pro Pro
    50                  55                  60

Ser Gln Gly Pro Pro Gln Pro Pro Gln Ser Pro Gly Ser Gln Gly Pro
65                  70                  75                  80

Pro Pro Pro Pro Gly Pro Gly Ser Gly Pro Pro Pro Ser Ser Ser Pro
                85                  90                  95

Gln Pro Ser Gln Pro Pro Pro Ser Gln Pro Ser Gln Gln Ser Pro Gln
            100                 105                 110

Pro Ser Pro Gly Pro Gly Ser Pro Ser Gln Gln Pro Ser Ser Gly Ser
        115                 120                 125

Gln Gln Ser Pro Gly Gln Gly Pro Gln Pro Gln Gly Pro Ser Gly Ser
    130                 135                 140

Pro Gln Gly Gln Gly Ser Pro Gly Ser Ser Ser Gly Pro Gln Pro Ser
145                 150                 155                 160

Ser Gln Gly Ser Pro Pro Gly Pro Pro Pro Gly Pro Ser Pro Ser Gly
                165                 170                 175

Gly Pro Gln Ser Ser Pro Gly Ser Pro Pro Ser Pro Gln Gly Ser Gln
            180                 185                 190

Pro Gln Ser Pro Gly Pro Ser Ser Pro Ser Ser Ser Pro Gln Pro Pro
        195                 200                 205

Ser Gly Pro Pro Ser Ser Gly Gly Gln Ser Ser Gln Gly Gln Ser Pro
    210                 215                 220

Ser Gln Gly Pro Pro Pro Gly Ser Pro Gln Pro Pro Gly Gly Ser Gly
225                 230                 235                 240

Pro Ser Pro Ser Ser Ser Pro Pro Pro Ser Pro Pro Pro Pro Gln Ser
                245                 250                 255

Ser Ser Ser Gly Ser Gln Gln Ser Ser Ser Ser Ser Gly Ser Pro Pro
            260                 265                 270

Ser Ser Ser Gln Gly Pro Pro Gln Ser Ser Ser Gln Pro Gln Ser Gln
        275                 280                 285

Ser Ser Pro Ser Gln Pro Pro Ser Gly Ser Pro Gly Ser Ser Ser Ser
    290                 295                 300

Pro Ser Pro Ser Pro Ser Gly Pro Ser Gly Ser Pro Ser Gly Pro Pro
305                 310                 315                 320

Ser Ser Pro Ser Gly Ser Pro Pro Pro Gly Gly Pro Pro Gln Ser Gly
                325                 330                 335

Gly Pro Gly Pro Ser Ser Gly Gln Gln Pro Pro Gly Pro Gln Pro Gly
            340                 345                 350

Ser Pro Pro Gly Gln Pro Gln Pro Gly Ser Ser Ser Gln Gly Pro Gln
        355                 360                 365

Gln Gly Pro Pro Pro Gly Ser Pro Gln Gly Pro Ser Gln Pro Gly Pro
    370                 375                 380

Gln Ser Pro Pro Ser Ser Gly Gly Ser Ser Ser Gln Pro Gln Ser Pro
385                 390                 395                 400

Ser Ser Gly Pro Gly Gln Pro Ser Pro Ser Pro Pro Gly Ser Pro Gly
                405                 410                 415

Gly Pro Gly Gln Pro Pro Ser Gln Pro Ser Pro Ser Ser Ser Ser Ser
            420                 425                 430
```

```
Gln Ser Gly Gln Ser Ser Gln Pro Ser Gly Pro Pro Ser Gly Gln Ser
        435                 440                 445

Gln Pro Gly Gln Pro Pro Gln Pro Ser Pro Pro Ser Pro Pro Pro Pro
    450                 455                 460

Ser Pro Pro Ser Gln Ser Gly Ser Gly Ser Pro Gly Pro Pro Ser Gly
465                 470                 475                 480

Pro Gln Pro Ser Ser Gln Pro Ser Pro Ser Gln Pro Gly Gln Gly Pro
                485                 490                 495

Ser Ser Ser Pro Pro Gly Gln Ser Gly Pro Ser Ser Pro Ser Ser Ser
            500                 505                 510

Gln Pro Pro Pro Ser Gln Ser Pro Pro Gln Ser Gly Gln Ser Pro Ser
        515                 520                 525

Ser Ser Pro Pro Gln Ser Ser Pro Ser Ser Gly Gln Gln Pro Ser Pro
    530                 535                 540

Gly Pro Pro Ser Ser Ser Ser Pro Gln Pro Ser Ser Ser Gln Gly Ser
545                 550                 555                 560

Pro Pro Pro Gln Pro Gln Gly Gln Ser Pro Pro Ser Gln Gln Pro Ser
                565                 570                 575

Gln Pro Gly Gly Ser Ser Gln Pro Ser Ser Pro Pro Pro Pro Gly Pro
            580                 585                 590

Gln Gly Pro Gln Pro Pro Ser Pro Gln Pro Pro Ser Gly Pro Gly Ser
        595                 600                 605

Gln Pro Gln Gly Gly Ser Pro Ser Ser Gln Gly Gly Gln Pro Ser Ser
    610                 615                 620

Ser Pro Pro Gln Ser Ser Ser Gly Pro Ser Gly Pro Gly Ser Ser Pro
625                 630                 635                 640

Ser Gln Ser Pro Ser Gly Gln Gly Pro Ser Ser Gln Pro Ser Pro Ser
                645                 650                 655

Gly Ser Gly Gln Pro Gln Gly Pro Pro Ser Pro Ser Gly Gln Pro Pro
            660                 665                 670

Ser Pro Pro Ser Gly Ser Pro Ser Pro Pro Gln Pro Gly Ser Pro Gly
        675                 680                 685

Gln Pro Gln Pro Ser Pro Pro Ser Gln Ser Pro Gly Gly Pro Gly Gly
    690                 695                 700

Pro Gln Gly Pro Pro Ser Ser Pro Gly Ser Ser Gly Ser Ser Gly Ser
705                 710                 715                 720

Ser Gln Pro Pro Pro Pro Pro Ser Gln Gln Ser Ser Ser Gly Gln Ser
                725                 730                 735

Pro Gln Pro Gln Gly Gln Gly Gln Gln Pro Gly Ser Pro Gly Gln Ser
            740                 745                 750

Gly Gln Gln Ser Gln Ser Pro Gly Gly Pro Ser Pro Gln Gln Pro Pro
        755                 760                 765

Pro Pro Pro Pro Pro Pro Pro Gly Ser Ser Pro Gln Ser Ser Pro Gln
    770                 775                 780

Pro Ser Pro Ser Gln Ser Gln Pro Gln Ser Gly Ser Gln Ser Ser Gln
785                 790                 795                 800

Gln Gln Ser Gln Ser Ser Ser Ser Pro Ser Pro Gln Ser Gln Gly Gly
                805                 810                 815

Pro Gln Ser Ser Gly Ser Ser Pro Ser Ser Gly Pro Gln Ser Pro Ser
            820                 825                 830

Pro Gly Gly Pro Pro Pro Ser Gln Ser Ser Ser Gly Gln Pro Ser Pro
        835                 840                 845

Pro Ser Pro Pro Gly Pro Ser Gly Ser Ser Ser Ser Ser Ser Gly Ser
```

```
    850                 855                 860

Gly Ser Gly Pro Gln Pro Ser Pro Pro Pro Gln Ser Pro Ser Gln Gln
865                 870                 875                 880

Ser Gly Ser Ser Gln Ser Ser Pro Ser Gln Ser Gln Pro Gln Pro Pro
                885                 890                 895

Pro Pro Gly Ser Gly Gln Pro Pro Pro Ser Gly Gly Pro Gln Gln Pro
            900                 905                 910

Pro Ser Pro Gln Gln Gly Ser Gln Ser Ser Ser Gln Pro Pro Pro Pro
        915                 920                 925

Gln Ser Ser Ser Ser Gly Gly Pro Gly Gln Ser Ser Gly Ser Pro Gly
    930                 935                 940

Pro Ser Pro Pro Gln Gln Ser Gly Gly Ser Pro Pro Pro Ser Gly Gly
945                 950                 955                 960

Gly Ser Gly Pro Gly Ser Pro Pro Ser Gly Gln Gly Ser Pro Ser Gln
                965                 970                 975

Ser Ser Gly Pro Ser Gly Gly Pro Gly Gly Ser Pro Pro Pro Pro Ser
            980                 985                 990

Ser Pro Ser Pro Ser Gln Ser Ser
        995                 1000
```

<210> SEQ ID NO 12
<211> LENGTH: 3000
<212> TYPE: DNA
<213> ORGANISM: Artificial Sequence
<220> FEATURE:
<223> OTHER INFORMATION: Sequence is produced using the reverse translation tool located at: www.vivo.colostate.edu/molkit/rtranslate/index.html.

<400> SEQUENCE: 12

```
tctcaatctc ctaaaccttc ttctcaatct caatctcaac ctccttcttc taaaaaatct     60

aaacaacaac aacaacctaa atctccttct tcttctcctc aatctcaatc tccttcttct    120

aaaccttctt cttcttctcc tcaacaacct tctaaatctt ctaaatctcc taaacctcct    180

tctccttctc ctcctccttc taaaaaacct aaatctcctt ctaaaccttc tcctaaacct    240

ccttctcctc ctaaatctaa atctcctaaa caacctcaat cttcttctca atctcaatct    300

tcttcttcta aatcttctca acctccttct cctccttctt ctcaaaaacc ttctcaatct    360

caatcttctt ctcaacctaa accttcttct cctaaacctc aatcttctcc tcaaaaacaa    420

tctccttctc aacctaaaaa atctcaaaaa cctaaaaaac aaaaaaaacc tcaacaacct    480

tcttctcctc aacctaaacc tcaatctcaa cctcaacctc ctcaatcttc ttcttctaaa    540

tcttctcctc aatcttctca acaatcttct caatctcctc ctcctcctcc tccttcttct    600

tcttctcctc ctaaatctaa accttctaaa cctcaatctc aaaaacctcc ttctccttct    660

tctaaaccta aatctaaatc ttctcctcaa aaatcttctt ctccttctcc taaatctaaa    720

tctcctcaac ctcctaaaca acaatctcct cctaaacctc ctcctaaatc tcctcaacct    780

aaaccttctc ctccttcttc tcctaaaaaa cctaaacctc ctccttctcc taaatctcaa    840

tcttcttctc aaccttctcc taaatctaaa tctcaacctc cttcttcttc tcaaccttct    900

ccttcttctt ctcaacaatc tcaatctcct caaccttctt ctcaaaaacc tcctcaatct    960

ccttctcaaa aatctaaaaa atcttctcct ccttctcctc ctcctcctcc ttctcctcct   1020

tctcaaaaac aacctcctcc tccttcttct cctaaacctc ctcctcaaca atctcctcaa   1080

aaatctccta aatctcctaa acaatctaaa caatctcctc cttctcaacc ttctcctcct   1140

cctcctcctt cttctcctca acctaaacct tcttctcaac ctaaacctca atctaaacaa   1200
```

cctcaacaac cttctaaatc taaacctcct cctcctcaat ctaaacctcc tcctcaatct 1260
ccttctaaac ctcaacaaca accttctcct cctaaacctc cttctaaacc taaacctcct 1320
cctcaaccta aatctaaatc taaaaaacct aaacaatctc ctaaatctcc taaatctcct 1380
cctaaaaaat cttctcaaaa atcttcttct cctcctcaat ctcctaaaaa acaaaaatct 1440
caatctcctt cttcttctca acctcctaaa cctcctaaac ctccttcttc tcctcctcct 1500
ccttcttctt ctaaacctcc ttctaaaaaa cctcaatctt cttcttcttc tccttctcct 1560
tctcaacaac ctcaaccttc ttctccttct caacctcctc cttcttctcc tcctcctcct 1620
caaccttctc aacctccttc tccttcttct aaaaaaaaac aaaaacaacc tcaacaaaaa 1680
cctcctcaac aacaatctca aaaatctaaa caacaaaaac aacaaaaatc ttctcctcct 1740
ccttcttctt cttctccttc taaaaaacct cctcctcctt cttctcctaa atctcaaaaa 1800
aaaaaacctc cttctcaacc ttctcctcaa ccttcttctt ctcaatctcc ttctcaacaa 1860
tctcaatcta aaccttcttc ttctcctcaa ccttctcctc aacctaaatc tcaatctcct 1920
caatctcaaa aaccttctcc tcaatcttct ccttctaaat ctaaacctcc ttcttcttct 1980
tctcaaccta aaccttcttc tccttctcaa caaccttctc aacctcctaa atcttctaaa 2040
tctaaacaac ctcctcctcc ttctcaacaa ccttctccta aacaatcttc ttcttctcct 2100
aaaaaaaaac ctcctcaacc tcctaaaaaa caatctcaac aaaaacctcc tcctcaacct 2160
cctcctcctt ctcctcctcc tcctcaacaa aaatcttctt cttctaaatc taaacaaaaa 2220
tctaaacctt ctccttctca atcttctcct tctcctcctt ctcctcctcc tcctcaatct 2280
cctaaacaaa aatcttctaa atctcctcct aaacaacctt ctcctcctca acctcaatct 2340
cctaaaaaac aacctcaaaa atctcctcct tctcaatctc cttcttctca atcttctcct 2400
caaccttctc ctcctccttc ttcttctcaa tctcctcctc ctcctaaatc ttctcaatct 2460
tcttcttctt cttctaaacc tcctccttct cctaaacctc ctcctcaacc ttctcctcaa 2520
tcttctcaac ctcaaaaaaa atctcaacct tcttcttcta aatctcctaa acctcctcct 2580
ccttcttcta aacctcctaa acaatcttct cctaaacctt ctcaacctcc ttcttctcaa 2640
tctaaacaac aaaaacaatc taaaaaaaaa tctaaaaaaa aaccttctcc tcctaaaaaa 2700
tctaaacaac ctcaacctca atctccttct aaatctccta aaaaaccttc ttctaaatct 2760
tctaaatctc ctcctaaatc ttctccttct tctccttcta aatctcctcc tcaaaaacct 2820
ccttctcaaa aatcttctaa acctcctcct ccttcttctt ctcaatctaa acctcaacaa 2880
tctcctaaac cttctaaacc ttctcctcct tcttcttctt ctcctcctca acaacaatct 2940
tcttcttcta aacaatctca atctcctcct cctccttctt ctccttctcc ttctccttct 3000

<210> SEQ ID NO 13
<211> LENGTH: 3000
<212> TYPE: DNA
<213> ORGANISM: Artificial Sequence
<220> FEATURE:
<223> OTHER INFORMATION: Sequence is produced using the reverse translation tool located at: www.vivo.colostate.edu/molkit/rtranslate/index.html.

<400> SEQUENCE: 13
aaacctcctc ctaaatctca aaaaaaatct tctaaaaaac ctcaacaaaa atcttctaaa 60
tctcctaaat ctaaaaaatc ttctaaacct caaaaacaaa aatctaaacc tcctaaatct 120
aaatctcaac ctcctaaaaa atctaaacaa ccttctaaaa aaaaaaaacc ttctaaaaaa 180
cctcctaaat ctaaacaaca aaaacctaaa aaaaaatctc cttctcctcc tcctcaatct 240

-continued

```
ccttcttcta aaaaaaaacc ttcttcttct cctaaaccta aaaaaaaacc ttctcctcct    300
tcttctaaat ctaaaaaacc taaatctcct tctccttcta aatctaaaca acaatctcct    360
caaaaatctc cttctcctaa atctaaacaa caatcttcta aaaaatctcc ttcttcttct    420
caatctcctc ctaaatctaa aaaatcttct aaaaaatctt ctaaaaaatc tccttctcaa    480
aaaaaacaac ctcaacctca atcttctcct cctaaacctc ctcaacctaa accttctcct    540
aaaccttctt cttctcctcc tcctaaacct caacaacctc ctaaacctcc ttctcaaaaa    600
tctcctccta aacctaaacc ttcttctcct tctcaaaaaa aatcttctca aaaatctaaa    660
caaaaacaac ctcctcctcc ttcttctaaa ccttctaaat ctaaacctaa aaaaaaaaaa    720
tcttctccta aacaacctcc tccttctcct caacaatctt ctaaacctaa aaaatcttct    780
tcttctcaaa aatctcctcc tcaaaaacaa caaaaacctt cttctcaatc ttcttctcct    840
cctcctcaat ctaaatctaa aaaatcttct cctaaaaaat ctcctcctaa atctaaacct    900
tctcaacctc aaccttcttc ttctaaacct cctaaatcta aatcttctca acaatcttct    960
tcttctcaaa aaaaaccttc tcaacaacaa ccttcttctc ctaaaaaacc tcaatctcct   1020
ccttctcctc ctcctaaacc tcctcctcct caatcttctt cttctaaatc tcctcctaaa   1080
aaatctaaat cttctcctaa acaacctcct tctcctcctt ctcaatcttc tcaacaatct   1140
tctaaatctt ctccttctcc tcctaaaaaa aaaaaacaac ctaaacaatc taaacctaaa   1200
caacaacctt ctaaacaatc taaaaaaaaa cctcctcctc aacctaaaaa atctcctcaa   1260
aaacaaaaat ctcaacctaa aaaacaacaa caaaaacctt ctcctcaacc taaatcttct   1320
tctaaatctt ctaaaccttc ttctcctaaa aaaaaacctc aatcttctcc tcctcaacaa   1380
aaacaacctt ctaaacctcc tcaatctcct tctcctcaaa aatctcaaaa atctcctcaa   1440
cctccttctc ctcctaaatc tcctcaacct cctaaaaaat ctaaatcttc ttcttctaaa   1500
tctaaaaaat cttcttctca aaaacctcct cctcaaccta aaccttctca acctaaatct   1560
cctccttctc aatctaaaaa accttctaaa cctccttctc ctccttctaa acctaaacaa   1620
cctcaatctc ctaaatctaa acaacaatct tctcctcctt cttctccttc taaatctaaa   1680
caaaaacctc ctaaacaatc ttctcaacct tctcaacctc ctcctaaatc tccttctcct   1740
tcttctccta aatctaaacc taaacctaaa ccttctcaat cttctaaatc ttctaaaaaa   1800
aaaccttcta aacctccttc tcaatctcct tctcaaaaaa aatcttctaa atctcctcct   1860
cctaaatcta aacctcctcc ttctcaatct cctaaatcta aaaaaaaatc tccttctcaa   1920
aaatctaaaa aaaaaaaaca aaaaaaacct aaacctaaac ctcctccttc tcaaaaaaaa   1980
caacaaaaat cttcttctcc tcctccttct aaaaaatctt ctccttctaa atctaaacct   2040
ccttctcctc cttctaaaaa atcttctaaa tctcctcctc ctaaaaaaaa acctcctcct   2100
caatctcctt ctcctaaaca atctcctcaa cctaaaaaac cttctaaatc ttctcctcct   2160
caacaatctc ctaaaaaaaa atctcctaaa caacctcctt ctaaacctaa acctaaacct   2220
cctcctaaac aaaaaccttc ttctaaacct caaaaatctt cttctaaatc taaaaaacct   2280
aaacctcctt ctaaacaatc tcaaaaaaaa tctaaacaac ctcaatctcc tcaaccttct   2340
tctaaacaaa aacctaaacc taaacaatct tctcctccta aatctaaatc taaaaaaaaa   2400
cctcctcaaa aaaaaccttc tcaacctaaa tcttctaaac cttcttctaa acctaaaaaa   2460
aaacaacctc ctcctcctca acctaaacct cctcaaaaaa aatctaaaca atcttctaaa   2520
tctcctcctc ctccttctaa aaaatctaaa ccttctaaaa aatctcaaca acaaaaatct   2580
caatctcctt ctcctaaatc ttctcctcct tctcctaaac ctaaaaaatc tcctcctcct   2640
```

```
tcttcttctc cttcttcttc tccttcttct cctaaacctc cttcttctca atctcaaaaa   2700

aaacaatctc ctaaacaaca accttctaaa caaaaatctt ctcctcctaa aaaatctaaa   2760

aaacctaaaa aacctcctcc ttctccttct tctaaaaaaa aaaaacctaa aaaatctaaa   2820

tctaaaaaac ctccttctcc taaacaaaaa aaatctaaac aaaaatctaa acctaaacct   2880

cctaaacaac ctcaatcttc tcaacctcct aaacaaccta aacctcaaca acaatctcaa   2940

tcttctcaac ctcctcaaca atctcaaaaa cctcaaaaac ctaaatctcc tcaacaatct   3000
```

<210> SEQ ID NO 14
<211> LENGTH: 3000
<212> TYPE: DNA
<213> ORGANISM: Artificial Sequence
<220> FEATURE:
<223> OTHER INFORMATION: Sequence is produced using the reverse translation tool located at: www.vivo.colostate.edu/molkit/rtranslate/index.html.

<400> SEQUENCE: 14

```
caatcttctt ctcctcctaa atcttcttct caatctaaat cttcttcttc ttcttcttct     60

tctccttctc ctaaatctcc ttcttctcct tctaaacctc ctcctccttc taaaaaaaaa    120

cctaaatcta aaaaaaaaca atcttctcct aaatcttcta aacctaaaaa acctaaacaa    180

aaaaaatctc ctcctcctca aaaacctaaa aaatctcctt ctaaacctaa atctaaacct    240

tcttcttcta aaaaaaaaaa atctcaacaa caatcttctc aaaaatctca atctaaacaa    300

cctaaaaaac ctcaaccttc tcctaaaaaa cctaaatctc ctaaaaaacc tcctaaacct    360

caacctaaat cttctcctaa acaatctaaa caaaaacctt ctaaaaaaaa accttcttct    420

aaacctaaat ctaaatctaa aaaaaaatct caaaaaccta aacaatctaa aaaatcttct    480

tctaaacctc cttctaaatc taaaaaaaaa caacctaaac ctaaaaaaaa atctaaatct    540

tcttcttcta aatcttctaa atctccttct aaatctaaat ctcctcaatc ttctaaatct    600

tctcctccta aaaaacctaa acctaaaaaa cctaaaccta aatcttctaa atctcctaaa    660

tctcctccta aaaaaaaacc tcaatctcaa aaacaaccta aatctcaatc tcctcaacct    720

caaaaaaaac ctaaacaatc ttctaaacaa aaacctaaat ctaaaaaatc tcctaaaaaa    780

cctcctaaaa aatctaaacc taaatctcct cctcctccta aaaaacctaa acctaaaaaa    840

tcttctaaac aacctaaatc tcaatcttct caaaaaaaac ctaaacctcc tcctccttct    900

cctcctaaac aaaaacctca aaaatcttct tctcctccta aacaacaatc taaaaaacct    960

tctcctcctc aaaaacctaa acctaaatct tctccttctc cttctaaatc ttctcaatct   1020

aaaaaaaaaa aacctaaaaa acctaaacaa tctcctcctc aaaaacctcc ttctaaacaa   1080

tctcctcaaa aacctaaatc ttcttctcct cctaaaaaaa aaaaatcttc taaaaaacaa   1140

aaaaaaaaac aaaaaaaaca aaaatcttct caatctaaac cttctcaaaa acctccttct   1200

aaacctaaat cttcttcttc taaaaaaaaa caatctaaaa aaaaaaaacc tcctcaaaaa   1260

tcttctaaaa aacaacaatc tcctcctaaa caatctccta aaccttctcc taaaaaaaaa   1320

aaacctaaaa aaaaacaaaa aaaatctcct aaacaatctc aacctaaaaa acctaaacct   1380

tctaaacctc aaaaatctca aaaaaaatct ccttctccta aacctcctcc tcaacctaaa   1440

cctcaaaaaa aatctcctcc taaacctaaa cctaaatctc cttctcctcc tccttctcaa   1500

aaacctaaaa aaccttctaa acctcaacaa tctcctcaaa aaaaacctcc tcctaaatct   1560

caaaaaaaac ctaaacctcc taaaaaaaaa tctaaatctt cttctcctcc tcaatctaaa   1620

caacaaaaaa aaaaaaaaaa aaaatctcct aaatctaaaa aatctaaaca acctcaacct   1680
```

```
aaacaaaaaa aaaaatctaa acctaaatct ccttctcaaa aacctaaaca atcttcttct   1740

aaacaaaaaa aatctcctaa acctaaacct tctcctaaat cttctaaacc tcaacctaaa   1800

aaaaaaaaaa aaccttctaa aaaaaaaaaa aaaaaaaaac aaaaacctcc tcctcaatct   1860

aaaaaaccta aatctcctcc tcctaaacct aaacctaaat cttcttctaa aaaacctcct   1920

cctaaacctt ctaaacctca atctaaaaaa caatctaaat ctaaaaaaaa acctcctaaa   1980

caaaaaaaaa aacctaaaaa atctcctaaa aaaaaaaaaa aacctccttc ttctaaatct   2040

tctcctaaat ctcctccttc tcaacaatct cctcctcctc ctaaacaatc taaacaacct   2100

ccttctcaat ctaaaaaacc tcctaaacct cctaaaaaaa aatcttctaa aaaaaaaaaa   2160

aaatctaaaa aacctcaaaa acaacctaaa aaaaaatctt cttctaaaca atctaaatct   2220

aaacctcctt ctccttctca acctccttct ccttctaaac ctccttctcc taaaaaaaaa   2280

tctccttctc aatctaaacc taaacaaaaa tctccttcta aatcttctaa atctaaacaa   2340

tctaaacctt ctaaacaaca acctaaacaa aaacctcaat cttctcaaaa acctaaatct   2400

cctaaatcta aaaaaaaatc tcaaaaaaaa caatcttctt ctcctcctaa atctaaatct   2460

caacaaccta aaccttctca aaaaaaacct cctaaacaac aatcttctaa atctcctcaa   2520

aaatcttcta aacaaaaacc ttctaaacct tcttctccta aacctcaatc taaacaatct   2580

aaacaacaaa aaaaaaaaaa acaatctaaa caacctccta aacaaaaaaa accttctaaa   2640

tctaaaaaac ctcctcctaa acctcctcct aaatctaaac ctaaacaaaa aaaacctcaa   2700

aaaaaaccta aatcttctaa aaaacctcaa caaccttctc cttcttctcc ttcttctaaa   2760

tcttctaaaa aatctaaatc taaacaaaaa cctcctcctc aacctcctcc ttctcaaaaa   2820

aaaaaaaaac ctcctcctaa atctcaaaaa aaacctaaaa aaaaaaaatc ttctccttct   2880

aaaaaaaaac ctcctaaaaa aaaatctcct tctcaatctt ctcaaaaatc taaatcttct   2940

tctcaatctc ctcctcaaca acctcctcaa aaacctaaaa aatctaaaca aaaaaaaaaa   3000
```

<210> SEQ ID NO 15
<211> LENGTH: 3000
<212> TYPE: DNA
<213> ORGANISM: Artificial Sequence
<220> FEATURE:
<223> OTHER INFORMATION: Sequence is produced using the reverse translation tool located at: www.vivo.colostate.edu/molkit/rtranslate/index.html.

<400> SEQUENCE: 15

```
tcttctaaac ctaaaaaatc tcctccttct aaaaaacaat ctcaatctaa aaaatctaaa     60

cctaaaaaaa aaaaatctca aaaacctaaa aaatcttctc ctaaaaaaaa atctaaatct    120

tctaaaaaac cttctcctcc tcaaccttct aaacaaccta aacaacaatc tccttctaaa    180

caatctaaat ctcctaaatc tcaaaaacct ccttctcctc ctaaaaaaaa acaaaaaaaa    240

ccttctaaac aacctaaatc tcctaaacct cctaaatcta aatctcaaca acctaaacct    300

aaacctcaac aacctaaaaa aaaacctaaa ccttctaaac ctcctcctcc ttcttctcaa    360

aaacaacaaa aatctaaatc tccttctcaa aaaaaaaaaa aaccttctaa aaaacctaaa    420

aaaaaacaac ctaaacaatc tccttcttct aaaccttctt ctcaacctaa acaacctcct    480

caaaaaaaaa aaaaacctaa acctaaaaaa aaaaaaaaac aaaaacaacc taaaaaacct    540

aaaaaaaaaa aatctcctaa aaaaaaacct aaacctccta aatctaaaaa aaaaaaacct    600

aaatcttcta aaaaatctaa acctcaaaaa ccttctcctc ctaaatctcc taaacctaaa    660

cctaaaccta aaaaaaaacc taaatctaaa aaatctaaat cttctaaacc taaacctcct    720
```

tctaaaaaaa aacctcctcc ttctcctcct tcttctccta aacaaaaatc taaatctcct 780
cctaaaaaaa aacctaaaca aaaacctaaa caaaaatcta aatcttcttc tcctcaacct 840
aaacctcctt cttctcctaa aaaaaaaaaa aaacaatcta aatctaaaaa accttctaaa 900
aaatctcctc ctaaaaaaaa aaaatctcaa caaaaatctt ctaaaaaacc taaaaaacct 960
aaaaaatcta aaaaatcttc taaaaaaaaa tctaaacctc aatctaaacc taaatcttct 1020
aaaaaaaaaa aatcttcttc taaatcttct cctaaaaaac ctaaacctca acaacctaaa 1080
aaaaaaaaac aacaaaaaaa aaaaaaatct tctaaaccta aacaaaaaaa atctcaaaaa 1140
aaaccttcta aaaaaaaacc taaaaaacct aaacaaaaaa aatctaaaaa atctcctcct 1200
aaaaaacaat ctaaacaacc tcctcaaaaa aaatctaaaa aaaaacaaaa acctccttct 1260
caaaaaaaat ctcaatcttc tcctaaacct aaacctcctc aaaaacctaa aaaaaaatct 1320
cctaaacctc ctaaaaaacc tcaaaaaaaa cctaaatcta aacaatcttc ttctaaacct 1380
tctaaacctc ctcctcctaa aaaacctcct aaaaaaccta aacctaaaaa aaaaaaaaaa 1440
aaatctaaaa aatcttctaa aaaaaaaaaa caaccttctc ctaaaaaacc taaatctaaa 1500
aaaaaaaaaa aatcttctaa accttctaaa ccttctcaac aaaaatctcc taaatctaaa 1560
ccttcttctt ctcctcaatc taaacaacct aaacaatctt cttcttcttc taaaaaacct 1620
aaaaaacctc cttctaaatc taaacaacct tcttctaaat ctcctaaatc tcctcctcct 1680
aaaccttctc aaaaacctcc tcctcaaaaa aaacctaaac aaaaaaaatc taaaaaacct 1740
cctaaaaaaa aaaaaaaacc tcaaaaacct aaaaaatctt ctccttctcc tcctccttct 1800
cctaaacaaa aaaaaaaaca acctccttct aaacaaccta aatctaaaaa atcttctcaa 1860
aaaaaatctt ctaaatctaa aaaaaaaaaa aaaaaaaaac ctcctaaaaa atctaaatct 1920
cctccttctc aatctaaatc taaaccttct cctcctccta aaaaacctaa aaaacaatct 1980
tctcaacaat ctaaatctca acaatcttct aaacctaaac ctaaacctaa aaaacctcct 2040
cctaaacaat ctccttctcc ttcttctcaa aaaaaaaaaa aacctaaatc taaaaaacct 2100
tcttctcctt cttctcctaa atcttcttct ccttcttctt ctccttctaa atcttctaaa 2160
caaaaacctt cttctccttc taaacctaaa aaacctaaaa aaaaacctaa aaaaaaacct 2220
aaaaaaccta aaaaacaacc taaacaaaaa cctaaaaaac ctcctccttc taaaaaacct 2280
aaacctcctt ctaaatctca atctaaaaaa cctaaacaaa aaaaatcttc tcctaaaaaa 2340
aaaaaatcta aaaaatctaa aaaatctaaa caacaaaaac aacaaaaaaa aaaatctcaa 2400
aaaaaatcta aatcttctcc tcctaaatct aaaaaacaaa aacaatctaa aaaacctaaa 2460
caacctaaaa aaaaacaatc taaatctcct aaaaaacaaa aaaaacctaa atcttctcct 2520
tctcaaaaac aacaacaaaa aaaaaaaaaa caaccttcta aatcttctaa aaaacctaaa 2580
caaaaaaaaa aatctaaaca atctaaacct aaacaaccta aaaaatcttc tcctcctaaa 2640
tctccttcta aacaatctaa aaaatctcct tctaaatctc aaaaacctca atctaaaaaa 2700
tctcctaaat ctaaaaaaaa atcttctaaa aaaaaaaaaa aaaaaaaaaa acctaaaaaa 2760
cctaaaaaaa aacctaaaaa atctaaatct tcttctcaaa aaaaatctaa acaacctaaa 2820
tctccttctc aaaaatcttc taaaaaaaaa aaacctaaac aatcttctaa aaaaaaacaa 2880
aaaaaacaaa aacaaaaaaa aaaacaacct tcttctaaac ctcaacctaa aaaaaaacaa 2940
cctaaaaaaa aacaaaaaaa acctaaaaaa aaaaaatctc ctaaatctcc taaacctaaa 3000

<210> SEQ ID NO 16
<211> LENGTH: 3000

<212> TYPE: DNA
<213> ORGANISM: Artificial Sequence
<220> FEATURE:
<223> OTHER INFORMATION: Sequence is produced using the reverse
translation tool located at:
www.vivo.colostate.edu/molkit/rtranslate/index.html.

<400> SEQUENCE: 16

```
aaaaaaaaac aacctaaaaa atctcaacaa aaaaaaaaaa aaaaaaaaca atctaaacct     60

aaacaaaaaa aacctccttc ttctaaacct cctaaacaaa aaaaaaaaca acctaaaaaa    120

tctccttcta aatcttcttc taaaaaaaaa caaaaatctc ctaaacctca aaaaaaacct    180

aaaaaaccta aaaaacctaa aaaatctaaa aaacaacctc aacaacctcc ttctaaacct    240

tctcctcaat ctaaatctaa acaacctcaa caaaaaaaac ctcctaaacc taaacctcct    300

aaaaaaccta aaaaaaaaaa acaaccttct caaaaacaat ctaaacctcc taaatctcaa    360

tctcaaaaaa aatcttctaa acaaaaatct ccttctaaac ctaaacaaaa atcttctaaa    420

aaaaaaaaaa aaaaaccttc ttcttctcct tctaaatcta aaaaaaaaaa acctaaatct    480

aaacctccta aaaaatctaa acctaaaaaa aaaaaaaaat ctcaatctaa aaaacctaaa    540

aaaaaaaaac ctaaacaaca acaaaaacct aaaccttcta aacaacaaaa acctaaacct    600

tcttctaaaa aatcttctcc taaaaaaaaa cctaaacaaa aacctaaacc tcaacctaaa    660

cctaaaaaac ctaaacctcc taaacctaaa caaaaaaaaa aatctaaacc taaacctaaa    720

tctcctaaaa aaaaacaaca acaacaacct aaacctcctc aaaaatctcc taaaaaatct    780

cctcctaaaa aacctaaacc taaaaaatct tctccttcta aatctccttc taaacctaaa    840

aaacaaaaac ctaaaaaacc ttcttctcaa aaaaaaccta aatctaaatc tcctcctaaa    900

aaacaatcta aaaaatctaa atctaaatct aaaaaaaaat ctccttcttc taaaaaatct    960

aaacctaaaa aatcttctcc taaaaaacct aaatctaaaa aacaatctaa atctaaatct   1020

caaaaaccta aatctaaaca atcttctcct aaacaaaaaa aaaaatctca aaaatctaaa   1080

cctcaaaaat ctaaaaaaaa atcttctcct aaaaaacaaa aatctaaaaa aaaaaaatct   1140

cctaaaaaac cttctaaacc tcctaaaaaa aaacctccta aatctaaaca atctaaaaaa   1200

aaacaatctc ctaaacctaa acctccttct ccttctccta aacctaaaaa aaaatctaaa   1260

aaaaaaaaaa aaaaacaacc ttcttctaaa aaacaaccta aaaaaccttc taaaaaaaaa   1320

aaacaatctc cttctaaaca acctaaatct aaatcttcta aaaaaaaacc tcctaaaaaa   1380

caacctaaaa aacctaaaaa aaaaaaacaa tcttctaaaa aacctaaaaa atctcctcaa   1440

aaaaaatcta aaaaacctca atcttctcct aaaaaatctc cttctaaaca acctaaaaaa   1500

aaaaaaccta aaaaacctaa aaaacctaaa aaaaaaaaac ctcaatcttc tccttctaaa   1560

cctcctccta aatctcaatc taaacaaaaa tctcctccta aatcttcttc taaaaaaaaa   1620

caaaaaaaac ctaaacctaa aaaaaaaaaa aaaccttcta aaaaaaaacc tcctccttct   1680

aaaaaaccta aaaaatctaa aaaatctaaa tctaaaaaaa aatctaaaaa aaaatctcct   1740

cctaaaaaat ctaaaaaaaa acaacctaaa cctcctaaaa aatctaaaaa aaaatcttct   1800

aaacaatcta aacctaaaaa atctcctaaa cctaaatcta aaaaaaaatc taaaaaacaa   1860

aaatcttctt ctaaaaaatc tcctcctcct aaatctaaac ctcctaaacc ttctcaacct   1920

cctaaatcta aaaaaaaaaa acctccttct aaaaaaaaac ctaaaaaaca aaaatcttct   1980

caaaaaccta aatcttctca aaaaaaaaaa cctcctaaac ctaaaaaaca acctaaatct   2040

aaaaaaccta aaaaacctaa aaaacaacaa caaaaaaaac ctcctaaaaa aaaaaaaaaa   2100

aaaaaaaaaa aaaaacctaa acctaaaaaa cctcctaaac ctcaatctaa atctaaaaaa   2160
```

aaaaaaaaat ctcctccttc tcctccttct cctaaaaaaa aaaaaaaaca aaaaaaaaaa 2220
tctaaaaaaa aaaaacctaa aaaaaaacct caaaaaaaat cttctaaaca aaaaaaaaaa 2280
aaaccttctt cttctaaacc taaatctcaa tctaaaaaat cttctaaaaa acctaaacaa 2340
tctaaacaaa aaaaatctca atctaaaaaa tcttcttcta aatctaaacc tcaaaaaaaa 2400
tctaaaaaaa aaaaaaaaaa aaaacctaaa aaaaaaaaaa aaaaaaaatc taaatctaaa 2460
tcttctcaat ctcaaaaaaa aaaaaaaaaa tctcctaaaa aaaaaaaaaa aaaatctaaa 2520
aaaaaaaaat ctaaaaaacc tcctaaacct aaaaaacaat ctaaaaaatc taaatctaaa 2580
cctcctcctt ctaaacctaa atcttctaaa tctaaaccta aaaaacctcc taaaaaaaaa 2640
aaacaaaaaa aaaaacaaaa atctaaacct tctaaaaaat ctccttctaa acctccttct 2700
aaaccttcta aacaaaaaaa aaaatctcaa aaaaaacaac ctcaacctcc taaaaaacaa 2760
cctcctaaat ctaaacctaa acctcctaaa cctcaaaaat cttctaaaaa aaaaaaaaaa 2820
ccttctaaaa aacctcctaa aaaaaaatct aaaaaacaaa aaaaaaaaaa atctcaatct 2880
caaaaaaaat cttcttctca aaaacctaaa tcttctaaat cttctcaaaa aaaacctaaa 2940
aaaaaatcta aatcttctaa acaaaaatct aaaaaacaaa aatctaaaaa aaaacctaaa 3000

<210> SEQ ID NO 17
<211> LENGTH: 3000
<212> TYPE: DNA
<213> ORGANISM: Artificial Sequence
<220> FEATURE:
<223> OTHER INFORMATION: Sequence is produced using the reverse translation tool located at: www.vivo.colostate.edu/molkit/rtranslate/index.html.

<400> SEQUENCE: 17
gaagaacctt ctccttctcc tcctgaatct tcttctgaac ctcctcctcc tcctcctcct 60
caacctcctg aacctcctca acaatctgaa caacctcaag aatcttctcc ttctcaatct 120
caatctgaac cttctgaaca acaacaagaa tcttcttctt ctgaacaaga atcttcttct 180
cctcctgaat ctcaagaaga acctcaatct gaacaacctt cttctcctcc tgaacctcaa 240
cctcaatctc aatcttctca acctcctcct tctgaatctc cttctcaaca atctgaacct 300
cctcctgaac aatctcaatc tccttcttct ccttcttctt cttctcaaca atctcaacct 360
ccttcttctg aaccttctga accttctcct tcttctcctc aatcttctcc ttctccttct 420
cctcaacaat ctcctgaaga atctgaatct caacctcaat ctccttcttc tcaatctcct 480
cctcaacctc cttctgaacc ttctcctcct caatcttctg aacctcctga acctccttct 540
tctgaacctc aaccttctcc ttcttctcct cctcaacctg aatctccttc ttcttcttct 600
tctcctcctt ctcctccttc tcctcaagaa ccttctcctg aacaacctcc tcctcctcct 660
cctcctcaat ctcctgaatc tcctccttct gaacctcctc aatctcctcc tgaacaagaa 720
cctgaacaac ctcctgaacc tgaatcttct cctcctcaat ctcaatcttc tgaacctcaa 780
tctcaacctg aacctcaatc ttctgaacaa tctgaagaat ctgaatctca acaagaacct 840
ccttcttctc ctgaacctcc ttctcctgaa gaagaacaac cttctccttc ttctccttct 900
cctcctcaat ctcctcctga acctcctcct tcttctgaac ctgaatcttc tccttcttct 960
gaatctcctt ctgaacaatc tcctcctgaa ccttctgaac aatcttctca atctccttct 1020
ccttctcctc ctcaacaaga acaatctcct ccttctcaat cttctcctga acctccttct 1080
tctcctgaac ctgaagaatc tcctcctcct gaacctgaat cttcttcttc tccttcttct 1140
tctcaacctg aagaacaacc ttcttctcct tctcctcctt ctcctccttc ttcttctcaa 1200
tcttctcctt cttctcaatc tccttcttct cctgaagaat ctccttctcc tcctcctcct 1260
cctcctgaat ctgaaccttc tcctcaacaa ccttctcctc ctcaacaaga acctcctcct 1320
tctcaatctt ctccttctca acaatctcct cctcctcctt cttctcctcc tccttctgaa 1380
caacctcctc aagaacctca acctccttct caatcttctc aacctcctga accttcttct 1440
caatctgaac cttctcctcc tcctcaatct cctcctcaac ctgaatctcc tcaaccttct 1500
tcttcttctc aaccttcttc tgaacctcct tctccttctt cttctcctcc tgaaccttct 1560
ccttctcctg aacaacctcc tccttctcct tctcaagaag aaccttctca agaaccttct 1620
caatctgaat cttctgaaca atctcaatct cctccttctc cttctgaatc ttctcaatct 1680
cctcctcaat cttcttcttc tcctcaatct cctgaacctc aacctcctcc ttctgaatct 1740
caagaatctc aacctcctcc ttctgaatct caaccttctc ctgaagaatc ttctccttct 1800
tctcaatctg aacaaccttc tcaatctcaa gaacctcaac aatctcctcc tcaaccttct 1860
cctgaacaac ctgaatctga acaagaatct ccttctcctt ctgaagaatc tgaatcttct 1920
tcttctcaat ctcctcctcc ttctcctcaa gaaccttctc ctccttctga atctcaatct 1980
tctccttctt ctcctcctca accttcttct tctcaagaat ctccttcttc tcaacctcaa 2040
cctcaatctc aatctcctcc tcaacaacct caacaatctc ctcctccttc tcctcctcct 2100
caacaatctg aagaacaaga acaagaatct gaacctcaag aacctcaacc tcaatcttct 2160
cctgaatctc cttcttctga atctgaatct gaatcttctc ctgaacaacc tcctcaacct 2220
cctccttctc ctgaacctcc tcctccttct ccttctcctt ctcctccttc tgaatctcaa 2280
ccttctcaac ctcaaccttc ttcttcttct gaatctcctg aagaatctcc tcaacctcct 2340
cctgaagaat ctccttcttc ttcttcttct gaagaacctc ctcaacctga agaagaacaa 2400
tcttctgaac cttcttctca atctccttct tcttctcctt ctccttctca atctgaatct 2460
caatctcaat cttcttctga atcttcttct tctgaatctg aatctcaatc tcctgaacct 2520
gaagaacctg aacctccttc tcaagaatct cctcctgaac aacctcaaca agaacaacaa 2580
cctgaagaat cttcttcttc ttcttcttct cctcaatctg aacctcctga agaaccttct 2640
cctcaacaac aacaatcttc ttcttcttct cctgaatctt ctcctcctcc tgaacaagaa 2700
caacctgaac aatctcctca acctccttct caatctcctc aatcttcttc tcaagaatct 2760
tctgaacctc aacctgaaca acaatctcct gaagaagaac cttctccttc tcaatcttct 2820
tcttcttctc cttctcctcc tcctcctgaa caatctgaac aacctgaacc tcctgaatct 2880
cctgaacctc aacaacaatc tcctcaacct ccttcttctc aagaacctga agaacctgaa 2940
cctcaatctc ctcctgaatc tgaacctcct gaagaagaat ctcaatctcc tcaacctcaa 3000

<210> SEQ ID NO 18
<211> LENGTH: 3000
<212> TYPE: DNA
<213> ORGANISM: Artificial Sequence
<220> FEATURE:
<223> OTHER INFORMATION: Sequence is produced using the reverse
translation tool located at:
www.vivo.colostate.edu/molkit/rtranslate/index.html.

<400> SEQUENCE: 18
gaacaacctg aacctccttc tgaatctcct tctccttctc ctccttcttc tgaatcttct 60
cctcctcctt cttctgaacc ttcttctcct caatctcaat ctcctgaaga agaaccttct 120
caatctcaac cttctgaatc ttctcctgaa ccttctcctg aacaatcttc tccttctgaa 180
gaagaacaac ctcctgaatc ttctcaatct caagaatctc aagaacctcc tgaatctcct 240

-continued

```
cctcaacaac cttctcctcc ttctcaagaa tcttctgaac aagaatctcc tgaacaagaa    300
gaatctgaac ctccttctga agaacctgaa cctccttctg aatcttctga agaagaacaa    360
gaacaatctc ctcaatctcc ttcttctgaa cctgaacctg aacaatctca agaatctcct    420
tcttcttctg aatctccttc tcctgaagaa tctcctcctc aacctcctga acctcctgaa    480
tctcctcctc cttctcctga acaagaacaa caacctgaag aagaatctcc tcctcaacct    540
gaatcttctc cttctgaatc ttcttctcct gaatctcctc aagaacctcc ttcttctcct    600
cctcctgaat cttctgaaga agaagaatct caagaatctt ctcctcaaca atctgaagaa    660
caatcttctt ctccttctcc ttctcaatct gaatctcaac aagaatctcc tgaacctcct    720
tctcaacctc cttcttcttc tgaaccttct tctccttctc cttctcctga acctgaacct    780
caacaacctc aacaacaatc tcaacctgaa tctccttctc cttctcctca acaaccttct    840
caaccttctg aagaatctcc tgaatctcct gaacctcctt cttctgaacc ttctgaacct    900
tctgaagaac ctgaatctga acaagaacct tcttctcctc ctgaatcttc tgaacctgaa    960
caatctcaag aagaacctga acctgaacaa tctcaatctg aatcttctcc tgaagaatct   1020
cctgaatctt ctgaacaaca acaagaacct gaacctcctt ctccttcttc tcaatctcct   1080
ccttcttctc ctccttcttc tgaacctcct tctcctcctg aaccttctcc ttcttctgaa   1140
tctcctgaac aacaacaaga agaacaacct tctgaagaac ctcaatcttc ttctgaagaa   1200
caatctcaat cttctgaacc tcctgaacct tctcctcaat cttctccttc tcctcaatct   1260
gaacctcctg aacaagaaca agaagaacct gaacaatctg aacctcaacc tgaacctcct   1320
gaacaatctc ctgaaccttc ttcttctcct gaacaacaac ctgaacctcc tcctcaatct   1380
tcttctcctc cttctcaaga agaatcttct cctcctgaag aatcttctcc tgaagaatct   1440
tctgaagaac cttcttctga acaacaacaa gaaccttctt ctcctcaaga acctgaacct   1500
tcttctcaac ctcctgaacc tcctcaacaa cctgaacctg aaccttctga acctcctcct   1560
tctcaatctg aacctcctcc ttctcctcct gaagaacaac aatcttctcc tcctgaacct   1620
gaacctcctc ctgaatctcc ttctcaagaa gaacctcctt cttcttctca agaagaacaa   1680
caagaacctg aatctcaaga acctgaagaa tctcaacctg aacctccttc tcctcctcaa   1740
cctgaagaag aatctcctca atctgaagaa cctccttctc cttctcaacc ttctccttct   1800
gaagaacaat ctgaaccttc tcaacaacaa gaaccttctc aaccttctga atctcctgaa   1860
tctcctcaag aatctgaaca agaacctgaa gaacctgaat cttctcctga agaagaatct   1920
ccttctcctc aatctcctcc ttcttctcct cctcctgaat ctgaagaaca acctgaagaa   1980
caacctcctc aacaatctcc tgaacctcct ccttcttctc ctgaatctcc tgaatctgaa   2040
cctgaagaat ctcctcctga agaatctgaa gaacaacctc aacaaccttc tcaagaagaa   2100
cctcctgaat ctcaagaatc ttcttctcct caatcttctt ctgaagaatc tcctcctcct   2160
caagaatctg aacaacctga acctgaatct gaacaagaac ctcctcctga acaacaacct   2220
gaacaatctg aacaatcttc tgaacaacaa cctcctcctg aatcttctca acctccttct   2280
tcttcttctg aatctgaaga agaagaagaa tcttctgaac aagaaccttc ttcttctgaa   2340
gaacctgaat cttctgaatc ttcttctgaa caatcttctg aatctgaaga atctgaagaa   2400
gaacctcctc aacaacaaga agaatctcct ccttctgaag aagaagaaca acaacaacct   2460
cctcctgaac ctgaatctga atctcctgaa caatctcaac cttctgaacc ttctccttct   2520
tctgaatctc aagaagaacc tcaagaacct tcttcttctc cttctcctga agaacctcaa   2580
gaagaatctg aagaatctcc tcctgaatct cctgaatctt ctcaaccttc tccttcttct   2640
```

```
caagaacctc ctgaatctga agaatctcaa cctgaacaag aatcttctcc tgaagaacct   2700

gaacctcctc ctcctgaacc tgaagaacct cctcctcctc cttctcctga acctgaagaa   2760

gaagaacaac ctcaaccttc tcaacaatct tcttctcaag aagaagaatc tgaatcttct   2820

gaagaacctt cttctgaacc ttcttctgaa cctgaagaat cttcttcttc ttctccttct   2880

tctgaacaac aatctgaatc tcaagaagaa cctgaagaag aatctgaaga acctcctcct   2940

tcttctgaat ctcctgaaga agaagaagaa ccttctgaac ctcctgaatc ttctgaacct   3000
```

<210> SEQ ID NO 19
<211> LENGTH: 3000
<212> TYPE: DNA
<213> ORGANISM: Artificial Sequence
<220> FEATURE:
<223> OTHER INFORMATION: Sequence is produced using the reverse translation tool located at: www.vivo.colostate.edu/molkit/rtranslate/index.html.

<400> SEQUENCE: 19

```
tctcctgaac aacctgaacc tcaacctgaa cctgaacaag aatctgaacc tgaaccttct     60

gaacctcctc cttctcaaga agaagaatct gaagaagaag aacaatctga acaacctgaa    120

gaagaatctt ctgaaccttc tcctgaatct tctccttctc ctcaagaacc ttctcctcaa    180

caagaacctc cttctgaacc tcaacaagaa tctgaacctt ctcaatctcc ttcttctgaa    240

tctgaacaat ctgaagaaca agaacctcaa gaagaatctg aatctgaaga atctcctgaa    300

tcttctcctt cttctgaacc ttctgaagaa gaatctgaac aatctgaatc ttctgaagaa    360

gaagaacctc cttctcctcc ttctcctgaa gaagaatctc ctgaatctca agaacaacaa    420

gaacctgaac aacaatctga acctgaagaa gaatcttctt cttctccttc tcctgaacct    480

tctgaagaac ctcctcctga atctgaacct tctgaagaat ctcctccttc tgaacaatct    540

gaacctgaac ctcctcctga atcttctgaa cctcctcaac aagaacaaga atctgaagaa    600

tcttcttctc ctcctgaatc tgaacctcct gaacaatctt ctgaacctga agaagaacaa    660

caatctgaag aagaagaatc tcctgaagaa gaatcttctg aagaatcttc tcctgaacaa    720

tcttcttctt cttctgaaga agaatcttct gaagaacctg aatctcctga agaagaagaa    780

ccttctcaac ctgaacaacc tcaacaatct cctcctcaag aatctcctcc tgaagaatct    840

caagaacctc cttctgaatc ttcttcttct gaacaatctt ctgaatctca atctcaatct    900

ccttcttctt cttctgaacc tcaagaacct caacctcctg aaccttcttc tcaagaagaa    960

cctgaacctc ctgaacaaga acctgaacct tctcaacctt ctgaagaatc ttctccttct   1020

tctgaacctg aagaatctcc tcctgaagaa gaatctgaat cttctgaatc tgaagaatct   1080

gaagaagaag aagaagaaga agaatctcct tctccttctc ctcaagaacc ttcttctcaa   1140

cctccttctg aagaaccttc tgaagaacct tctcctgaag aacaagaatc tgaagaagaa   1200

gaatctcctt cttcttctga acaagaagaa ccttctcaat ctgaacaaca atctcctcct   1260

tcttctcctc ctgaatctga acaatctcaa gaagaagaac ctgaagaaga agaacaacct   1320

cctgaacctt ctcaatctcc tgaagaatct gaatctgaag aacaacaatc ttctgaatct   1380

gaacctcctc aatctcctcc tgaagaacct gaacctgaac aacaacaatc ttcttctgaa   1440

gaatctgaac aagaatctga accttctcaa gaagaatctg aatctgaatc tgaagaatct   1500

gaagaatctt ctccttcttc ttctcctcaa cctgaagaac ctgaatctga agaagaacaa   1560

ccttctcctt ctcctgaatc tcaagaacct gaagaatctg aaccttctga agaaccttct   1620

caatctcctg aagaagaaga agaagaacct gaacctgaac ctcaacaatc tgaagaagaa   1680
```

caacctcaag aatcttctca acaagaagaa gaagaacctc ctgaatctga acaacaacct 1740
tcttctgaac aagaagaatc tgaagaacct caacaagaag aaccttctga atctcaacct 1800
caacctcctg aatcttctcc tccttctcct cctcctcctg aagaaccttc tcaagaagaa 1860
tctgaacaag aacctgaaga agaacaatct cctcctgaac ctgaagaaca agaaccttct 1920
ccttctgaat ctgaagaatc tcctcctgaa tctgaatctt ctgaagaaca acaagaagaa 1980
tctgaacctg aatctgaaga agaacctcct caacaatctg aagaacaaca atctcaacct 2040
gaagaagaag aagaagaaca atctgaagaa ccttcttctt ctcctcctga acctcctcaa 2100
caagaacctt cttctccttc tgaacaacct cctcaacctg aagaacctga acctgaagaa 2160
gaatctgaag aaccttctcc tgaacaacct tctgaatctt ctgaacctcc tgaatctcct 2220
gaagaacctt ctcctcctcc tccttcttct gaagaatctg aatctgaatc tgaacaacct 2280
gaagaacaac ctgaatctga agaacctcct tcttctcctt ctgaatcttc tgaagaacct 2340
gaagaagaac ctgaagaaga acaaccttct gaacctcaac ctccttctga acaaccttct 2400
cctcctgaag aacctcaaga agaatctgaa gaagaacctc cttctgaaga accttctcaa 2460
tctgaatctc ctgaacctga accttctcct tcttctcctc ctcctcaaga acctgaacaa 2520
ccttcttctt ctgaacaatc tcctcctgaa ccttctgaac aatctcctcc ttctcaagaa 2580
gaacctgaag aagaaccttc tcaatctgaa caagaatctg aagaacaacc tcaagaagaa 2640
cctcctcaac cttctcctga accttctcct caagaacctt ctgaacctga acctgaagaa 2700
cctcctgaag aagaacctcc tcaacctcct ccttcttctg aacctgaaga acaagaatct 2760
tcttctcctg aacctcaaca acctcaacct tcttcttctc ctgaagaaga acctcctgaa 2820
gaatctcctg aaccttctcc tcaacctgaa cctgaatctg aacctgaaga agaacaatct 2880
ccttctgaac aagaacctga agaagaagaa tctcaagaac cttcttctcc tcaagaacct 2940
gaagaagaac aatctgaatc tgaatctcct tctcctgaac ctgaacctga acctgaagaa 3000

<210> SEQ ID NO 20
<211> LENGTH: 3000
<212> TYPE: DNA
<213> ORGANISM: Artificial Sequence
<220> FEATURE:
<223> OTHER INFORMATION: Sequence was produced using the reverse translation tool located at: www.vivo.colostate.edu/molkit/rtranslate/index.html.

<400> SEQUENCE: 20
cctcaagaac cttctgaatc tgaatctcct caaccttctg aatctgaaga agaacaacct 60
gaacaagaat ctcctgaaca atcttctgaa gaaccttctc aagaacaaga agaacaagaa 120
gaaccttctg aagaagaaga acctgaagaa tctcctgaac cttctgaaga acaagaacct 180
cctcctcctg aagaacctga agaatctcct cctgaacctg aagaagaaga agaagaagaa 240
tctgaatctc ctgaacctca atctgaatct gaagaagaat ctcctgaaga acctcctcaa 300
tctgaagaac ctcaatctcc tcaacctgaa ccttctcctg aagaagaacc tcctgaacct 360
gaacaacctg aaccttctcc tcaatctgaa gaacctcaag aacctcaaga agaagaagaa 420
cctgaagaac ctgaacctga agaagaagaa cctcctgaag aagaatctga agaatcttct 480
caagaatctc cttctgaaga accttcttct tctcctgaat ctgaagaaga agaagaacct 540
cctcaagaac cttcttctga atctgaacct gaagaagaat ctcctcaaga agaagaagaa 600
tctgaacaat ctcaagaatc tgaagaacaa caagaagaat ctccttctcc tgaatctgaa 660
tcttctcctc ctgaatctca agaatctgaa tctgaagaag aagaacaaga atctgaatct 720

```
tcttctcaac cttctgaacc tgaagaagaa caagaagaag aagaagaatc tcctgaacct    780
gaacaagaac ctgaacctga agaatcttct tcttcttctg aatctcaatc tgaatcttct    840
gaacaagaat cttctcaaga atctgaacaa tctcctcctg aagaagaaga atctgaatct    900
tctcaagaat ctgaatctcc tgaatctgaa caagaacaac ctcctgaaga atctgaagaa    960
gaacaacctc ctgaagaacc tgaagaacaa cctcaagaac ctcaatcttc tcctcaagaa   1020
tctccttctt ctcctgaatc tgaatctcct ccttctgaac ctcctccttc tgaagaagaa   1080
gaacctcctg aacaagaaga acctcctgaa tctgaagaag aacctgaaga agaagaagaa   1140
gaagaagaag aacctgaaga agaagaagaa gaaccttctg aagaatctcc tgaatctgaa   1200
tctgaacctc ctcctccttc ttctgaacct tctgaacctt ctgaacctga atctcctgaa   1260
gaagaatctt ctcctgaaga atctcaatct cctgaagaag aagaagaaga atctgaagaa   1320
gaacctcaac ctgaatcttc tgaacctgaa gaacctgaag aacaagaaca acaagaagaa   1380
caagaagaac ctccttctcc tcaacctcct gaagaacaac ctcaacaaca agaacaagaa   1440
caatctgaac cttctgaaca acaagaacaa ccttcttctt ctcctgaatc tgaagaagaa   1500
tctgaacctg aagaacctga acctgaacaa gaatctcctc ctgaatctga agaagaatct   1560
gaacaacctc ctgaatctcc ttcttctgaa ccttcttctc ctgaagaatc tcaagaatct   1620
tcttctcctg aatctcctga atctccttct cctcctgaat cttctcaacc tgaagaagaa   1680
cctcaacaag aacctgaacc ttcttctcct caacctcaag aacaacctga agaagaagaa   1740
tctcctcctc cttcttctcc tgaacaacct gaagaacctg aagaagaatc ttcttctcaa   1800
tcttctcaag aagaacaacc ttctgaagaa gaatctgaag aagaagaatc tcaagaagaa   1860
ccttctgaat cttctgaaga acctgaagaa gaagaagaag aacctcctga atctcaatct   1920
gaagaacaat ctcaagaaga acaacctgaa tctcctcaag aagaagaaca atctgaatct   1980
cctcctcaac ctcctgaaga acctgaagaa caatcttctc aagaagaatc tgaagaagaa   2040
caaccttctg aacaatcttc tgaagaacct tcttctgaat ctgaagaatc tgaacctcaa   2100
gaatctgaag aagaagaacc tccttctgaa cctgaatctg aacaacaatc tgaagaacct   2160
cctcaatctc aagaagaatc tcctcaacct tctccttctg aacctgaaga agaagaacaa   2220
ccttctgaag aagaaccttc tcaagaacaa gaacctgaag aagaagaaga agaagaatct   2280
tctgaacctc ctgaagaaga agaacctcaa gaagaacctg aagaacctcc tgaagaagaa   2340
gaagaagaag aacaatctga agaagaagaa gaacctgaag aaccttctga acaagaagaa   2400
gaacctcctg aagaacctga agaatctgaa tctgaatctc cttctcctga accttcttct   2460
tctgaacaat cttctccttc tgaacaagaa caatcttctg aagaatctca acctgaacct   2520
gaacctgaag aacaatctga agaatcttct caacctcctg aacctgaacc tcctcctcct   2580
cctgaatctg aatcttcttc ttctgaatct gaatctgaac aatctgaatc tcaagaagaa   2640
cctgaacctt ctgaagaacc ttctgaacaa tcttctgaat ctgaagaacc tgaatctgaa   2700
gaagaagaag aatctcctga agaacctgaa caagaacaac cttctgaacc tgaagaacct   2760
gaacctgaat ctgaacaaga agaagaatct gaatctcctc ctcctcctcc ttctgaagaa   2820
tctcctcctc aatcttctga accttctcct gaagaacaac ctcaagaatc tgaacctgaa   2880
cctgaacctt cttctcctcc tgaacctcct cctgaagaag aatcttctga acctgaatct   2940
gaagaagaat ctgaatcttc tgaacaagaa cctgaagaac ctcctgaatc tgaatctgaa   3000
```

<210> SEQ ID NO 21
<211> LENGTH: 3000

```
<212> TYPE: DNA
<213> ORGANISM: Artificial Sequence
<220> FEATURE:
<223> OTHER INFORMATION: Sequence was produced using the reverse
      translation tool located at:
      www.vivo.colostate.edu/molkit/rtranslate/index.html.

<400> SEQUENCE: 21

gaagaagaag aatcttctcc tcctgaagaa gaagaatctt ctcctgaacc tgaagaacct     60

gaacctgaac cttctcctcc tcaagaagaa gaagaagaac cttctcctca agaacaacaa    120

cctcaacaac aagaatcttc tcaagaagaa gaacaagaac ctgaagaaga agaacaagaa    180

tcttcttctc ctcaagaaga acctcctcaa cctgaagaag aacctgaacc tgaagaagaa    240

gaagaatctt cttctgaaga agaagaacct gaagaacaag aacaacctga acctgaagaa    300

gaaccttctc ctgaatcttc tgaatctgaa tcttcttctt ctgaagaaga agaagaacaa    360

ccttctcaac ctgaatcttc tccttctgaa gaagaacaac ctcaagaacc tgaagaacct    420

gaacctgaag aagaatctcc ttctcctcct gaagaacaag aagaagaatc tgaatctgaa    480

gaagaacaag aacaatctga acctgaagaa tctgaagaag aagaagaacc ttcttctcct    540

caatctgaac aagaagaacc tcaagaacct gaacctgaag aacaagaaga agaacctcct    600

gaagaagaag aacaagaacc tcctgaatct gaatctcctg aagaacaaga agaagaacaa    660

cctccttctc ctgaagaaga atctgaagaa gaagaagaac ctgaagaaga agaagaacaa    720

gaagaatctg aagaagaaga atctcaatct ccttctgaag aacctgaacc tgaagaatct    780

tcttctcctg aatctgaaga acctcctgaa gaagaatctt ctgaagaatc ttctgaagaa    840

tctcaagaag aatctccttc tcctgaagaa gaagaagaat cttctgaatc tgaacaacct    900

cctgaatctc cttctgaatc tcaagaatct ccttctcaat ctgaagaaga atctcaagaa    960

gaacctcctg aagaagaatc ttctcctgaa gaagaacctc ctccttctcc ttctgaatct   1020

gaacctcctg aagaagaaga agaaccttct gaatctgaag aagaagaacc tcctcctgaa   1080

gaagaagaat cttcttctga agaacaagaa tctgaagaac ctgaatctga agaagaatct   1140

cctgaagaac aatctgaaga agaagaagaa tctcaagaat cttctcctga acctcctgaa   1200

gaatctcctt ctgaacaacc tgaaccttct cctcctgaac ctgaatctga atcttctgaa   1260

cctgaagaag aagaagaaga agaagaagaa cctccttctt ctgaagaaga agaatctgaa   1320

gaacctgaac aacctgaaga agaacaagaa gaacctcaag aagaagaaga atctccttct   1380

gaagaatctc ctgaagaacc tgaagaatct gaacctgaag aagaatctga agaagaagaa   1440

cctgaacaac aacctgaaga agaacctcct gaagaagaag aacaagaatc ttctgaacct   1500

tcttctcctc cttctgaaga acaatctgaa gaacctgaag aacaagaaga acctcctgaa   1560

ccttctcaac ctgaacctca acaagaatct gaatcttctt ctccttctga atctcaacct   1620

gaatctcaag aatctgaaga agaagaagaa gaagaagaat ctgaagaaga atctgaacct   1680

tctcaagaac ctgaagaaca acaacctgaa gaagaagaag aagaagaaga agaacctgaa   1740

gaagaagaag aacaatctga acctgaagaa tcttctgaac aacaagaacc tcctcaatct   1800

tctcaacctc aagaagaatc tgaacaagaa caagaagaac ctcaatctcc tgaagaagaa   1860

tctcctcctc ctgaagaaga agaacctcaa gaagaacctc ctgaacctga agaagaagaa   1920

ccttctgaac aacctccttc ttctcctcct gaagaacaat ctgaacaacc tgaacaatct   1980

gaacctcaat ctgaatctcc ttctcaacct gaatcttctg aacaacctga agaacaacct   2040

gaacctcctt ctcctcaatc ttctgaagaa tctgaagaac ctgaagaaga agaacaatct   2100

gaagaacctt ctccttctca atctgaatct tcttcttctc ctgaagaatc tgaacctcct   2160
```

gaagaagaag aagaagaaga agaacctgaa gaacctgaac aagaagaaga acaatctgaa 2220
cctcaagaac aagaaccttc tgaagaatct tctgaacctg aagaagaatc ttctccttct 2280
tctcaatctt ctgaacaatc ttcttctgaa gaagaatctg aatctgaaca atcttctcct 2340
cctcctgaag aagaatctcc tgaagaagaa gaacctgaag aagaagaacc tgaagaatct 2400
cctgaagaag aatctgaaga atctcctgaa tctgaagaat ctgaagaatc ttctgaagaa 2460
caagaagaat cttctcctga agaagaacct tctgaacaag aagaacctcc tgaacaagaa 2520
cctgaatctc ctcctgaaca agaagaagaa gaagaacaat ctgaacctca agaagaagaa 2580
cctcctgaat cttctgaacc tgaagaagaa tctcctcctg aagaacctca atctgaagaa 2640
gaagaagaag aacctcaacc tgaatctgaa tctgaacctg aagaaccttc tcctgaacct 2700
gaatctgaag aatctgaaga agaacctgaa tctgaatctt cttctcctcc tgaatcttct 2760
tctgaagaag aagaagaaga acctgaagaa caatctgaag aagaagaaga atctcaagaa 2820
gaagaagaac aagaagaaga accttctcaa gaagaagaag aacctgaaga acaacaacct 2880
ccttctgaag aagaagaaca acctgaacaa tctgaagaac ctgaaccttc tgaaccttct 2940
gaagaagaac ctgaacctga agaatctcct cctgaatctc aacctccttc tgaagaacct 3000

<210> SEQ ID NO 22
<211> LENGTH: 3000
<212> TYPE: DNA
<213> ORGANISM: Artificial Sequence
<220> FEATURE:
<223> OTHER INFORMATION: Sequence was produced using the reverse translation tool located at: www.vivo.colostate.edu/molkit/rtranslate/index.html.

<400> SEQUENCE: 22
ggtcaacaag gttcttctcc tccttctcct tctcaaggtg gtcaacctcc ttcttctcaa 60
ccttctcaac aatcttcttc ttctcctcct ccttctcctc ctccttcttc tcctccttct 120
caacctcctt ctcctccttc ttctggttct ggttcttctt ctccttctca aggttctcct 180
ccttctcctc cttctcaagg tcctcctcaa cctcctcaat ctcctggttc tcaaggtcct 240
cctcctcctc ctggtcctgg ttctggtcct cctccttctt cttctcctca accttctcaa 300
cctcctcctt ctcaaccttc tcaacaatct cctcaacctt ctcctggtcc tggttctcct 360
tctcaacaac cttcttctgg ttctcaacaa tctcctggtc aaggtcctca acctcaaggt 420
ccttctggtt ctcctcaagg tcaaggttct cctggttctt cttctggtcc tcaaccttct 480
tctcaaggtt ctcctcctgg tcctcctcct ggtccttctc cttctggtgg tcctcaatct 540
tctcctggtt ctcctccttc tcctcaaggt tctcaacctc aatctcctgg tccttcttct 600
ccttcttctt ctcctcaacc tccttctggt cctccttctt ctggtggtca atcttctcaa 660
ggtcaatctc cttctcaagg tcctcctcct ggttctcctc aacctcctgg tggttctggt 720
ccttctcctt cttcttctcc tcctccttct cctcctcctc ctcaatcttc ttcttctggt 780
tctcaacaat cttcttcttc ttctggttct cctccttctt cttctcaagg tcctcctcaa 840
tcttcttctc aacctcaatc tcaatcttct ccttctcaac ctccttctgg ttctcctggt 900
tcttcttctt ctccttctcc ttctccttct ggtccttctg gttctccttc tggtcctcct 960
tcttctcctt ctggttctcc tcctcctggt ggtcctcctc aatctggtgg tcctggtcct 1020
tcttctggtc aacaacctcc tggtcctcaa cctggttctc ctcctggtca acctcaacct 1080
ggttcttctt ctcaaggtcc tcaacaaggt cctcctcctg gttctcctca aggtccttct 1140
caacctggtc ctcaatctcc tccttcttct ggtggttctt cttctcaacc tcaatctcct 1200

```
tcttctggtc ctggtcaacc ttctccttct cctcctggtt ctcctggtgg tcctggtcaa   1260

cctccttctc aaccttctcc ttcttcttct tcttctcaat ctggtcaatc ttctcaacct   1320

tctggtcctc cttctggtca atctcaacct ggtcaacctc ctcaaccttc tcctccttct   1380

cctcctcctc cttctcctcc ttctcaatct ggttctggtt ctcctggtcc tccttctggt   1440

cctcaacctt cttctcaacc ttctccttct caacctggtc aaggtccttc ttcttctcct   1500

cctggtcaat ctggtccttc ttctccttct tcttctcaac ctcctccttc tcaatctcct   1560

cctcaatctg gtcaatctcc ttcttcttct cctcctcaat cttctccttc ttctggtcaa   1620

caaccttctc ctggtcctcc ttcttcttct tctcctcaac cttcttcttc tcaaggttct   1680

cctcctcctc aacctcaagg tcaatctcct ccttctcaac aaccttctca acctggtggt   1740

tcttctcaac cttcttctcc tcctcctcct ggtcctcaag gtcctcaacc tccttctcct   1800

caacctcctt ctggtcctgg ttctcaacct caaggtggtt ctccttcttc tcaaggtggt   1860

caaccttctt cttctcctcc tcaatcttct tctggtcctt ctggtcctgg ttcttctcct   1920

tctcaatctc cttctggtca aggtccttct tctcaacctt ctccttctgg ttctggtcaa   1980

cctcaaggtc ctccttctcc ttctggtcaa cctccttctc ctccttctgg ttctccttct   2040

cctcctcaac ctggttctcc tggtcaacct caaccttctc ctccttctca atctcctggt   2100

ggtcctggtg gtcctcaagg tcctccttct tctcctggtt cttctggttc ttctggttct   2160

tctcaacctc ctcctcctcc ttctcaacaa tcttcttctg gtcaatctcc tcaacctcaa   2220

ggtcaaggtc aacaacctgg ttctcctggt caatctggtc aacaatctca atctcctggt   2280

ggtccttctc ctcaacaacc tcctcctcct cctcctcctc ctcctggttc ttctcctcaa   2340

tcttctcctc aaccttctcc ttctcaatct caacctcaat ctggttctca atcttctcaa   2400

caacaatctc aatcttcttc ttctccttct cctcaatctc aaggtggtcc tcaatcttct   2460

ggttcttctc cttcttctgg tcctcaatct ccttctcctg gtggtcctcc tccttctcaa   2520

tcttcttctg gtcaaccttc tcctccttct cctcctggtc cttctggttc ttcttcttct   2580

tcttctggtt ctggttctgg tcctcaacct tctcctcctc ctcaatctcc ttctcaacaa   2640

tctggttctt ctcaatcttc tccttctcaa tctcaacctc aacctcctcc tcctggttct   2700

ggtcaacctc ctccttctgg tggtcctcaa caacctcctt ctcctcaaca aggttctcaa   2760

tcttcttctc aacctcctcc tcctcaatct tcttcttctg gtggtcctgg tcaatcttct   2820

ggttctcctg gtccttctcc tcctcaacaa tctggtggtt ctcctcctcc ttctggtggt   2880

ggttctggtc ctggttctcc tccttctggt caaggttctc cttctcaatc ttctggtcct   2940

tctggtggtc ctggtggttc tcctcctcct ccttcttctc cttctccttc tcaatcttct   3000
```

<210> SEQ ID NO 23
<211> LENGTH: 100
<212> TYPE: PRT
<213> ORGANISM: Artificial Sequence
<220> FEATURE:
<223> OTHER INFORMATION: The sequence was produced using the random sequence generator tool located at the Swiss-Prot website: http://au.expasy.org/tools/randseq.html.

<400> SEQUENCE: 23

```
Pro Ser Lys Ser Pro Ser Pro Lys Pro Pro Gln Pro Ser Lys Pro Pro
 1               5                  10                  15

Gln Ser Lys Lys Pro Gln Ser Gln Ser Pro Pro Pro Gln Ser Ser Pro
            20                  25                  30

Lys Ser Pro Pro Lys Pro Pro Gln Ser Lys Gln Gln Pro Ser Ser Pro
```

```
        35                  40                  45

Ser Pro Gln Gln Pro Ser Lys Lys Ser Ser Ser Ser Gln Ser Gln Pro
    50                  55                  60

Ser Gln Lys Ser Ser Pro Lys Ser Ser Lys Pro Pro Pro Ser Gln Lys
65                  70                  75                  80

Pro Pro Lys Pro Lys Pro Lys Pro Pro Pro Lys Ser Pro Gln Ser Lys
                85                  90                  95

Pro Gln Gln Lys
            100


<210> SEQ ID NO 24
<211> LENGTH: 30
<212> TYPE: PRT
<213> ORGANISM: Artificial Sequence
<220> FEATURE:
<223> OTHER INFORMATION: The sequence was produced using the random
      sequence generator tool located at the Swiss-Prot
      website: http://au.expasy.org/tools/randseq.html.

<400> SEQUENCE: 24

Lys Ser Pro Pro Lys Pro Pro Gln Ser Lys Gln Gln Pro Ser Ser Pro
 1               5                  10                  15

Ser Pro Gln Gln Pro Ser Lys Lys Ser Ser Ser Ser Gln Ser
            20                  25                  30


<210> SEQ ID NO 25
<211> LENGTH: 100
<212> TYPE: PRT
<213> ORGANISM: Artificial Sequence
<220> FEATURE:
<223> OTHER INFORMATION: The sequence was produced using the random
      sequence generator tool located at the Swiss-Prot
      website: http://au.expasy.org/tools/randseq.html.

<400> SEQUENCE: 25

Pro Ser Glu Ser Pro Ser Pro Glu Pro Pro Gln Pro Ser Glu Pro Pro
 1               5                  10                  15

Gln Ser Glu Glu Pro Gln Ser Gln Ser Pro Pro Pro Gln Ser Ser Pro
            20                  25                  30

Glu Ser Pro Pro Glu Pro Pro Gln Ser Glu Gln Gln Pro Ser Ser Pro
        35                  40                  45

Ser Pro Gln Gln Pro Ser Glu Glu Ser Ser Ser Ser Gln Ser Gln Pro
    50                  55                  60

Ser Gln Glu Ser Ser Pro Glu Ser Ser Glu Pro Pro Pro Ser Gln Glu
65                  70                  75                  80

Pro Pro Glu Pro Glu Pro Glu Pro Pro Pro Glu Ser Pro Gln Ser Glu
                85                  90                  95

Pro Gln Gln Glu
            100


<210> SEQ ID NO 26
<211> LENGTH: 30
<212> TYPE: PRT
<213> ORGANISM: Artificial Sequence
<220> FEATURE:
<223> OTHER INFORMATION: The sequence was produced using the random
      sequence generator tool located at the Swiss-Prot
      website: http://au.expasy.org/tools/randseq.html.

<400> SEQUENCE: 26

Glu Ser Pro Pro Glu Pro Pro Gln Ser Glu Gln Gln Pro Ser Ser Pro
 1               5                  10                  15
```

Ser Pro Gln Gln Pro Ser Glu Glu Ser Ser Ser Ser Gln Ser
20 25 30

<210> SEQ ID NO 27
<211> LENGTH: 100
<212> TYPE: PRT
<213> ORGANISM: Artificial Sequence
<220> FEATURE:
<223> OTHER INFORMATION: The sequence was produced using the random sequence generator tool located at the Swiss-Prot website: http://au.expasy.org/tools/randseq.html.

<400> SEQUENCE: 27

Pro Ser Gly Ser Pro Ser Pro Gly Pro Pro Gln Pro Ser Gly Pro Pro
1 5 10 15

Gln Ser Gly Gly Pro Gln Ser Gln Ser Pro Pro Pro Gln Ser Ser Pro
20 25 30

Gly Ser Pro Pro Gly Pro Pro Gln Ser Gly Gln Gln Pro Ser Ser Pro
35 40 45

Ser Pro Gln Gln Pro Ser Gly Gly Ser Ser Ser Ser Gln Ser Gln Pro
50 55 60

Ser Gln Gly Ser Ser Pro Gly Ser Ser Gly Pro Pro Pro Ser Gln Gly
65 70 75 80

Pro Pro Gly Pro Gly Pro Gly Pro Pro Pro Gly Ser Pro Gln Ser Gly
85 90 95

Pro Gln Gln Gly
100

<210> SEQ ID NO 28
<211> LENGTH: 30
<212> TYPE: PRT
<213> ORGANISM: Artificial Sequence
<220> FEATURE:
<223> OTHER INFORMATION: The sequence was produced using the random sequence generator tool located at the Swiss-Prot website: http://au.expasy.org/tools/randseq.html.

<400> SEQUENCE: 28

Gly Ser Pro Pro Gly Pro Pro Gln Ser Gly Gln Gln Pro Ser Ser Pro
1 5 10 15

Ser Pro Gln Gln Pro Ser Gly Gly Ser Ser Ser Ser Gln Ser
20 25 30

<210> SEQ ID NO 29
<211> LENGTH: 300
<212> TYPE: DNA
<213> ORGANISM: Artificial Sequence
<220> FEATURE:
<223> OTHER INFORMATION: Sequence was produced using the reverse translation tool located at: www.vivo.colostate.edu/molkit/rtranslate/index.html

<400> SEQUENCE: 29
ccttctaaat ctccttctcc taaacctcct caaccttcta aacctcctca atctaaaaaa 60
cctcaatctc aatctcctcc tcctcaatct tctcctaaat ctcctcctaa acctcctcaa 120
tctaaacaac aaccttcttc tccttctcct caacaacctt ctaaaaaatc ttcttcttct 180
caatctcaac cttctcaaaa atcttctcct aaatcttcta aacctcctcc ttctcaaaaa 240
cctcctaaac ctaaacctaa acctcctcct aaatctcctc aatctaaacc tcaacaaaaa 300

<210> SEQ ID NO 30
<211> LENGTH: 90
<212> TYPE: DNA

<213> ORGANISM: Artificial Sequence
<220> FEATURE:
<223> OTHER INFORMATION: Sequence was produced using the reverse translation tool located at: www.vivo.colostate.edu/molkit/rtranslate/index.html

<400> SEQUENCE: 30

```
aaatctcctc ctaaacctcc tcaatctaaa caacaacctt cttctccttc tcctcaacaa     60

ccttctaaaa aatcttcttc ttctcaatct                                      90
```

<210> SEQ ID NO 31
<211> LENGTH: 300
<212> TYPE: DNA
<213> ORGANISM: Artificial Sequence
<220> FEATURE:
<223> OTHER INFORMATION: Sequence was produced using the reverse translation tool located at: www.vivo.colostate.edu/molkit/rtranslate/index.html

<400> SEQUENCE: 31

```
ccttctgaat ctccttctcc tgaacctcct caaccttctg aacctcctca atctgaagaa     60

cctcaatctc aatctcctcc tcctcaatct tctcctgaat ctcctcctga acctcctcaa    120

tctgaacaac aaccttcttc tccttctcct caacaacctt ctgaagaatc ttcttcttct    180

caatctcaac cttctcaaga atcttctcct gaatcttctg aacctcctcc ttctcaagaa    240

cctcctgaac ctgaacctga acctcctcct gaatctcctc aatctgaacc tcaacaagaa    300
```

<210> SEQ ID NO 32
<211> LENGTH: 90
<212> TYPE: DNA
<213> ORGANISM: Artificial Sequence
<220> FEATURE:
<223> OTHER INFORMATION: Sequence was produced using the reverse translation tool located at: www.vivo.colostate.edu/molkit/rtranslate/index.html

<400> SEQUENCE: 32

```
gaatctcctc ctgaacctcc tcaatctgaa caacaacctt cttctccttc tcctcaacaa     60

ccttctgaag aatcttcttc ttctcaatct                                      90
```

<210> SEQ ID NO 33
<211> LENGTH: 300
<212> TYPE: PRT
<213> ORGANISM: Artificial Sequence
<220> FEATURE:
<223> OTHER INFORMATION: Sequence was produced using the reverse translation tool located at: www.vivo.colostate.edu/molkit/rtranslate/index.html

<400> SEQUENCE: 33

```
Cys Cys Thr Thr Cys Thr Gly Gly Thr Thr Cys Thr Cys Cys Thr Thr
 1               5                  10                  15

Cys Thr Cys Cys Thr Gly Gly Thr Cys Cys Thr Cys Cys Thr Cys Ala
            20                  25                  30

Ala Cys Cys Thr Thr Cys Thr Gly Gly Thr Cys Cys Thr Cys Cys Thr
        35                  40                  45

Cys Ala Ala Thr Cys Thr Gly Gly Thr Gly Gly Thr Cys Cys Thr Cys
    50                  55                  60

Ala Ala Thr Cys Thr Cys Ala Ala Thr Cys Thr Cys Cys Thr Cys Cys
65                  70                  75                  80

Thr Cys Cys Thr Cys Ala Ala Thr Cys Thr Thr Cys Thr Cys Cys Thr
                85                  90                  95
```

-continued

```
Gly Gly Thr Thr Cys Thr Cys Cys Thr Cys Cys Thr Gly Gly Thr Cys
            100                 105                 110

Cys Thr Cys Cys Thr Cys Ala Ala Thr Cys Thr Gly Gly Thr Cys Ala
        115                 120                 125

Ala Cys Ala Ala Cys Cys Thr Thr Cys Thr Thr Cys Thr Cys Cys Thr
    130                 135                 140

Thr Cys Thr Cys Cys Thr Cys Ala Ala Cys Ala Ala Cys Cys Thr Thr
145                 150                 155                 160

Cys Thr Gly Gly Thr Gly Gly Thr Thr Cys Thr Thr Cys Thr Thr Cys
                165                 170                 175

Thr Thr Cys Thr Cys Ala Ala Thr Cys Thr Cys Ala Ala Cys Cys Thr
            180                 185                 190

Thr Cys Thr Cys Ala Ala Gly Gly Thr Thr Cys Thr Thr Cys Thr Cys
        195                 200                 205

Cys Thr Gly Gly Thr Thr Cys Thr Thr Cys Thr Gly Gly Thr Cys Cys
    210                 215                 220

Thr Cys Cys Thr Cys Cys Thr Thr Cys Thr Cys Ala Ala Gly Gly Thr
225                 230                 235                 240

Cys Cys Thr Cys Cys Thr Gly Gly Thr Cys Cys Thr Gly Gly Thr Cys
                245                 250                 255

Cys Thr Gly Gly Thr Cys Cys Thr Cys Cys Thr Cys Cys Thr Gly Gly
            260                 265                 270

Thr Thr Cys Thr Cys Cys Thr Cys Ala Ala Thr Cys Thr Gly Gly Thr
        275                 280                 285

Cys Cys Thr Cys Ala Ala Cys Ala Ala Gly Gly Thr
    290                 295                 300
```

<210> SEQ ID NO 34
<211> LENGTH: 90
<212> TYPE: DNA
<213> ORGANISM: Artificial Sequence
<220> FEATURE:
<223> OTHER INFORMATION: Sequence was produced using the reverse translation tool located at: www.vivo.colostate.edu/molkit/rtranslate/index.html

<400> SEQUENCE: 34

```
ggttctcctc ctggtcctcc tcaatctggt caacaacctt cttctccttc tcctcaacaa     60

ccttctggtg gttcttcttc ttctcaatct                                      90
```

<210> SEQ ID NO 35
<211> LENGTH: 100
<212> TYPE: PRT
<213> ORGANISM: Artificial Sequence
<220> FEATURE:
<223> OTHER INFORMATION: The sequence was produced using the random sequence generator tool located at the Swiss-Prot website: http://au.expasy.org/tools/randseq.html.
<220> FEATURE:
<221> NAME/KEY: VARIANT
<222> LOCATION: 3, 8, 14, 19, 20, 33, 37, 42, 55, 56, 67, 71, 74, 80, 83, 85, 87, 91, 96, 100
<223> OTHER INFORMATION: Xaa = Lys, Glu or Gly

<400> SEQUENCE: 35

```
Pro Ser Xaa Ser Pro Ser Pro Xaa Pro Pro Gln Pro Ser Xaa Pro Pro
 1               5                  10                  15

Gln Ser Xaa Xaa Pro Gln Ser Gln Ser Pro Pro Pro Gln Ser Ser Pro
            20                  25                  30

Xaa Ser Pro Pro Xaa Pro Pro Gln Ser Xaa Gln Gln Pro Ser Ser Pro
        35                  40                  45
```

```
Ser Pro Gln Gln Pro Ser Xaa Xaa Ser Ser Ser Ser Gln Ser Gln Pro
    50                  55                  60

Ser Gln Xaa Ser Ser Pro Xaa Ser Ser Xaa Pro Pro Pro Ser Gln Xaa
65                  70                  75                  80

Pro Pro Xaa Pro Xaa Pro Xaa Pro Pro Pro Xaa Ser Pro Gln Ser Xaa
                85                  90                  95

Pro Gln Gln Xaa
            100


<210> SEQ ID NO 36
<211> LENGTH: 4237
<212> TYPE: DNA
<213> ORGANISM: Artificial Sequence
<220> FEATURE:
<223> OTHER INFORMATION: pAquoProt expression vector backbone

<400> SEQUENCE: 36

tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accatatgtt cagatctcct ttcagcaaaa aacccctcaa gacccgttta gaggccccaa     240

ggggttatgc tagttattgc tcagcggtgg cagcagccta ggttaattaa gctacgctag     300

tttaagcgta atctggaaca tcgtatgggt aaccctcgag tgcggccgca agcttggtac     360

cgatatcctc ccaattggga tccggactct tgtcgtcgtc atcattcgaa ccggcaccgt     420

ggtgatggtg atggtgtgcc atggtatatc tccttcttaa agttaaacaa aattatttct     480

agaggggaat tgttatccgc tcacaattcc cctatagtga gtcgtattaa ttcgcggtcg     540

accagctgca ttaatgaatc ggccaacgcg cggggagagg cggtttgcgt attgggcgct     600

cttccgctga caccatcgaa tggcgcaaaa cctttcgcgg tatggcatga tagcgcccgg     660

aagagagtca attcagggtg gtgaatgtga aaccagtaac gttatacgat gtcgcagagt     720

atgccggtgt ctcttatcag accgtttccc gcgtggtgaa ccaggccagc cacgtttctg     780

cgaaaacgcg ggaaaaagtg gaagcggcga tggcggagct gaattacatt cccaaccgcg     840

tggcacaaca actggcgggc aaacagtcgt tgctgattgg cgttgccacc tccagtctgg     900

ccctgcacgc gccgtcgcaa attgtcgcgg cgattaaatc tcgcgccgat caactgggtg     960

ccagcgtggt ggtgtcgatg gtagaacgaa gcggcgtcga agcctgtaaa gcggcggtgc    1020

acaatcttct cgcgcaacgc gtcagtgggc tgatcattaa ctatccgctg gatgaccagg    1080

atgccattgc tgtggaagct gcctgcacta atgttccggc gttatttctt gatgtctctg    1140

accagacacc catcaacagt attattttct cccatgaaga cggtacgcga ctgggcgtgg    1200

agcatctggt cgcattgggt caccagcaaa tcgcgctgtt agcgggccca ttaagttctg    1260

tctcggcgcg tctgcgtctg gctggctggc ataaatatct cactcgcaat caaattcagc    1320

cgatagcgga acgggaaggc gactggagtg ccatgtccgg ttttcaacaa accatgcaaa    1380

tgctgaatga gggcatcgtt cccactgcga tgctggttgc caacgatcag atggcgctgg    1440

gcgcaatgcg cgccattacc gagtccgggc tgcgcgttgg tgcggacatc tcggtagtgg    1500

gatacgacga taccgaagac agctcatgtt atatcccgcc gttaaccacc atcaaacagg    1560

attttcgcct gctggggcaa accagcgtgg accgcttgct gcaactctct cagggccagg    1620

cggtgaaggg caatcagctg ttgcccgtct cactggtgaa aagaaaaacc accctggcgc    1680

ccaatacgca aaccgcctct ccccgcgcgt tggccgattc attaatgcag ctggcacgac    1740
```

-continued

```
aggtttcccg actggaaagc gggcagtgag ctcttccgct atcctcgctc actgactcgc   1800
tgcgctcggt cgttcggctg cggcgagcgg tatcagctca ctcaaaggcg gtaatacggt   1860
tatccacaga atcaggggat aacgcaggaa agaacatgtg agcaaaaggc cagcaaaagg   1920
ccaggaaccg taaaaaggcc gcgttgctgg cgtttttcca taggctccgc ccccctgacg   1980
agcatcacaa aaatcgacgc tcaagtcaga ggtggcgaaa cccgacagga ctataaagat   2040
accaggcgtt tccccctgga agctccctcg tgcgctctcc tgttccgacc ctgccgctta   2100
ccggatacct gtccgccttt ctcccttcgg gaagcgtggc gctttctcat agctcacgct   2160
gtaggtatct cagttcggtg taggtcgttc gctccaagct gggctgtgtg cacgaacccc   2220
ccgttcagcc cgaccgctgc gccttatccg gtaactatcg tcttgagtcc aacccggtaa   2280
gacacgactt atcgccactg gcagcagcca ctggtaacag gattagcaga gcgaggtatg   2340
taggcggtgc tacagagttc ttgaagtggt ggcctaacta cggctacact agaaggacag   2400
tatttggtat ctgcgctctg ctgaagccag ttaccttcgg aaaaagagtt ggtagctctt   2460
gatccggcaa acaaaccacc gctggtagcg gtggtttttt tgtttgcaag cagcagatta   2520
cgcgcagaaa aaaaggatct caagaagatc ctttgatctt ttctacgggg tctgacgctc   2580
agtggaacga aaactcacgt taagggattt tggtcatgag attatcaaaa aggatcttca   2640
cctagatcct tttaaattaa aaatgaagtt ttaaatcaat ctaaagtata tatgagtaaa   2700
cttggtctga cagttaccaa tgcttaatca gtgaggcacc tatctcagcg atctgtctat   2760
ttcgttcatc catagttgcc tgactccccg tcgtgtagat aactacgata cgggagggct   2820
taccatctgg ccccagtgct gcaatgatac cgcgagaccc acgctcaccg gctccagatt   2880
tatcagcaat aaaccagcca gccggaaggg ccgagcgcag aagtggtcct gcaactttat   2940
ccgcctccat ccagtctatt aattgttgcc gggaagctag agtaagtagt tcgccagtta   3000
atagtttgcg caacgttgtt gccattgcta caggcatcgt ggtgtcacgc tcgtcgtttg   3060
gtatggcttc attcagctcc ggttcccaac gatcaaggcg agttacatga tcccccatgt   3120
tgtgcaaaaa agcggttagc tccttcggtc ctccgatcgt tgtcagaagt aagttggccg   3180
cagtgttatc actcatggtt atggcagcac tgcataattc tcttactgtc atgccatccg   3240
taagatgctt ttctgtgact ggtgagtact caaccaagtc attctgagaa tagtgtatgc   3300
ggcgaccgag ttgctcttgc ccggcgtcaa tacgggataa taccgcgcca catagcagaa   3360
ctttaaaagt gctcatcatt ggaaaacgtt cttcggggcg aaaactctca aggatcttac   3420
cgctgttgag atccagttcg atgtaaccca ctcgtgcacc caactgatct tcagcatctt   3480
ttactttcac cagcgtttct gggtgagcaa aaacaggaag gcaaaatgcc gcaaaaaagg   3540
gaataagggc gacacggaaa tgttgaatac tcatactctt cctttttcaa tattattgaa   3600
gcatttatca gggttattgt ctcatgagcg gatacatatt tgaatgtatt tagaaaaata   3660
aacaaatagg ggttccgcgc acatttcccc gaaaagtgcc acctgacgtc taagaaacca   3720
ttattatcat gacattaacc tataaaaata ggcgtatcac gaggccctaa attgtaaacg   3780
ttaatatttt gttaaaattc gcgttaaatt tttgttaaat cagctcattt tttaaccaat   3840
aggccgaaat cggcaaaatc ccttataaat caaaagaata gaccgagata gggttgagtg   3900
ttgttccagt ttggaacaag agtccactat taaagaacgt ggactccaac gtcaaagggc   3960
gaaaaaccgt ctatcagggc gatggcccac tacgtgaacc atcaccctaa tcaagttttt   4020
tggggtcgag gtgccgtaaa gcactaaatc ggaaccctaa agggagcccc cgatttagag   4080
cttgacgggg aaagccggcg aacgtggcga gaaaggaagg gaagaaagcg aaaggagcgg   4140
```

gcgctagggc gctggcaagt gtagcggtca cgctgcgcgt aaccaccaca cccgccgcgc 4200
ttaatgcgcc gctacagggc gcgtaggccc tttcgtc 4237

<210> SEQ ID NO 37
<211> LENGTH: 4240
<212> TYPE: DNA
<213> ORGANISM: Artificial Sequence
<220> FEATURE:
<223> OTHER INFORMATION: pAquoKin expression vector backbone

<400> SEQUENCE: 37
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgtt cagatctcct ttcagcaaaa aacccctcaa gacccgttta gaggccccaa 240
ggggttatgc tagttattgc tcagcggtgg cagcagccta ggttaattaa gctacgctag 300
tttaagcgct cttatcgtcg tcatccttgt aatcaccctc gagtgcggcc gcaagcttgg 360
taccgatatc ctcccaattg ggatccggac tcttgtcgtc gtcatcattc gaaccggcac 420
cgtggtgatg gtgatggtgt gccatggtat atctccttct taaagttaaa caaaattatt 480
tctagagggg aattgttatc cgctcacaat tcccctatag tgagtcgtat taattcgcgg 540
tcgaccagct gcattaatga atcggccaac gcgcggggag aggcggtttg cgtattgggc 600
gctcttccgc tgacaccatc gaatggcgca aaacctttcg cggtatggca tgatagcgcc 660
cggaagagag tcaattcagg gtggtgaatg tgaaaccagt aacgttatac gatgtcgcag 720
agtatgccgg tgtctcttat cagaccgttt cccgcgtggt gaaccaggcc agccacgttt 780
ctgcgaaaac gcgggaaaaa gtggaagcgg cgatggcgga gctgaattac attcccaacc 840
gcgtggcaca acaactggcg ggcaaacagt cgttgctgat tggcgttgcc acctccagtc 900
tggccctgca cgcgccgtcg caaattgtcg cggcgattaa atctcgcgcc gatcaactgg 960
gtgccagcgt ggtggtgtcg atggtagaac gaagcggcgt cgaagcctgt aaagcggcgg 1020
tgcacaatct tctcgcgcaa cgcgtcagtg ggctgatcat taactatccg ctggatgacc 1080
aggatgccat tgctgtggaa gctgcctgca ctaatgttcc ggcgttattt cttgatgtct 1140
ctgaccagac acccatcaac agtattattt tctcccatga agacggtacg cgactgggcg 1200
tggagcatct ggtcgcattg ggtcaccagc aaatcgcgct gttagcgggc ccattaagtt 1260
ctgtctcggc gcgtctgcgt ctggctggct ggcataaata tctcactcgc aatcaaattc 1320
agccgatagc ggaacgggaa ggcgactgga gtgccatgtc cggttttcaa caaaccatgc 1380
aaatgctgaa tgagggcatc gttcccactg cgatgctggt tgccaacgat cagatggcgc 1440
tgggcgcaat gcgcgccatt accgagtccg ggctgcgcgt tggtgcggac atctcggtag 1500
tgggatacga cgataccgaa gacagctcat gttatatccc gccgttaacc accatcaaac 1560
aggattttcg cctgctgggg caaaccagcg tggaccgctt gctgcaactc tctcagggcc 1620
aggcggtgaa gggcaatcag ctgttgcccg tctcactggt gaaaagaaaa accaccctgg 1680
cgcccaatac gcaaaccgcc tctccccgcg cgttggccga ttcattaatg cagctggcac 1740
gacaggtttc ccgactggaa agcgggcagt gagctcttcc gctatcctcg ctcactgact 1800
cgctgcgctc ggtcgttcgg ctgcggcgag cggtatcagc tcactcaaag gcggtaatac 1860
ggttatccac agaatcaggg gataacgcag gaaagaacat gtgagcaaaa ggccagcaaa 1920
aggccaggaa ccgtaaaaag gccgcgttgc tggcgttttt ccataggctc cgcccccctg 1980

```
acgagcatca caaaaatcga cgctcaagtc agaggtggcg aaacccgaca ggactataaa   2040
gataccaggc gtttccccct ggaagctccc tcgtgcgctc tcctgttccg accctgccgc   2100
ttaccggata cctgtccgcc tttctccctt cgggaagcgt ggcgctttct catagctcac   2160
gctgtaggta tctcagttcg gtgtaggtcg ttcgctccaa gctgggctgt gtgcacgaac   2220
cccccgttca gcccgaccgc tgcgccttat ccggtaacta tcgtcttgag tccaacccgg   2280
taagacacga cttatcgcca ctggcagcag ccactggtaa caggattagc agagcgaggt   2340
atgtaggcgg tgctacagag ttcttgaagt ggtggcctaa ctacggctac actagaagga   2400
cagtatttgg tatctgcgct ctgctgaagc cagttacctt cggaaaaaga gttggtagct   2460
cttgatccgg caaacaaacc accgctggta gcggtggttt ttttgtttgc aagcagcaga   2520
ttacgcgcag aaaaaaagga tctcaagaag atcctttgat cttttctacg gggtctgacg   2580
ctcagtggaa cgaaaactca cgttaaggga ttttggtcat gagattatca aaaaggatct   2640
tcacctagat ccttttaaat taaaaatgaa gttttaaatc aatctaaagt atatatgagt   2700
aaacttggtc tgacagttac caatgcttaa tcagtgaggc acctatctca gcgatctgtc   2760
tatttcgttc atccatagtt gcctgactcc ccgtcgtgta gataactacg atacgggagg   2820
gcttaccatc tggccccagt gctgcaatga taccgcgaga cccacgctca ccggctccag   2880
atttatcagc aataaaccag ccagccggaa gggccgagcg cagaagtggt cctgcaactt   2940
tatccgcctc catccagtct attaattgtt gccgggaagc tagagtaagt agttcgccag   3000
ttaatagttt gcgcaacgtt gttgccattg ctacaggcat cgtggtgtca cgctcgtcgt   3060
ttggtatggc ttcattcagc tccggttccc aacgatcaag gcgagttaca tgatccccca   3120
tgttgtgcaa aaaagcggtt agctccttcg gtcctccgat cgttgtcaga agtaagttgg   3180
ccgcagtgtt atcactcatg gttatggcag cactgcataa ttctcttact gtcatgccat   3240
ccgtaagatg cttttctgtg actggtgagt actcaaccaa gtcattctga gaatagtgta   3300
tgcggcgacc gagttgctct tgcccggcgt caatacggga taataccgcg ccacatagca   3360
gaactttaaa agtgctcatc attggaaaac gttcttcggg gcgaaaactc tcaaggatct   3420
taccgctgtt gagatccagt tcgatgtaac ccactcgtgc acccaactga tcttcagcat   3480
cttttacttt caccagcgtt tctgggtgag caaaaacagg aaggcaaaat gccgcaaaaa   3540
agggaataag ggcgacacgg aaatgttgaa tactcatact cttccttttt caatattatt   3600
gaagcattta tcagggttat tgtctcatga gcggatacat atttgaatgt atttagaaaa   3660
ataaacaaat aggggttccg cgcacatttc cccgaaaagt gccacctgac gtctaagaaa   3720
ccattattat catgacatta acctataaaa ataggcgtat cacgaggccc taaattgtaa   3780
acgttaatat tttgttaaaa ttcgcgttaa atttttgtta aatcagctca ttttttaacc   3840
aataggccga aatcggcaaa atcccttata aatcaaaaga atagaccgag atagggttga   3900
gtgttgttcc agtttggaac aagagtccac tattaaagaa cgtggactcc aacgtcaaag   3960
ggcgaaaaac cgtctatcag ggcgatggcc cactacgtga accatcaccc taatcaagtt   4020
ttttggggtc gaggtgccgt aaagcactaa atcggaaccc taaagggagc cccccgattta  4080
gagcttgacg gggaaagccg gcgaacgtgg cgagaaagga agggaagaaa gcgaaaggag   4140
cgggcgctag ggcgctggca agtgtagcgg tcacgctgcg cgtaaccacc acacccgccg   4200
cgcttaatgc gccgctacag ggcgcgtagg ccctttcgtc                          4240
```

<210> SEQ ID NO 38
<211> LENGTH: 120

```
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 38

Glu Pro Pro Ser Glu Pro Glu Ser Glu Glu Ser Glu Pro Glu Glu Pro
 1               5                  10                  15

Gln Ser Ser Gln Pro Pro Pro Pro Ser Glu Pro Gln Gln Pro Ser Gln
            20                  25                  30

Gln Pro Gln Gln Pro Ser Pro Glu Gln Pro Ser Gln Pro Glu Gln Pro
        35                  40                  45

Glu Pro Gln Ser Glu Pro Gln Gln Pro Glu Gln Pro Gln Pro Pro Gln
    50                  55                  60

Pro Pro Pro Pro Glu Gln Ser Pro Ser Pro Pro Glu Ser Gln Ser Gln
65                  70                  75                  80

Ser Ser Ser Pro Ser Pro Gln Gln Pro Ser Pro Glu Pro Ser Ser Ser
                85                  90                  95

Ser Gln Pro Glu Gln Pro Glu Pro Pro Gln Glu Pro Glu Ser Pro Glu
            100                 105                 110

Pro Pro Pro Gln Pro Gln Glu Gln
        115                 120


<210> SEQ ID NO 39
<211> LENGTH: 120
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 39

Pro Glu Pro Glu Pro Gln Pro Pro Ser Pro Gln Ser Pro Ser Pro Pro
 1               5                  10                  15

Pro Pro Pro Pro Pro Pro Ser Gln Pro Pro Gln Pro Ser Pro Pro Pro
            20                  25                  30

Ser Glu Pro Glu Pro Pro Pro Pro Glu Ser Pro Gln Pro Pro Pro Gln
        35                  40                  45

Gln Pro Pro Pro Ser Pro Gln Ser Pro Ser Pro Pro Gln Pro Pro Pro
    50                  55                  60

Ser Pro Pro Pro Pro Pro Gln Pro Gln Pro Pro Gln Ser Glu Pro Gln
65                  70                  75                  80

Pro Pro Gln Pro Glu Pro Pro Pro Ser Ser Pro Pro Pro Gln Glu Ser
                85                  90                  95

Gln Glu Gln Pro Ser Glu Pro Pro Pro Pro Pro Ser Glu Pro Ser Ser
            100                 105                 110

Glu Glu Pro Pro Ser Pro Pro Pro
        115                 120


<210> SEQ ID NO 40
<211> LENGTH: 120
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 40

Pro Gln Glu Glu Pro Glu Gln Ser Pro Gln Pro Glu Glu Pro Pro Pro
 1               5                  10                  15
```

Pro Gln Gln Gln Ser Glu Pro Glu Ser Glu Glu Glu Ser Glu Gln Pro
20 25 30

Glu Pro Ser Pro Pro Pro Pro Pro Gln Glu Ser Glu Ser Gln Gln Glu
35 40 45

Ser Glu Pro Gln Pro Pro Pro Ser Pro Ser Glu Pro Pro Glu Ser Ser
50 55 60

Pro Glu Glu Pro Pro Glu Glu Pro Ser Gln Gln Glu Glu Glu Pro Glu
65 70 75 80

Ser Glu Pro Ser Glu Ser Glu Ser Pro Pro Glu Gln Glu Pro Ser Ser
85 90 95

Glu Pro Glu Gln Pro Gln Pro Glu Gln Pro Pro Ser Glu Glu Glu Gln
100 105 110

Pro Gln Glu Glu Pro Glu Gln Glu
115 120

<210> SEQ ID NO 41
<211> LENGTH: 120
<212> TYPE: PRT
<213> ORGANISM: Artificial Sequence
<220> FEATURE:
<223> OTHER INFORMATION: Randomly generated sequence, created by ExPASy WWW server tool

<400> SEQUENCE: 41

Pro Pro Gln Pro Pro Glu Pro Pro Glu Gly Gln Pro Pro Pro Gly Gly
1 5 10 15

Gly Pro Glu Pro Glu Gly Pro Pro Pro Pro Pro Pro Pro Pro Pro Pro
20 25 30

Pro Gln Gln Pro Gln Glu Gln Pro Pro Gly Pro Pro Gln Pro Glu Pro
35 40 45

Gln Pro Pro Glu Pro Pro Glu Pro Gly Pro Pro Pro Pro Gly Pro Pro
50 55 60

Gln Pro Gln Pro Pro Gly Pro Gly Pro Glu Gly Pro Gly Pro Gln Pro
65 70 75 80

Gln Pro Pro Pro Pro Pro Glu Pro Pro Glu Gly Gly Pro Pro Pro Gln
85 90 95

Gln Pro Gln Pro Pro Glu Gln Glu Pro Gln Pro Glu Pro Glu Glu Gly
100 105 110

Pro Pro Gly Pro Gly Glu Pro Pro
115 120

<210> SEQ ID NO 42
<211> LENGTH: 120
<212> TYPE: PRT
<213> ORGANISM: Artificial Sequence
<220> FEATURE:
<223> OTHER INFORMATION: Randomly generated sequence, created by ExPASy WWW server tool

<400> SEQUENCE: 42

Glu Pro Gly Gln Pro Pro Pro Gly Gly Pro Glu Glu Gln Glu Pro Pro
1 5 10 15

Glu Glu Glu Glu Glu Pro Pro Gln Glu Gln Pro Gln Glu Glu Glu Gly
20 25 30

Glu Pro Gln Gly Glu Glu Pro Gly Gly Gly Glu Gln Gly Pro Glu Pro
35 40 45

Gly Gln Pro Pro Pro Gln Pro Pro Gln Gly Pro Pro Pro Gln Gly Gln
50 55 60

```
Gly Glu Gln Glu Pro Gln Pro Glu Gln Glu Glu Gly Gln Pro Glu Gly
65                  70                  75                  80

Pro Glu Glu Pro Pro Gly Pro Gln Glu Glu Glu Glu Pro Glu Glu Pro
                85                  90                  95

Pro Glu Pro Pro Pro Gln Gly Gly Glu Glu Pro Gly Gln Pro Pro Pro
            100                 105                 110

Pro Glu Glu Glu Gly Glu Gln Glu
        115                 120


<210> SEQ ID NO 43
<211> LENGTH: 120
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 43

Glu Pro Glu Pro Gly Glu Gly Glu Glu Pro Gln Glu Glu Gln Gly Pro
 1               5                  10                  15

Glu Glu Pro Gly Gln Glu Glu Gly Glu Glu Gln Glu Glu Glu Gly Glu
            20                  25                  30

Pro Pro Gln Gly Pro Gln Gln Gln Glu Glu Pro Glu Gly Pro Pro Glu
        35                  40                  45

Glu Gln Gln Glu Pro Pro Pro Glu Gln Pro Glu Pro Glu Glu Pro Pro
    50                  55                  60

Glu Gly Pro Pro Pro Glu Glu Glu Gly Glu Glu Gly Glu Glu Gln Pro
65                  70                  75                  80

Gln Gly Pro Glu Glu Gly Gln Gln Glu Pro Gln Pro Glu Gly Gly Pro
                85                  90                  95

Gly Pro Pro Glu Glu Pro Pro Glu Glu Pro Pro Gln Glu Gly Glu Pro
            100                 105                 110

Pro Glu Glu Glu Glu Glu Pro Glu
        115                 120


<210> SEQ ID NO 44
<211> LENGTH: 250
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 44

Glu Glu Gln Pro Glu Pro Pro Gln Ser Glu Gln Glu Asp Pro Glu Glu
 1               5                  10                  15

Pro Gly Ser Ser Gln Gly Glu Pro Gly Pro Pro Glu Gln Ser Pro Gly
            20                  25                  30

Gly Pro Pro Glu Glu Pro Asp Gln Pro Ser Glu Glu Pro Pro Pro Glu
        35                  40                  45

Glu Pro Gln Pro Gln Ser Glu Gly Ser Pro Gly Pro Pro Pro Glu Gly
    50                  55                  60

Pro Pro Glu Pro Asp Pro Glu Glu Asp Glu Ser Glu Glu Pro Gln Gln
65                  70                  75                  80

Pro Pro Ser Gln Pro Ser Pro Pro Ser Glu Gly Gln Pro Pro Glu Pro
                85                  90                  95

Pro Gln Glu Gln Ser Ser Ser Ser Glu Glu Ser Gly Pro Ser Glu Pro
            100                 105                 110

Ser Ser Asp Pro Ser Ser Glu Glu Ser Asp Pro Pro Glu Pro Ser Pro
```

```
        115                 120                 125

Ser Pro Pro Pro Ser Glu Gly Ser Ser Glu Pro Pro Gln Gln Pro Asp
    130                 135                 140

Asp Pro Ser Pro Pro Gly Glu Pro Gln Pro Glu Glu Gln Pro Glu Pro
145                 150                 155                 160

Gly Ser Pro Asp Asp Gln Ser Pro Pro Pro Ser Pro Ser Pro Pro Gly
                165                 170                 175

Glu Pro Gln Gly Gln Pro Asp Gly Ser Pro Ser Gly Glu Pro Gly Gln
            180                 185                 190

Ser Glu Glu Pro Gln Pro Gly Gly Asp Pro Glu Pro Ser Pro Pro Gly
        195                 200                 205

Gln Glu Glu Pro Pro Glu Pro Ser Pro Glu Gly Ser Pro Ser Glu Gly
    210                 215                 220

Ser Pro Gly Glu Pro Pro Ser Pro Pro Gly Ser Asp Pro Glu Ser Asp
225                 230                 235                 240

Gly Gly Pro Gln Pro Pro Gln Asp Gln Gln
                245                 250


<210> SEQ ID NO 45
<211> LENGTH: 250
<212> TYPE: PRT
<213> ORGANISM: Artificial Sequence
<220> FEATURE:
<223> OTHER INFORMATION: Randomly generated sequence, created by ExPASy
      WWW server tool

<400> SEQUENCE: 45

Glu Glu Gln Pro Glu Pro Ile Val Ser Glu Gln Glu Asp Pro Glu Glu
 1               5                  10                  15

Pro Gly Ser Ser Val Phe Glu Ile Leu Pro Pro Glu Gln Ser Pro Gly
            20                  25                  30

Gly Pro Pro Glu Glu Pro Asp Gln Pro Ser Glu Glu Pro Val Met Glu
        35                  40                  45

Glu Ile Gln Pro Gln Leu Glu Gly Ser Pro Gly Pro Pro Pro Glu Gly
    50                  55                  60

Pro Pro Glu Pro Asp Pro Glu Glu Asp Glu Ser Glu Glu Ile Gln Gln
65                  70                  75                  80

Pro Ile Ser Gln Pro Ser Pro Pro Ser Glu Gly  Gln Leu Leu Glu Pro
               85                  90                   95

Leu Gln Glu Gln Ser Ser Ser Ser Glu Glu Ser Gly Pro Ser Glu Pro
            100                 105                 110

Ser Ser Asp Pro Ser Ser Glu Glu Ser Asp Pro Pro Glu Pro Leu Ile
        115                 120                 125

Ser Val Phe Pro Ser Glu Gly Ser Ser Glu Pro Pro Gln Gln Pro Asp
    130                 135                 140

Asp Leu Ser Pro Pro Leu Glu Pro Gln Pro Glu Glu Gln Pro Glu Pro
145                 150                  155                160

Gly Ser Pro Asp Asp Gln Ser Pro Pro Pro Ser Pro Ser Pro Pro Gly
                165                 170                 175

Glu Pro Gln Gly Gln Pro Asp Gly Ser Pro Ser Gly Glu Pro Gly Gln
            180                 185                 190

Ser Glu Glu Pro Gln Pro Gly Gly Asp Pro Glu Ile Val Pro Pro Ile
        195                 200                 205

Gln Glu Glu Leu Pro Glu Pro Ser Pro Glu Gly Ser Pro Leu Glu Gly
    210                 215                 220

Ser Ile Gly Glu Met Val Ser Pro Pro Gly Ser Asp Pro Glu Ser Asp
```

```
225                 230                 235                 240

Gly Gly Pro Gln Pro Pro Gln Asp Gln Gln
                245                 250
```

<210> SEQ ID NO 46
<211> LENGTH: 360
<212> TYPE: DNA
<213> ORGANISM: Artificial Sequence
<220> FEATURE:
<223> OTHER INFORMATION: Sequence is produced using the reverse translation tool located at: www.vivo.colostate.edu/molkit/rtranslate/index.html.

<400> SEQUENCE: 46

```
gaaccgccga gcgaaccgga aagcgaagaa agcgaaccgg aagaaccgca gagcagccag     60

ccgccgccgc cgagcgaacc gcagcagccg agccagcagc cgcagcagcc gagcccggaa    120

cagccgagcc agccggaaca gccggaaccg cagagcgaac cgcagcagcc ggaacagccg    180

cagccgccgc agccgccgcc gccggaacag agcccgagcc cgccggaaag ccagagccag    240

agcagcagcc cgagcccgca gcagccgagc ccggaaccga gcagcagcag ccagccggaa    300

cagccggaac cgccgcagga accggaaagc ccggaaccgc cgccgcagcc gcaggaacag    360
```

<210> SEQ ID NO 47
<211> LENGTH: 360
<212> TYPE: DNA
<213> ORGANISM: Artificial Sequence
<220> FEATURE:
<223> OTHER INFORMATION: Sequence is produced using the reverse translation tool located at: www.vivo.colostate.edu/molkit/rtranslate/index.html.

<400> SEQUENCE: 47

```
ccggaaccgg aaccgcagcc gccgagcccg cagagcccga gcccgccgcc gccgccgccg     60

ccgccgagcc agccgccgca gccgagcccg ccgccgagcg aaccggaacc gccgccgccg    120

gaaagcccgc agccgccgcc gcagcagccg ccgccgagcc cgcagagccc gagcccgccg    180

cagccgccgc cgagcccgcc gccgccgccg cagccgcagc cgccgcagag cgaaccgcag    240

ccgccgcagc cggaaccgcc gccgagcagc ccgccgccgc aggaaagcca ggaacagccg    300

agcgaaccgc cgccgccgcc gagcgaaccg agcagcgaag aaccgccgag cccgccgccg    360
```

<210> SEQ ID NO 48
<211> LENGTH: 360
<212> TYPE: DNA
<213> ORGANISM: Artificial Sequence
<220> FEATURE:
<223> OTHER INFORMATION: Sequence is produced using the reverse translation tool located at: www.vivo.colostate.edu/molkit/rtranslate/index.html.

<400> SEQUENCE: 48

```
ccgcaggaag aaccggaaca gagcccgcag ccggaagaac cgccgccgcc gcagcagcag     60

agcgaaccgg aaagcgaaga agaaagcgaa cagccggaac cgagcccgcc gccgccgccg    120

caggaaagcg aaagccagca ggaaagcgaa ccgcagccgc cgccgagccc gagcgaaccg    180

ccggaaagca gcccggaaga accgccggaa gaaccgagcc agcaggaaga agaaccggaa    240

agcgaaccga gcgaaagcga aagcccgccg gaacaggaac cgagcagcga accggaacag    300

ccgcagccgg aacagccgcc gagcgaagaa gaacagccgc aggaagaacc ggaacaggaa    360
```

<210> SEQ ID NO 49
<211> LENGTH: 360

<212> TYPE: DNA
<213> ORGANISM: Artificial Sequence
<220> FEATURE:
<223> OTHER INFORMATION: Sequence is produced using the reverse
translation tool located at:
www.vivo.colostate.edu/molkit/rtranslate/index.html.

<400> SEQUENCE: 49
ccgccgcagc cgccggaacc gccggaaggc cagccgccgc cgggcggcgg cccggaaccg 60
gaaggcccgc cgccgccgcc gccgccgccg ccgccgccgc agcagccgca ggaacagccg 120
ccgggcccgc cgcagccgga accgcagccg ccggaaccgc cggaaccggg cccgccgccg 180
ccgggcccgc cgcagccgca gccgccgggc ccgggcccgg aaggcccggg cccgcagccg 240
cagccgccgc cgccgccgga accgccggaa ggcggcccgc cgccgcagca gccgcagccg 300
ccggaacagg aaccgcagcc ggaaccggaa gaaggcccgc cgggcccggg cgaaccgccg 360

<210> SEQ ID NO 50
<211> LENGTH: 360
<212> TYPE: DNA
<213> ORGANISM: Artificial Sequence
<220> FEATURE:
<223> OTHER INFORMATION: Sequence is produced using the reverse
translation tool located at:
www.vivo.colostate.edu/molkit/rtranslate/index.html.

<400> SEQUENCE: 50
gaaccgggcc agccgccgcc gggcggcccg gaagaacagg aaccgccgga agaagaagaa 60
gaaccgccgc aggaacagcc gcaggaagaa gaaggcgaac cgcagggcga agaaccgggc 120
ggcggcgaac agggcccgga accgggccag ccgccgccgc agccgccgca gggcccgccg 180
ccgcagggcc agggcgaaca ggaaccgcag ccggaacagg aagaaggcca gccggaaggc 240
ccggaagaac cgccgggccc gcaggaagaa gaagaaccgg aagaaccgcc ggaaccgccg 300
ccgcagggcg gcgaagaacc gggccagccg ccgccgccgg aagaagaagg cgaacaggaa 360

<210> SEQ ID NO 51
<211> LENGTH: 360
<212> TYPE: DNA
<213> ORGANISM: Artificial Sequence
<220> FEATURE:
<223> OTHER INFORMATION: Sequence is produced using the reverse
translation tool located at:
www.vivo.colostate.edu/molkit/rtranslate/index.html.

<400> SEQUENCE: 51
gaaccggaac cgggcgaagg cgaagaaccg caggaagaac agggcccgga agaaccgggc 60
caggaagaag gcgaagaaca ggaagaagaa ggcgaaccgc cgcagggccc gcagcagcag 120
gaagaaccgg aaggcccgcc ggaagaacag caggaaccgc cgccggaaca gccggaaccg 180
gaagaaccgc cggaaggccc gccgccggaa gaagaaggcg aagaaggcga agaacagccg 240
cagggcccgg aagaaggcca gcaggaaccg cagccggaag gcggcccggg cccgccggaa 300
gaaccgccgg aagaaccgcc gcaggaaggc gaaccgccgg aagaagaaga agaaccggaa 360

<210> SEQ ID NO 52
<211> LENGTH: 750
<212> TYPE: DNA
<213> ORGANISM: Artificial Sequence
<220> FEATURE:
<223> OTHER INFORMATION: Sequence is produced using the reverse
translation tool located at:
www.vivo.colostate.edu/molkit/rtranslate/index.html.

<400> SEQUENCE: 52

-continued

```
gaagaacagc cggaaccgcc gcagagcgaa caggaagatc cggaagaacc gggtagctct     60
cagggtgaac cgggtccgcc ggaacagtct ccgggcggtc cgccggaaga accggaccag    120
ccgtctgaag aaccgccgcc ggaagaaccg cagccgcagt ctgaaggtag cccgggcccg    180
ccgccggaag gcccgccgga accggacccg gaagaagatg aaagcgaaga accgcagcaa    240
ccgccgtctc agccgagtcc gccgtctgaa ggccagccgc cggaaccgcc gcaagaacag    300
agttctagca gcgaagaatc tggtccgagc gaaccgagct ctgatccgag ttctgaagaa    360
agcgacccgc cggaaccgtc tccgagcccg ccgccgagtg aaggtagctc tgaaccgccg    420
cagcagccgg atgatccgtc gccgccgggc gaaccgcagc cggaagaaca accggaaccg    480
ggttctccgg atgatcagag cccgccgccg tcgccgagcc cgccgggtga accgcagggt    540
caaccggacg gctctccgag cggtgaaccg ggtcagagcg aagaaccgca accgggtggc    600
gatccggaac cgagcccgcc gggccaggaa gaaccgccgg aaccgtcacc ggaaggttct    660
ccgtcagaag gttcgccggg tgaaccgccg tctccgccgg gttctgaccc ggaatctgat    720
ggtggcccgc agccgccgca ggatcaacag                                     750
```

<210> SEQ ID NO 53
<211> LENGTH: 750
<212> TYPE: DNA
<213> ORGANISM: Artificial Sequence
<220> FEATURE:
<223> OTHER INFORMATION: Sequence is produced using the reverse translation tool located at: www.vivo.colostate.edu/molkit/rtranslate/index.html.

<400> SEQUENCE: 53

```
gaagaacagc cggaaccgat cgtgagcgaa caggaagatc cggaagaacc gggtagctcg     60
gtgtttgaaa ttctgccgcc ggaacagagc ccgggtggtc cgccggaaga accggatcaa    120
ccgtctgaag aaccggtgat ggaagaaatt caaccgcagc tggaaggctc tccgggtccg    180
ccgccggaag gtccgccgga accggacccg gaagaagatg aatcggaaga aattcagcaa    240
ccgattagcc aaccgtctcc gccgagcgaa ggtcaactgc tggaaccgct gcaggaacag    300
tctagttcgt ccgaagaaag cggtccgtct gaaccgtcga gcgaccccgag ctcggaagaa    360
agcgacccgc cggaaccgct gatctctgtc tttccgagtg aaggttctag cgaaccgccg    420
caacagccgg atgacctgtc gccgccgctg gaaccgcagc cggaagaaca accggaaccg    480
ggttcgccgg acgatcagtc tccgccgccg tctccgagcc cgccgggtga accgcagggt    540
cagccggatg gtagcccgtc tggtgaaccg ggtcaaagtg aagaaccgca gccgggtggc    600
gatccggaaa tcgttccgcc gattcaggaa gaactgccgg aaccgagccc ggaaggttct    660
ccgctggaag gttctattgg tgaaatggtc tcaccgccgg gttctgatcc ggaaagcgat    720
ggtggtccgc agccgccgca ggatcagcaa                                     750
```

<210> SEQ ID NO 54
<211> LENGTH: 375
<212> TYPE: DNA
<213> ORGANISM: Artificial Sequence
<220> FEATURE:
<223> OTHER INFORMATION: Double stranded sequence of the expression/cloning region of the pAquoProt plasmid

<400> SEQUENCE: 54

```
tcgatcagct ggtcgaccgc gaattaatac gactcactat aggggaattg tgagcggata     60
acaattcccc tctagaaata attttgttta actttaagaa ggagatatac catggcacac    120
```

catcaccatc accacggtgc cggttcgaat gatgacgacg acaagagtcc ggatcccaat 180
tgggaggata tcggtaccaa gcttgcggcc gcactcgagg gttacccata cgatgttcca 240
gattacgctt aaactagcgt agcttaatta acctaggctg ctgccaccgc tgagcaataa 300
ctagcataac cccttggggc ctctaaacgg gtcttgaggg gttttttgct gaaaggagat 360
ctgaacatat gccgg 375

<210> SEQ ID NO 55
<211> LENGTH: 375
<212> TYPE: DNA
<213> ORGANISM: Artificial Sequence
<220> FEATURE:
<223> OTHER INFORMATION: Double stranded sequence of the expression/cloning region of the pAquoProt plasmid

<400> SEQUENCE: 55
ccggcatatg ttcagatctc ctttcagcaa aaaacccctc aagacccgtt tagaggcccc 60
aaggggttat gctagttatt gctcagcggt ggcagcagcc taggttaatt aagctacgct 120
agtttaagcg taatctggaa catcgtatgg gtaaccctcg agtgcggccg caagcttggt 180
accgatatcc tcccaattgg gatccggact cttgtcgtcg tcatcattcg aaccggcacc 240
gtggtgatgg tgatggtgtg ccatggtata tctccttctt aaagttaaac aaaattattt 300
ctagagggga attgttatcc gctcacaatt cccctatagt gagtcgtatt aattcgcggt 360
cgaccagctg atcga 375

<210> SEQ ID NO 56
<211> LENGTH: 46
<212> TYPE: PRT
<213> ORGANISM: Artificial Sequence
<220> FEATURE:
<223> OTHER INFORMATION: pAquoProt plasmid coding sequences for a 6xHis tag, enterokinase (EK) cleavage site, multicloning site, and HA epitope tag

<400> SEQUENCE: 56

Met Ala His His His His His His Gly Ala Gly Ser Asn Asp Asp Asp
1 5 10 15

Asp Lys Ser Pro Asp Pro Asn Trp Glu Asp Ile Gly Thr Lys Leu Ala
20 25 30

Ala Ala Leu Glu Gly Tyr Pro Tyr Asp Val Pro Asp Tyr Ala
35 40 45

<210> SEQ ID NO 57
<211> LENGTH: 380
<212> TYPE: DNA
<213> ORGANISM: Artificial Sequence
<220> FEATURE:
<223> OTHER INFORMATION: Double stranded sequence of the expression/cloning region of the pAquoKin plasmid

<400> SEQUENCE: 57
tcgatcagct ggtcgaccgc gaattaatac gactcactat aggggaattg tgagcggata 60
acaattcccc tctagaaata attttgttta actttaagaa ggagatatac catggcacac 120
catcaccatc accacggtgc cggttcgaat gatgacgacg acaagagtcc ggatcccaat 180
tgggaggata tcggtaccaa gcttgcggcc gcactcgagg gtgattacaa ggatgacgac 240
gataagagcg cttaaactag cgtagcttaa ttaacctagg ctgctgccac cgctgagcaa 300
taactagcat aaccccttgg ggcctctaaa cgggtcttga ggggtttttt gctgaaagga 360
gatctgaaca tatgccggat 380

-continued

```
<210> SEQ ID NO 58
<211> LENGTH: 380
<212> TYPE: DNA
<213> ORGANISM: Artificial Sequence
<220> FEATURE:
<223> OTHER INFORMATION: Double stranded sequence of the
      expression/cloning region of the pAquoKin plasmid

<400> SEQUENCE: 58

atccggcata tgttcagatc tcctttcagc aaaaaacccc tcaagacccg tttagaggcc      60

ccaaggggtt atgctagtta ttgctcagcg gtggcagcag cctaggttaa ttaagctacg     120

ctagtttaag cgctcttatc cagcagtagg aacattagac cctcgagtgc ggccgcaagc     180

ttggtaccga tatcctccca attgggatcc ggactcttgt cgtcgtcatc attcgaaccg     240

gcaccgtggt gatggtgatg gtgtgccatg gtatatctcc ttcttaaagt taaacaaaat     300

tatttctaga ggggaattgt tatccgctca caattcccct atagtgagtc gtattaattc     360

gcggtcgacc agctgatcga                                                 380


<210> SEQ ID NO 59
<211> LENGTH: 47
<212> TYPE: PRT
<213> ORGANISM: Artificial Sequence
<220> FEATURE:
<223> OTHER INFORMATION: pAquoKin plasmid coding sequences for a 6xHis
      tag, enterokinase cleavage site, multicloning site, and
      the FLAG epitope tag

<400> SEQUENCE: 59

Met Ala His His His His His His Gly Ala Gly Ser Asn Asp Asp Asp
 1               5                  10                  15

Asp Lys Ser Pro Asp Pro Asn Trp Glu Asp Ile Gly Thr Lys Leu Ala
            20                  25                  30

Ala Ala Leu Glu Gly Asp Tyr Lys Asp Asp Asp Asp Lys Ser Ala
        35                  40                  45
```